(12) United States Patent
Goldsmith et al.

(10) Patent No.: US 7,838,287 B2
(45) Date of Patent: Nov. 23, 2010

(54) LIBRARY OF A COLLECTION OF CELLS

(75) Inventors: Neil Goldsmith, Oxford (GB); Alexandra M. P. Santana Sørensen, Holte (DK); Søren V. S. Nielsen, Allerød (DK)

(73) Assignee: Evolva SA (CH)

( * ) Notice: Subject to any disclaimer, the term of this patent is extended or adjusted under 35 U.S.C. 154(b) by 782 days.

(21) Appl. No.: 10/466,960

(22) PCT Filed: Jan. 25, 2002

(86) PCT No.: PCT/DK02/00056

§ 371 (c)(1),
(2), (4) Date: Jan. 6, 2004

(87) PCT Pub. No.: WO02/059297

PCT Pub. Date: Aug. 1, 2002

(65) Prior Publication Data

US 2004/0241672 A1    Dec. 2, 2004

Related U.S. Application Data

(60) Provisional application No. 60/300,863, filed on Jun. 27, 2001.

(30) Foreign Application Priority Data

Jan. 25, 2001  (DK) .............................. 2001 00128
May 1, 2001  (DK) .............................. 2001 00679

(51) Int. Cl.
   *C12N 15/00* (2006.01)
   *C12P 19/34* (2006.01)
   *C07H 21/02* (2006.01)
(52) U.S. Cl. ................... 435/320.1; 435/91.2; 536/23.1
(58) Field of Classification Search ............. 435/320.1, 435/91.2; 536/23.1
   See application file for complete search history.

(56) References Cited

U.S. PATENT DOCUMENTS

| | | | |
|---|---|---|---|
| 5,316,922 A | 5/1994 | Brown et al. | |
| 5,783,431 A | 7/1998 | Peterson et al. | |
| 5,824,485 A | 10/1998 | Thompson et al. | |
| 5,837,458 A | 11/1998 | Minshull et al. | |
| 5,958,672 A | 9/1999 | Short | |
| 6,001,574 A | 12/1999 | Short et al. | |
| 6,004,788 A | 12/1999 | Short | |
| 6,025,155 A | 2/2000 | Hadlaczky et al. | |
| 6,030,779 A | 2/2000 | Short | |
| 6,054,267 A | 4/2000 | Short | |
| 6,057,103 A | 5/2000 | Short | |
| 6,117,679 A | 9/2000 | Stemmer | |
| 6,136,567 A * | 10/2000 | Duchars et al. ............ | 435/71.2 |
| 6,165,793 A | 12/2000 | Stemmer | |
| 6,174,673 B1 | 1/2001 | Short et al. | |
| 6,268,140 B1 | 7/2001 | Stuart | |
| 6,294,325 B1 * | 9/2001 | Wetmur ........................ | 435/6 |
| 7,052,876 B1 * | 5/2006 | Finney et al. ............... | 435/91.1 |
| 7,105,297 B2 | 9/2006 | Minshull et al. | |
| 2001/0041333 A1 | 11/2001 | Short et al. | |
| 2002/0025517 A1 | 2/2002 | Minshull et al. | |
| 2004/0110174 A1 | 6/2004 | Goldsmith et al. | |
| 2005/0019924 A1 | 1/2005 | Hitzeman et al. | |
| 2005/0158860 A1 | 7/2005 | Goldsmith et al. | |
| 2005/0164162 A1 | 7/2005 | Sorensen et al. | |
| 2006/0068472 A1 | 3/2006 | Caldwell et al. | |
| 2006/0252156 A1 | 11/2006 | Goldsmith et al. | |

FOREIGN PATENT DOCUMENTS

| | | |
|---|---|---|
| EP | 0329203 | 1/1984 |
| WO | 89/10566 | 11/1989 |
| WO | WO 91/00920 | 1/1991 |
| WO | 95/08647 | 3/1995 |
| WO | 95/11986 | 5/1995 |
| WO | WO 96/34112 | 10/1996 |
| WO | 97/31118 | 8/1997 |
| WO | WO 97/35966 | 10/1997 |
| WO | WO 97/40183 | 10/1997 |
| WO | 97/44470 | 11/1997 |
| WO | WO 98/01573 | 1/1998 |
| WO | WO 98/17811 | 4/1998 |
| WO | WO 98/31837 | 7/1998 |
| WO | 98/38490 | 9/1998 |
| WO | 98/41869 | 9/1998 |
| WO | 98/54339 | 12/1998 |
| WO | 98/58085 | 12/1998 |
| WO | WO 99/10539 | 3/1999 |
| WO | 99/35260 | 7/1999 |
| WO | WO 99/45154 | 9/1999 |

(Continued)

OTHER PUBLICATIONS

Pierce et al. PNAS 89:2056-2060; 1992.*

(Continued)

*Primary Examiner*—Fereydoun G Sajjadi
(74) *Attorney, Agent, or Firm*—McDonnell Boehnen Hulbert & Berghoff LLP

(57) ABSTRACT

The present invention relates to combinatorial gene expression libraries and methods for making these. Such libraries are useful in discovery of novel and/or enhanced metabolic pathways leading to the production of novel compounds for e.g drug discovery and/or to the production of known compounds in novel quantities or in novel compartments of the cells. The expression libraries in particular are composed of host cells capable of co-ordinated and controllable expression of large numbers of heterologous genes in the host cells.

13 Claims, 13 Drawing Sheets

FOREIGN PATENT DOCUMENTS

| | | |
|---|---|---|
| WO | WO 00/04190 | 1/2000 |
| WO | 00/08212 | 2/2000 |
| WO | WO 00/06715 | 2/2000 |
| WO | 00/17643 | 3/2000 |
| WO | WO 00/12680 | 3/2000 |
| WO | WO 00/52180 | 9/2000 |
| WO | WO 00/53744 | 9/2000 |
| WO | WO 00/58517 | 10/2000 |
| WO | WO 00/77262 | 12/2000 |
| WO | 01/32829 | 5/2001 |
| WO | WO 01/73000 | 10/2001 |
| WO | 02/059290 | 8/2002 |
| WO | 02/059296 | 8/2002 |
| WO | 02/059297 | 8/2002 |
| WO | 02/059330 | 8/2002 |
| WO | 03/062419 | 7/2003 |
| WO | 03/106639 | 12/2003 |
| WO | 2004/016791 | 2/2004 |

OTHER PUBLICATIONS

Jeffrey L. Stein et al., Nucleotide sequence and expression of a deep-sea ribulose-1,5,—bisphospate carboxylase gene cloned from a chemoautotropic bacterial endosymbiont, Proc. Natl. Acad. Sci. USA, vol. 87, pp. 8850-8854, Nov. 1990.

T. Lotan et al., Cloning and expression in *Escherichia coli* of the gene encoding β-C-4-oxygenase, that coverts β carotene to the ketocarotenoid canthaxanthin in *Haematococcus pluvialis*, FEBS letters 364, 1995, pp. 125-128.

J. Staudinger, Interactions among vertebrate helix-loop-helix proteins in yeast using the two-hybrid system., J Biol Chem. Mar. 5, 1993; 268(7): 4608-11. Abstract only.

Raphael Nir et al., Flow cytometry sorting of viable bacteria and yeasts according to β-galactosidase activity, Applied and environmental microbiology, Dec. 1990, p. 3861-3866, vol. 56, No. 12.

P. J. McCormack et al., Production of antibacterial compounds by phylloplane-inhabiting yeasts and yeastlike fungi, Applied and environmental microbiology, Mar. 1994, p. 927-931, vol. 60, No. 3.

Smith, et al., Construction and Use of Signal Sequence Selection Vectors in *Escherichia coli* and *Bacillus subtilis*, Journal of Bacteriology, vol. 169, No. 7, pp. 3321-3328, Jul. 1987.

Gift et al., "FACS-based isolation of slowly growing cells: Double encapsulation of yeast in gel microdrops," Nature Biotechnology, 14:884-887 (1996).

International Search Report for WO 2002/059290 mailed Dec. 23, 2002.

International Search Report for WO 2002/059296 mailed Oct. 23, 2002.

International Search Report for WO 2002/059297 mailed Jan. 15, 2003.

International Search Report for WO 2003/062419 mailed Jun. 11, 2003.

International Search Report for WO 2004/016791 mailed Dec. 5, 2003.

Leahy et al., "Transcription from plasmid expression vectors is increased up to 14-fold when plasmids are transfected as concatemers," Nucleic Acids Research, 25(2):449-450 (1997).

Zhu et al., "Three-Color Flow Cytometry Analysis of Tricistronic Expression of eBFP, eGFP, and eYFP Using EMCV-IRES Linkages," Cytometry, 37:51-59 (1999).

Blattner et al., "The Complete Genome Sequence of *Escherichia coli* K-12," Science, 277:1453-1462 (Sep. 5, 1997).

Diatchenko et al., "Suppression subtractive hybridization: A method for generating differentially regulated or tissue-specific cDNA probes and libraries," PNAS, 93:6025-6030 (Jun. 1996).

Carninci et al., "Normalization and Subtraction of Cap-Trapper-Selected cDNAs to Prepare Full-Length cDNA Libraries for Rapid Discovery of New Genes," Genome Res., 10:1617-1630 (2000).

Wood et al., "Complementary DNA Coding Click Beetle Luciferases Can Elicit Bioluminescene of Different Colors," Science, 244:700-702 (May 12, 1989).

Sehested et al., "Chinese Hamster Ovary Cells Resistant to the Topoisomerase II Catalytic Inhibitor ICRF-159: A Typr49Phe Mutation Confers High-Level Resistance to Bisdioxopiperazines," Cancer Research, 58:1460-1468 (Apr. 1, 1998).

Weinshilbourn, R.M. et al., "Sulfotransferase molecular biology: cDNAs and genes," The FASEB Journal, 11:3-14 (Jan. 1997).

Bouska. et al., "Improving the in Vivo Duration of 5-Lipoxygenase Inhibitors—Application of an in Vitro Glucuronosyltransferase Assay," Drug Metab. Dispos., 25(9):1032-1038 (1997).

Burke et al., "Cloning of Large Segments of Exogenous DNA into Yeast by Means of Artificial Chromosome Vectors," Science, 236:806-812 (May 15, 1987).

Foster, Barbara et al., "Pharmacological Rescue of Mutant p53 Conformation and Function," Science, 286:2507-2510 (1999).

Bonaldo et al., "Normalization and Subtraction: Two Approaches to Facilitate Gene Discovery," Genome Research, 6:791-806 (1996).

Benderitter, M. et al., "Simultaneous analysis of radio-induced membrane alteration and cell viability by flow cytometry," Cytometry, 39(2):151-157 (2000).

Sears, D.D. et al., "An Implanted Recombination Hot Spot Stimulates Recombination and Enhances Sister Chromatid Cohesion of Heterologous YACs During Yeast Meiosis," Genetics, 138:1055-1065 (Aug. 26, 1994).

Chen and Struhl, "Yeast mRNA initiation sites are determined primarily by specific sequences, not by the distance from the TATA element," EMBO J., 4(12):3273-3280 (1985).

Chang, LMS, et al., "Deoxynucleotide-polymerizing Enzymes of Calf Thymus Gland," J. Biol. Chem., 246:909-916 (Feb. 25, 1971).

Davis, CA et al., "Test of intron predictions reveals novel splice sites, alternatively spliced mRNAs and new introns in meiotically regulated genes of yeast," Nucleic Acids Res., 28(8):1700-1706 (Mar. 1, 2000).

Sive et al., "A simple subtractive hybridization technique emplmoying phoactivatable biotin and phenol extraction," Nucleic Acid Res., 16:10937 (Sep. 29, 1988).

Salerno et al., "Differential transcriptional regulation of the apoA1 gene by retinoic acid receptor homo-and heterodimers in yeast," Nucleic Acids Res., 24(4):566-572 (1996).

Coldham et al., "Evaluation of a Recombinant Yeast Cell Estrogen Screening Assay," Environ. Health Perspect., 105(7):734-742 (Jul. 1997).

Jordan, S.P. et al., "Activity and dimerization of human immunodeficiency virus protease as a function of solvent composition and enzyme concentration," J. Biol. Chem., 267(28):20028-20032 (Oct. 5, 1992).

Wasserman R. et al., "Use of Yeast in the Study of Anticancer Drugs Targeting DNA Topoisomerases: Expression of a Functional Recombinant Human DNA Topoisomerase IIα in Yeast," Cancer Research, 53:3591-3596 (Aug. 1, 1993).

Smith et al., "Amplification of large artificial chromosomes," Proc. Natl. Acad. Sci., 87:8242-8246 (Nov. 1990).

Dubois, R. et al., "Cyclooxygenase in biology and disease," FASEB J., 12:1063-1073 (Sep. 1998).

Ziegler, J. et al., "Cancer and Arthritis Share Underlying Processes," J. Nat. Cancer Inst., 90(11):802-803 (1998).

Cordon-Cardo et al., "Multidrug-resistance gene (P-glycoprotein) is expressed by endothelial cells at blood-brain barrier sites," Proc. Natl. Acad. Sci., 86(2): 695-698 (Jan. 1989).

Rao et al., "Choroid plexus epithelial expression of MDR1 P glycoprotein and multidrug resistance-associated protein contribute to the blood-cerebrospinal-fluid drug-permaeability barrier," Proc. Natl. Acad. Sci., 96(7): 3900-3905 (Mar. 1999).

Schinkel et al., "Normal viability and altered pharmacokinetics in mice lacking mdr1-type (drug-transporting) P-glycoproteins," Proc. Natl. Acad. Sci., 94: 4028-4033 (Apr. 1997).

Wijnholds J et al., "Multidrug resistance protein 1 protects the choroid plexus epithelium and contributes to the blood-cerebrospinal fluid barrier," J Clin Invest, 105(3): 279-85 (Feb. 2000).

Ihler, G.M., "Erythrocyte Carriers," Pharm. Ther., 20(2): 151-169 (1983).

Kunst et al., "The complete genome sequence of the Gram-positive bacterium *Bacillus subtilis*," Nature, 390:249-256 (Nov. 20, 1997).

Armitage, B., "Photocleavage of nucleic acids," Chem. Rev. 98:1171-1200 (1998).

Dervan, P.B. et al., "Sequence-specific DNA recognition by polyamides," Curr. Opin. Chem. Biol., 3:688-693 (Dec. 1, 1999).

Nielsen, P.E., "Peptide nucleic acid: a versatile tool in genetic diagnostics and molecular biology," Curr. Opin. Biotechnol., 12:16-20 (Feb. 1, 2001).

Bashkin, J.K., "Introduction to RNA/DNA Cleavage," Chem Rev, 98(3): 937-938 (Apr. 17, 1998).

Spingola, M. et al., "Genome-wide bioinformatic and molecular analysis of introns in *Saccharomyces cerevisiae*," RNA, 5(2):221-234 (1999).

Tsang et al., "Entrapment of Proteins, Viruses, Bacteria, and DNA in Erythrocytes during Endocytosis," Journal of Applied Biochemistry, 4:418-435 (1982).

Ali et al, "Normalisation of cereal endosperm EST libraries for structural and functional genomic analysis," Plant Mol. Biol. Reporter, 18:123-132 (Jun. 2000).

Metcalf et al., "Construction of new β-glucuronidase cassettes for making transcriptional fusions and their use with new methods for allele replacement," Gene, 129:17-25 (Jul. 15, 1993).

Sahar et al., "Flow cytometric analysis of entire microbial colonies," Cytometry, 15:213-221 (1994).

Murray et al.., "Construction of artificial chromosomes in yeast," Nature, 305:189-193 (Sep. 15, 1983).

Sauer, B., "[53] Manipulation of transgenes by site-specific recombination: Use of cre recombinase," Methods Enzymol., 225:890-900 (1993).

Landy, A., "Dynamic, Structural, and Regulatory Aspects of lambda Site-Specific Recombination," Ann. Rev. Biochem., 58:913-941 (Jul. 1989).

Hugerat Y. et al., "A Versatile Method for Efficient YAC Transfer between Any Two Strains," Genomics, 22(1):108-117 (Jul. 1, 1994).

Curran, B.P. et al., "Protoplast Fusion in *Saccharomyces cerevisiae*," Methods Mol. Biol., Chapter 5, vol. 53:45-49 (1996).

An, G.H. et al., "Isolation and characterization of carotenoid hyperproducing mutants of yeast by flow cytometry and cell sorting," Biotechnology, 9:70-73 (Jan. 1991).

McCall, J. et al., "Pyrimidine and triazine 3-oxide sulfates: a new family of vasodilators," J. Med. Chem., 26:1791-1793 (1983).

Wittrup et al., "Microencapsulation selection for isolation of yeast mutants with increased secretion of *Aspergillus awamori* glucoamylase," Biotechnolog. Bioeng., 42:351-356 (Accepted Feb. 17, 1993).

Chen et al., "Inhibition of Fumarate Reductase in *Leishmania major* and *L. donovani* by Chalcones," Antimicrob. Agents Chemother., 45(7):2023-2029 (2001).

Raftogianis, R.B. et al., "Phenol sulfotransferase pharmacogenetics in humans: Association of common SULT1A1 alleles with TS PST phenotype," Biochem Biophys Res Commun. (BBRC), 239:298-304 (Oct. 9, 1997).

Radominska-Pandya, A. et al., "Structural and functional studies of UDP-glucuronosyltransferases," Drug Metab. Rev., 31:817-899 (Nov. 1999).

Karin, M., "The NF-kappa B activation pathway: its regulation and role in inflammation and cell survival," Cancer J Sci Am, 4:S92-9 (1998).

Barnes, Peter, "Nuclear factor-κB," Int. J. Biochem. Cell. Biol., 29(6):867-870 (Jun. 1997).

Handel, ML, "Transcription factors AP-1 and NFkB: where steroids meet the gold standard of anti-rheumatic drugs," Inflamm. Res., 46:282-286 (1997).

Malonne, H. et al., "DNA topoisomerase targeting drugs: mechanisms of action and perspectives," Anti-Cancer Drugs, 8(9):811-822 (Oct. 1997).

Nitiss et al, "Yeast Systems for Demonstrating the Targets of Anti-topoisomerase II Agents," Methods in Molecular Biology, 95:315-327 (2001).

Inui K. et al., "Transepithelial transport of oral cephalosporins by monolayers of intestinal epithelial cell line Caco-2: specific transport systems in apical and basolateral membranes.," J. Pharmacol Exp Ther., 261:195-201 (Apr. 1992).

Lu, S. et al., "Effect of Subculturing on the Epithelial Properties of Caco-2 Cells as a Transport Model," Pharm. Res. 11:S-258 (Oct. 14, 1994).

Bjorge, S. et al., "Evidence for Glucuronide Conjugation of p-Nitrophenol in the Caco-2 Cell Model," Pharm Res., 8(11):1441-1443 (Nov. 1991).

Gottesman MM et al., "Biochemistry of Multidrug Resistance Mediated by the Multidrug Transporter," Ann. Rev. Biochem, 62: 385-427 (1993).

Kurelec, B. et al., "Distinct glutathione-dependent enzyme activities and a verapamil-sensitive binding of xenobiotics in a fresh-water mussel *Anodonta cygnea*," Biochem Biophys Res Comm, 164(2): 934-940 (Oct. 31, 1989).

Kurelec, B, "The multixenobiotic resistance mechanism in aquatic organisms," Crit Rev Toxicol, 22(1): 23-43 (1992).

Ohgiya, S. et al., "Cloning of Human Cytochrome P-450 cDNA and its Expression in *Saccharomyces cerevisiae*," Biochem Int., 18(2):429-438 (Feb. 1989).

Winters, D.K., "Expression of a catalytically active human cytochrome P-4502E1 in *Escherichia coli*," Biochim Biophys Acta, 1156:43-49 (Dec. 8, 1992).

Crespi, C.L. et al., "A Metabolically Competent Human Cell Line Expressing Five cDNAs Encoding Procarcinogen-Activating Enzymes: Application to Mutagenicity Testing," Chem. Res. Toxicol., 4:566-572 (1991).

Nelson, D.R., "Cytochrome P450 and the individuality of species," Arch Biochem Biophys, 369:1-10 (1999).

Guengerich, F.P., Cytochrome, P450: Structure, Mechanism, and Biochemistry (2nd Edition), Chapter 14, edited by Paul R. Ortiz de Montellano, Plenum Press, New York, (1995).

Shimada, T. et al., "Interindividual variations in human liver cytochrome P-450 enzymes involved in the oxidation of drugs, carcinogens and toxic chemicals: studies with liver microsomes of 30 Japanese and 30 Caucasians," J. Pharmacol. Exp. Ther., 270(1):414-423 (Jul. 1994).

Ortiz De Montellano, P.R., Cytochrome, P450: Structure, Mechanism, and Biochemistry (2nd Edition), Chapter 8, edited by Paul R. Ortiz de Montellano, Plenum Press, New York, (1995).

Rettie, A.E. et al., Handbook of Drug Metabolism, edited by Thomas F. Woolf, Marcel Dekker, Inc., New York, pp. 131-147 (1999).

Ziegler, D.M., "Recent studies on the structure and function of multisubstrate flavin-containing monooxygenases," Annu. Rev. Pharmacol. Toxicol., 33:179-199 (1993).

Miller, J.A., "Sulfonation in Chemical Carcinogenesis • History and Present Status," Chem. Biol. Interact., 92:329-341 (1994).

Coffman, B. et al., "Accelerated Communication: Human UGT2B7 Catalyzes Morphine Glucuronidation," Drug Metabolism and Disposition, 25(1):1-4 (1996).

Chen et al., "Inhibition of Fumarate Reductase in *Leishmania major* and *L. donovani* by Chalcones" Antimicrob. Agents Chemother., 45(7):2023-2029 (Jul. 2001).

Yamazaki et al., "Lack of Electron Transfer from Cytochrome b5 in stimulation of Catalytic Activities of Cytochrome P450 3A4," The Journal of Biological Chemistry, 271(44):27438-27444 (Nov. 1, 1996).

* cited by examiner

Plate 2: Met Promoter ON

Plate 4: Both Promoters ON

Plate 1: Promoters repressed

Plate 3: CUP Promoter ON

LIBRARY OF A COLLECTION OF CELLS

CROSS-REFERENCE

This application is a section 371 U.S. national phase of international application PCT/DK02/00056, filed Jan. 25, 2002, which claims the benefit of U.S. provisional application Ser. No. 60/300,863, filed Jun. 27, 2001, which is hereby incorporated by reference in its entirety. The application further claims priority from Danish patent application numbers PA 2001 00128, filed Jan. 25, 2001 and PA 2001 00679, filed on May 1, 2001, which are hereby incorporated by reference in their entirety. All patent and nonpatent references cited in the application, or in the present application, are also hereby incorporated by reference in their entirety.

The present invention relates to a library of a collection of cells and a method for producing said library. The library is useful as a starting material for evolving cells or compositions having new properties.

TECHNICAL FIELD

The present invention relates to combinatorial gene expression libraries and methods for making these. Such libraries are useful in discovery of novel and/or enhanced metabolic pathways leading to the production of novel compounds for e.g. drug discovery and/or to the production of known compounds in novel quantities or in novel compartments of the cells.

BACKGROUND OF THE INVENTION

Methods are known to provide recombined combinatorial gene expression libraries by crossing and recombination between cells comprising expression constructs (WO 00/52180 Terragen Discovery Ltd). Through the recombination, which may be carried out in vitro using the recA recombination enzyme, novel genes are obtained, which may or may not be functional in the host cell.

One drawback of the libraries of the prior art is that evolution of the libraries may only be obtained through crossing and recombination between cells whereby homologous or homeologous genes are recombined thereby resulting in novel genes yielding gene products with slightly changed properties such as substrate specificity, solubility, cellular location etc.

Furthermore once the expression constructs have been inserted into the cells the specific gene combinations of a cell is static. Novel combinations may be obtained by crossing and recombination, but this will also lead to formation of novel genes through cross-over. The novel genes may or may not be functional anymore.

Furthermore, the expression of the inserted expression construct is a co-expression of all the genes inserted into any one cell. When a large number of heterologous genes from a wide variety of distantly related species is assembled in one cell, chances are great that some of the heterologous genes are lethal or sub-lethal to the cell, or that several gene products will compete for the same substrates. When only co-expression of the inserts is possible novel metabolic pathways may remain undiscovered due to this fact or due to the fact that the novel metabolite was being further metabolised to a known metabolite by another inserted enzyme.

SUMMARY OF THE INVENTION

According to a first aspect the invention relates to a library comprising a collection of individual cells, the cells being denoted $cell_1, cell_2, \ldots, cell_i$, wherein $i \geq 2$, each cell comprising at least one concatemer of individual oligonucleotide cassettes, each concatemer comprising a nucleotide sequence of the following formula:

$$[rs_2\text{-SP-PR-X-TR-SP-}rs_1]_n$$

wherein $rs_1$ and $rs_2$ together denote a restriction site, SP denotes a spacer of at least two bases, X denotes an expressible nucleotide sequence, PR denotes a promoter, capable of regulating the expression of X in the cell, TR denotes a terminator, and $n \geq 2$, and wherein at least one concatemer of $cell_1$ is different from a concatemer of $cell_2$.

The library is preferably one wherein substantially all $rs_1$-$rs_2$ sequences are recognized by the same restriction enzyme, more preferably wherein substantially all $rs_1$-$rs_2$ sequences are substantially identical.

The library according to this embodiment of the invention may in any one cell comprise a unique and preferably random combination of a high number of expression cassettes being heterologous to the host cells. Through this random combination of expression cassettes novel and unique combinations of gene products are obtained in each cell. Such libraries are especially adapted in the discovery of novel metabolic pathways created through the non-native combinations of gene products.

Due to the common structure of the expression cassettes, these may be assembled easily into concatemers and inserted into the host cells via appropriate vectors. Furthermore, the cassettes may at any point be excised from the host cells again using a restriction enzyme specific for the $rs_1$-$rs_2$ restriction site preferably without excising the host cell's native genes. After excision the expression cassettes may be mixed with other expression cassettes of similar structure and be re-concatenated and re-inserted into another host cell in another combination.

A further advantage of the common structure of the expression cassettes, is that the common $rs_1$-$rs_2$ sequence may be used as a tag for targeted PCR amplification of the expression constructs.

The expressible nucleotide sequences may conveniently arise from a cDNA library obtained from one or more expression states, wherein the cDNA clones have been inserted into expression constructs. Following excision of the expression construct from the vector comprising the construct in the cDNA library, the multitude of constructs may be concatenated and inserted into a host cell.

Each unique cell according to the invention may comprise a selection of expressible nucleotide sequences from just one expression state and can thus be assembled from one library representing this expression state or it may comprise cassettes from of a number of different expression states. The variation among and between cassettes in the cells may be such as to minimise the chance of cross over as the host cell undergoes cell division such as through minimising the level of repeat sequences occurring in concatemers, since it is not an object of this embodiment of the invention to obtain inter- or intra-chromosomal recombination of the concatemers. Nor to obtain recombination with epitopes of the host cell.

The contents of the concatemers may be mixed according to any criteria. Thus a library or a sub-library of individual cells may comprise cells having a common phenotype, cells comprising expression cassettes from a common source, cells comprising specific combinations of promoter and expressible nucleotide sequences. A library or sub-library may also or alternatively comprise a collection of individual cells comprising one or more common concatemers in addition to differing concatemers; wherein the common concatemer may represent expression constructs from a common source or coding for genes with a property in common.

According to another aspect the invention relates to a library comprising a collection of individual cells, the cells being denoted $cell_1, cell_2, \ldots, cell_i$, wherein $i \geq 2$, each cell comprising at least two expression cassettes comprising a nucleotide sequence of the following formula:

[$rs_2$-SP-PR-X-TR-SP-$rs_1$]

wherein $rs_1$ and $rs_2$ together denote a restriction site, SP denotes a spacer of at least two bases, X denotes an expressible nucleotide sequence, PR denotes a promoter, capable of regulating the expression of X in cell, TR denotes a terminator, and wherein at least one of the expression cassettes comprises an expressible nucleotide sequence heterologous to the to cell, and at least one of the cassettes of cell, is different from the cassettes of $cell_2$.

According to this aspect of the invention, the cells are defined with reference to the expression cassettes. This aspect of the invention shares many advantages with the first aspect of the invention.

According to a third aspect the invention relates to a library comprising a collection of individual cells, the cells being denoted $cell_1, cell_2, \ldots, cell_i$, wherein $i \geq 2$, each cell comprising a random combination of heterologous oligonucleotides having the general formula:

[PR-X]

wherein X denotes an expressible nucleotide sequence, and PR denotes an independently controllable promoter being operably associated with X.

In a library according to this aspect of the invention, the mixing of gene products may not only be done upon insertion of the expressible nucleotide sequences, but also during expression by inducing and/or repressing one or more promoters each regulating the expression of a random group of expressible nucleotide sequences. Thus in each cell, a unique sub-set of genes may be induced and/or repressed at any point.

This feature adds another level of potential variation in the discovery of novel biochemical pathways. By the,up and down regulation of independent promoters any combination of sub-sets of genes may be turned on or off in a population of cells having a random combination of promoters and expressible nucleotide sequences.

In the evolution of novel biochemical pathways based on the insertion and expression of a high number of heterologous genes in a population of cells, it is highly likely that cells will be killed due to the formation of lethal gene products. If each cell comprises just one lethal gene, the co-expression of a number of heterologous genes will not lead to any novel biochemical pathways. By having a random combination of promoters and expressible nucleotide sequences, it may be possible to down regulate lethal or sub-lethal genes without affecting the expression of the other heterologous expression constructs.

It is also possible to use the coordinated expression obtained through the random combination of promoters and expressible nucleotide sequences from the same pool of expressible nucleotide sequences to identify expressible nucleotide sequences involved in a desired or unwanted property (e.g. lethality or sub-lethality). In a population according to this aspect of the invention, each cell may in principle comprise more or less the same heterologous expressible nucleotide sequences, the difference between the cells being the groups of expressible nucleotide sequences that are induced/repressed by a given promoter. In such a population of cells a desired or unwanted property will be identified in different cells following induction/repression of different promoters. As an illustrative example, in cell A the property may be associated with induction of promoter 1, 2, and 3, and in cell B the property may be associated with induction of promoter 5 and 6. With this information it is possible to target the property (or properties) to the group of expressible nucleotide sequences associated with these promoters in these cells. The expression constructs may be isolated using knowledge about the promoter nucleotide sequence and sequences common for the identified cells may be identified. Thus, by-turning on and off only certain sub-sets of genes at a time, it is possible to identify which gene combinations have given a particular phenotype.

According to a further aspect the invention relates to a library comprising at least one library or at least one sub-library as defined above. In the evolution of novel biochemical pathways, it may be preferable to use a number of libraries or sub-libraries and to evolve these in parallel or mix the libraries in order to improve the chances of identifying a desired property.

According to a further aspect the invention relates to a method of producing a library comprising a collection of individual cells, comprising the steps:

i) providing a population of nucleotide cassettes having the general formula [$rs_2$-SP-PR-X-TR-SP-$rs_1$], wherein $rs_1$ and rs2 together denote a restriction site, SP denotes a spacer of at least two bases, X denotes an expressible nucleotide sequence, PR denotes a promoter, capable of regulating the expression of X in the cell, TR denotes a terminator, and ii) assembling random sub-sets of the cassettes into concatemers comprising at least two casettes, iii) ligating the concatemers into vectors, iv) introducing vectors into host cells, v) mixing at least two cells so that at least one concatemer of a first cell comprises a random sub-set of cassettes being different from a random sub-set of cassettes of a concatemer of a second cell.

The assembly of concatemers is facilitated by the common structure of the expression cassettes. When the $rs_1$-$rs_2$ restriction site produces sticky ends with a predetermined nucleotide sequence the assembly of the concatemers becomes especially easy to perform.

The randomisation of the cassettes may be done at any stage, i.e. during a preceding step in which an entry library (for storing and amplifying cassettes) is produced or during the insertion into vectors and/or during the transformation into host cells. Preferably the randomisation is done during the concatenation step.

According to another aspect the invention relates to a method of producing a library comprising a collection of individual cells, comprising the steps of:

i) inserting at least two expressible nucleotides into the cloning site of at least two primary vectors comprising a cassette, the cassette comprising a nucleotide sequence of the general formula in 5'→3' direction: [RS1-RS2-SP-PR-CS-TR-SP-RS2'-RS1'] wherein RS1 and RS1' denote first restriction sites, RS2 and RS2' denotes another restriction site different from RS1 and RS1', SP denotes a spacer sequence of at least two nucleotides, PR denotes a promoter, CS denotes a cloning site, and TR denotes a terminator;

ii) excising the cassettes using at least a restriction enzyme specific for RS1, RS1' and RS2 and RS2' obtaining expression cassettes having the general formula [$rs_2$-SP-PR-X-TR-SP-$rs_1$], wherein $rs_1$-$rs_2$ together denote a restriction site, and wherein X denotes an expressible nucleotide sequence;

iii) inserting the expression cassettes into a vector;

iv) transferring the expression cassettes into at least two host cells; and v) mixing at least two host cells having different cassettes.

According to this method for producing a library of individual cells the source expressible nucleotide sequences are first ligated into a primary vector comprising a cloning site and a cloning cassette. This primary vector may be maintained in a cDNA library and reisolated for excision of the expression cassettes and insertion into a host cell. Through this process the expressible nucleotide sequences are given a common structure which makes it possible to clone the cassettes into a predetermined cloning site in a vector and to remove the cassettes selectively from the host cells later.

According to a final aspect the invention relates to a method of producing a library comprising a collection of individual cells, comprising the steps:

i) providing at least one expressible nucleotide sequence, ii) ligating at least one expressible nucleotide sequence to a controllable promoter capable of functioning in a host cell obtaining a first expression construct, iii) ligating at least one expressible nucleotide sequence to another independently controllable promoter capable of functioning in a host cell, obtaining a second expression construct, iv) inserting constructs of step ii) and iii) into at least two host cells, v) mixing at least two cells having a different combination of independently controllable promoter and expressible nucleotide sequences.

According to this aspect of the invention there is provided a convenient method for preparation of a library of individual cells comprising expressible nucleotide sequences under the operable control of at least two controllable promoters.

BRIEF DESCRIPTION OF THE DRAWINGS

FIG. 2 shows a flow chart of the steps leading from an entry library comprising expressible nucleotide sequences to evolvable artificial chromosomes (EVAC) transformed into an appropriate host cell.

| Lane | F/Y |
|------|-----|
| 1 | 100/1 |
| 2 | 50/1 |
| 3 | 20/1 |
| 4 | 10/1 |
| 5 | 5/1 |
| 6 | 2/1 |
| 7 | 1/1 |
| 8 | 1/2 |
| 9 | 1/5 |

Legend: Lane M: molecular weight marker, λ-phage DNA digested w. Pst1. Lanes 1-9, concatenation reactions. Ratio of fragments to yac-arms(F/Y) as in table.

Figure 9A:
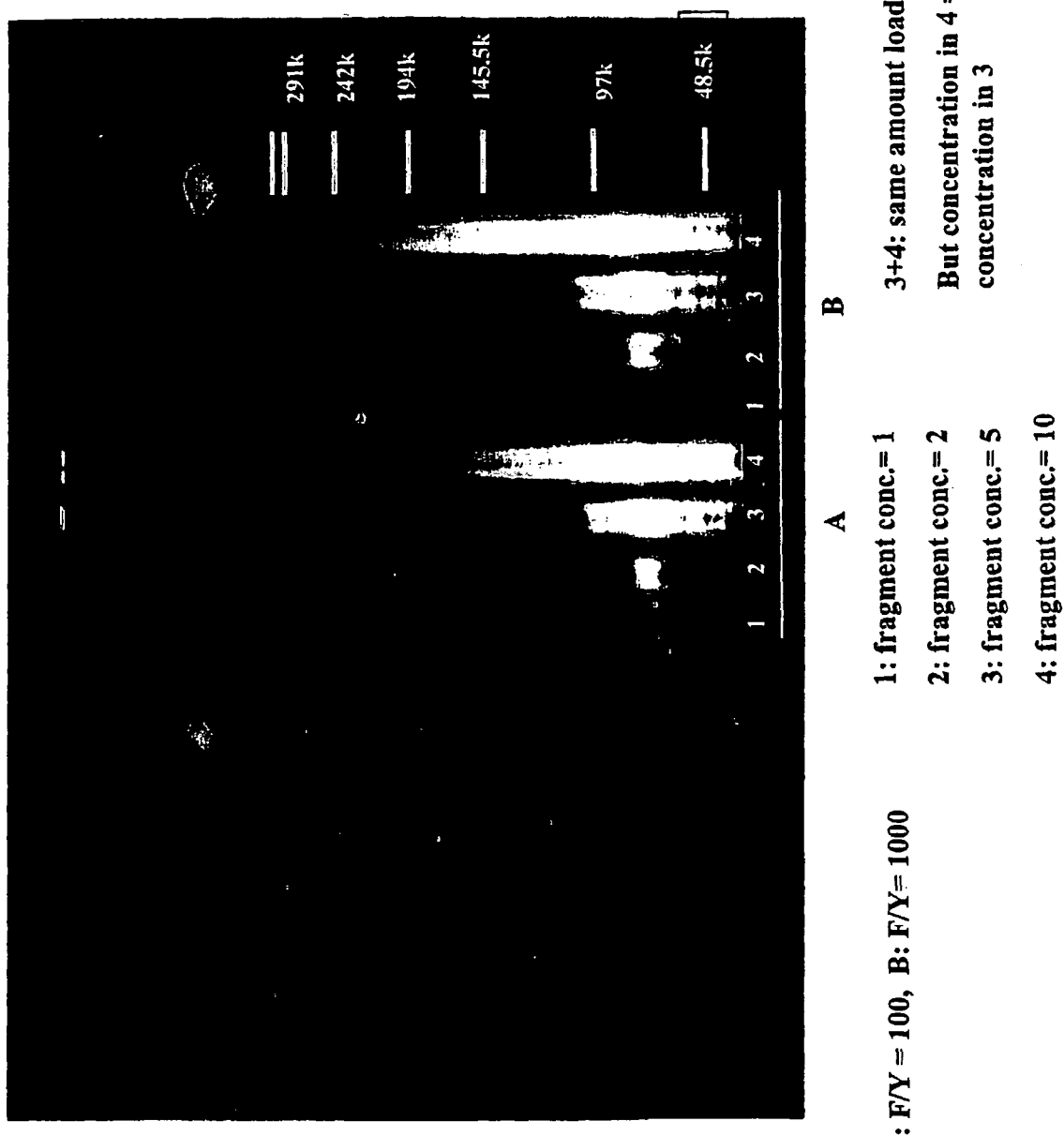
Figure 9B:
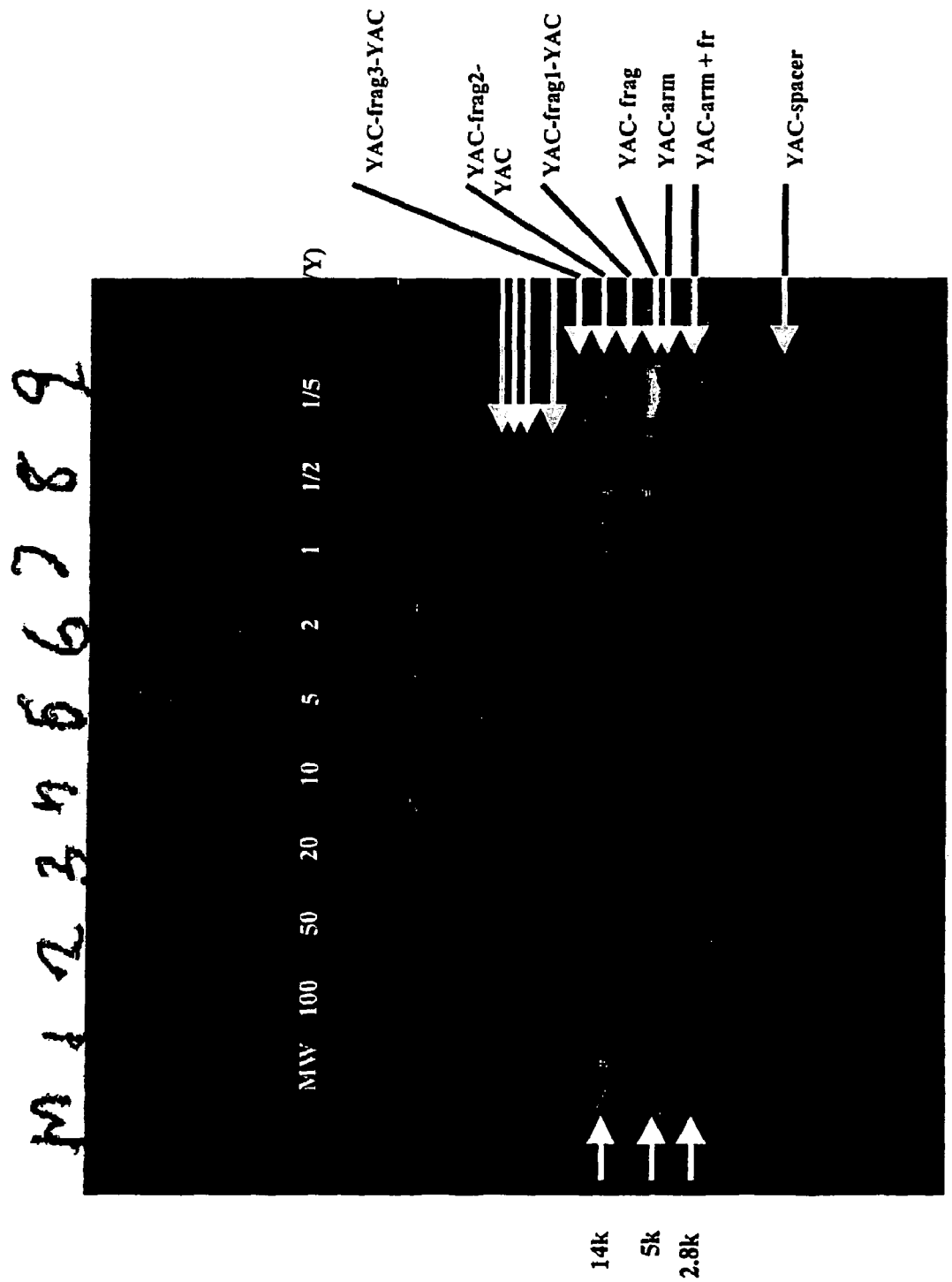

FIGS. 9*a* and 9*b*. illustrates the integration of concatenation with synthesis of evolvable artificial chromosomes and how concatemer size can be controlled by controlling the ratio of vector arms to expression cassettes, as described in example 7.

Figure 10:
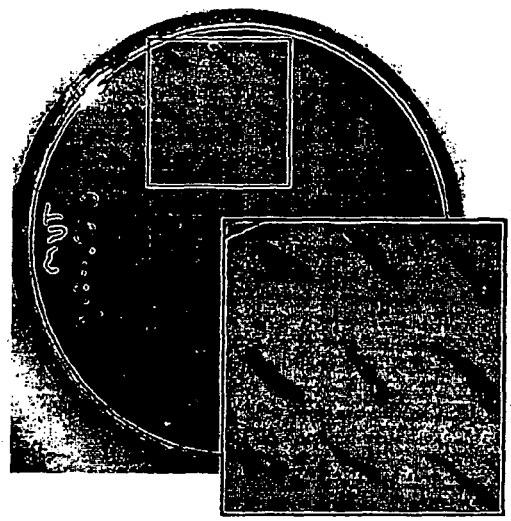
Figure 10:
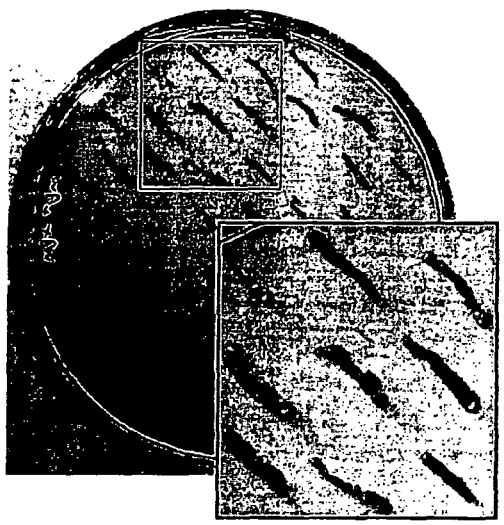
Figure 10:
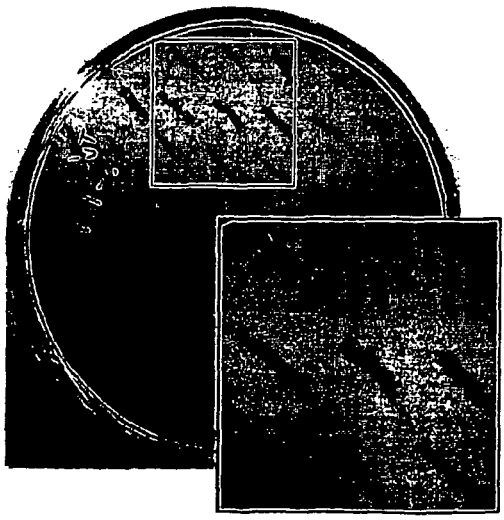
Figure 10:
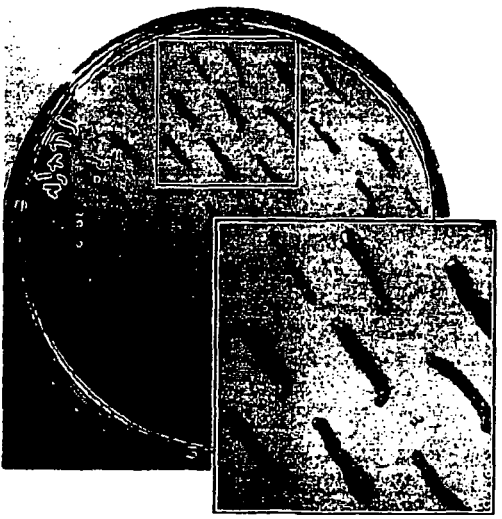

FIG. 10. Library of EVAC transformed population shown under 4 different growth conditions. Coloured phenotypes can be readily detected upon induction of the Met25 and/or the Cap1 promoters.

Figure 11:
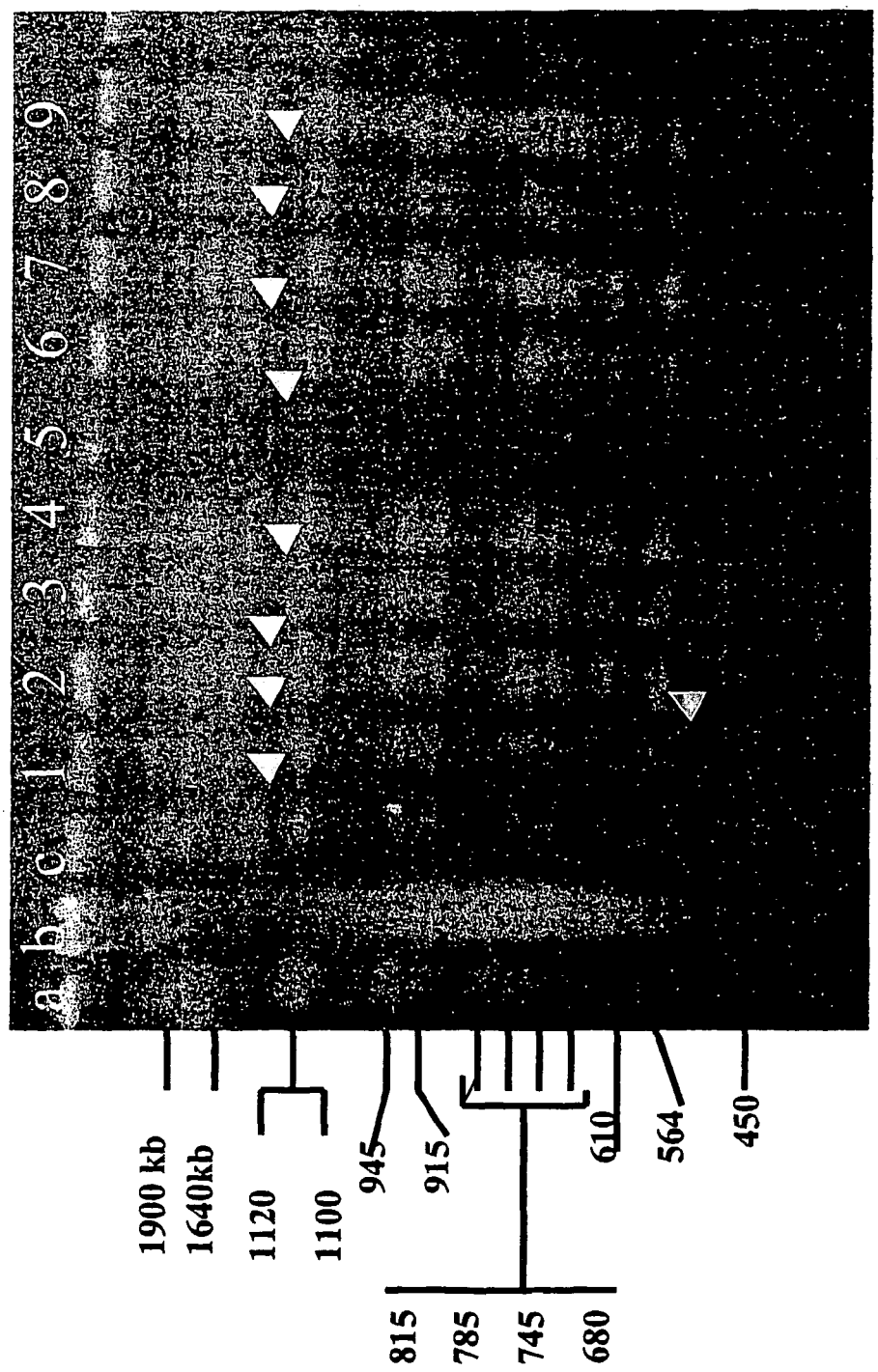

FIG. 11. EVAC gel Legend: PFGE of EVAC containing clones:

Lanes. a: Yeast DNA PFGE markers(strain YNN295), b: lambda ladder, c: non-transformed host yeast, 1-9: EVAC containing clones. EVACs in size range 1400-1600 kb. Lane 2 shows a clone containing 2 EVACs sized ~1500 kb and ~550 kb respectively. The 550 kb EVAC is comigrating with the 564 kb yeast chromosome and is resulting in an increased intensity of the band at 564 kb relative to the other bands in the lane. Arrows point up to EVAC bands.

DEFINITIONS

Unless defined otherwise, all technical and scientific terms used herein have the same meaning as is commonly understood by one of skill in the art to which this invention belongs.

As used herein, growth under selective conditions, means growth of a cell under conditions that require expression of a selectable marker for survival.

By a controllable promoter is meant a promoter, which can be controlled through external manipulations such as addition or removal of a compound from the surroundings of the cell, change of physical conditions, etc.

An independently controllable promoter may be induced/repressed substantially without affecting the induction/repression of other promoters according to the invention. The induction/repression of an independently controllable promoter may affect native promoters in the host cells.

Co-ordinated expression refers to the expression of a subset of genes which are induced or repressed by the same external stimulus.

Oligonucleotides

Any fragment of nucleic acids having approximately from 2 to 10000 nucleic acids.

Restriction Site

For the purposes of the present invention the abbreviation RSn (n=1,2,3, etc) is used to designate a nucleotide sequence comprising a restriction site. A restriction site is defined by a recognition sequence and a cleavage site. The cleavage site may be located within or outside the recognition sequence. The abbreviation "$rs_1$" or "$rs_2$" is used to designate the two ends of a restriction site after cleavage. The sequence "$rs_1$-$rs_2$" together designate a complete restriction site.

The cleavage site of a restriction site may leave a double stranded polynucleotide sequence with either blunt or sticky ends. Thus, "$rs_1$" or "$rs_2$" may designate either a blunt or a sticky end.

In the notation used throughout the present invention, formulae like:

RS1-RS2-SP-PR-X-TR-S P-RS2-RS1 should be interpreted to mean that the individual sequences follow in the order specified. This does not exclude that part of the recognition sequence of e.g. RS2 overlap with the spacer sequence, but it is a strict requirement that all the items except RS1 and RS1' are functional and remain functional after cleavage and re-assemblage. Furthermore the formulae do not exclude the possibility of having additional sequences inserted between the listed items. For example introns can be inserted as described in the invention below and further spacer sequences can be inserted between RS1 and RS2 and between TR and RS2. Important is that the sequences remain functional.

Furthermore, when reference is made to the size of the restriction site and/or to specific bases within it, only the bases in the recognition sequence are referred to.

Expression State

An expression state is a state in any specific tissue of any individual organism at any one time. Any change in conditions leading to changes in gene expression leads to another expression state. Different expression states are found in different individuals, in different species but they may also be found in different organs in the same species or individual, and in different tissue types in the same species or individual. Different expression states may also be obtained in the same organ or tissue in any one species or individual by exposing the tissues or organs to different environmental conditions comprising but not limited to changes in age, disease, infection, drought, humidity, salinity, exposure to xenobiotics, physiological effectors, temperature, pressure, pH, light, gaseous environment, chemicals such as toxins.

Artificial Chromosome

As used herein, an artificial chromosome (AC) is a piece of DNA that can stably replicate and segregate alongside endogenous chromosomes. For eukaryotes the artificial chromosome may also be described as a nucleotide sequence of substantial length comprising a functional centromer, functional telomeres, and at least one autonomous replicating sequence. It has the capacity to accommodate and express heterologous genes inserted therein. It is referred to as a mammalian artificial chromosome (MAC) when it contains an active mammalian centromere. Plant artificial chromosome and insect artificial chromosome (BUGAC) refer to chromosomes that include plant and insect centromers, respectively. A human artificial chromosome (HAC) refers to a chromosome that includes human centromeres, AVACs refer to avian artificial chromosomes. A yeast artificial chromosome (YAC) refers to chromosomes that are functional in yeast, such as chromosomes that include a yeast centromere.

As used herein, stable maintenance of chromosomes occurs when at least about 85%, preferably 90%, more preferably 95% of the cells retain the chromosome. Stability is measured in the presence of a selective agent. Preferably these chromosomes are also maintained in the absence of a selective agent. Stable chromosomes also retain their structure during cell culturing, suffering neither intrachromosomal nor interchromosomal rearrangements.

DETAILED DESCRIPTION OF THE INVENTION

The present invention relates to libraries of individual cells useful for capturing and preserving a diversity of genetic resources from nature, and for expressing the captured genetic resources and allowing them to interact to produce a diversity of chemical structures. The invention also facilitates screening for desirable properties and compounds.

More particularly, the invention provides methods for constructing and screening libraries of individual cells comprising heterologous expressible nucleotide sequences. These libraries comprise random assortments of expressible nucleotide sequences from multiple expression states and preferably also from multiple species the products of which are allowed to interact with each other in the expression host, and result in some cases in the formation of novel biochemical pathways and/or the production of novel classes of compounds. Moreover, the libraries of the invention provide efficient access to otherwise inaccessible sources of molecular diversity.

The novel biochemical pathways may carry out processes including but not limited to structural modification of a compound, addition of chemical groups to the compound, or decomposition of the compound.

The novel classes of compound may include but are not limited to metabolites, secondary metabolites, enzymes, or structural components of an organism. A compound of interest may have one or more potential therapeutic properties, including but not limited to agonist or antagonist to a class of receptor or a particular receptor, antibiotic, antiviral, antitumor, pharmacological or immunomodulating properties or be other commercially-valuable chemicals such as pigments.

A library of individual cells is a library comprising expression constructs prepared from randomly assembled or even concatenated expressible nucleotide sequences derived from a plurality of species of donor organisms, in which expressible nucleotide sequences are operably associated with regulatory regions that drives expression of the expressible nucleotide sequences in an appropriate host organism. The host organisms used are capable of producing functional gene products of the donor organisms. Upon expression in the host organism, gene products of the donor organism(s) may interact to form novel biochemical pathways.

Generally, the methods of the invention comprise providing expressible nucleotide sequences derived from one or more donor organism(s), engineering said expressible nucleotide sequences into a context where said expressible nucleotide sequences can be transcribed in a given host organism, and introducing said expressible nucleotide sequences into a host organism via a cloning or expression vector so that one or more expressible nucleotide sequences of the donor organism(s) are transferred to and expressed in the host organism. Such host organisms containing donor expressible nucleotide sequences are pooled to form a library.

The transferred genetic material, typically comprises a random assortment of expressible nucleotide sequences, the expression of which is driven and controlled by one or preferably by more functional regulatory regions. The expression construct or vector advantageously provide these regulatory regions. The expressible nucleotide sequences of the donor organism(s) are transcribed, translated and processed in the host organism to produce functional proteins that in turn generate the metabolites of interest.

Once a desirable activity or compound is identified, downstream drug development efforts such as strain improvement and process development, are greatly facilitated. The positive clone can be cultured under standard conditions to produce the desired compound in substantial amounts for further studies or uses. The expressible nucleotide sequences of the biochemical pathway are immediately available for sequencing, mutation, expression, and further rounds of screening. The cloned biochemical pathway is readily amenable to traditional and/or genetic manipulations for overproduction of the desired compound.

Furthermore, according to the embodiments comprising the expression cassettes with common structure, several positive cells may be identified, their expression cassettes be excised due to the presence of a common restriction site, which is preferably a rare restriction site. The excised expression cassettes may be re-assembled in a random or targeted manner to produce novel combinations of the selected expression cassettes.

Furthermore, biochemical pathways that are otherwise silent or undetectable in the donor organism may be discovered more easily by virtue of their functional reconstitution in the host organism. Since the biochemical characteristics of the host organism are well known, many deviations as a result of expression of donor genetic material can readily be recognised. Novel compounds may be detected by comparing extracts of a host organism containing donor genetic material against a profile of compounds known to be produced by the control host organism under a given set of environmental conditions. Even very low levels of a desirable activity or compound may be detected when the host biochemical and cellular background of the host organism is well characterised.

In one embodiment, the methods may be applied to donor organism(s) that cannot be recovered in substantial amounts in nature, or cultured in the laboratory. By transferring genetic material such as cDNA from such organisms into a host organism, the organisms' metabolic pathways may be reproduced, and their, products tested efficiently for any desirable properties. Thus, the genetic diversity of these organisms is captured and preserved and combined with the genetic diversity of other organisms.

In another embodiment of the invention, a library can be constructed in which the expressible nucleotide sequences from one or multiple donor organisms are randomly concatenated prior to introduction into the host organism. Thus, each host organism in the library may individually contain a unique, random combination of expressible nucleotide sequences derived from the various donor pathways or organisms. For the most part, such combinations of expressible nucleotide sequences in the library do not occur in nature. Upon expression, the functional gene products of the various donor pathways or organisms interact with each other and with the native host complement of gene products in individual host organisms to generate combinations of biochemical reactions which result in novel metabolic pathways and/or production of novel compounds. Collectively, the genetic resources of the donor organisms in the library are translated into a diversity of chemical compounds that may not be found in individual donor organisms.

In another aspect of the invention, the methods may be applied to the generation of a multiple kingdom pathway in the host organism. An example of this would be the introduction of genes from carotenoid pathways (obtained from fungi, algae and/or plants) as well as genes from synthesis of Vitamin A (obtained from animals) or genes coding for the production of visual pigments (obtained from insects). By such targeted selection and combination of elements of biochemical pathways across kingdoms the likelihood of obtaining novel metabolites may be further increased.

In another aspect of the invention, the species of donor organisms may be selected on the basis of their biological characteristics. Such biological characteristics may include, but are not limited to the capability to utilise certain nutrients, to survive under extreme conditions, to derivatise a chemical structure, and the ability to break down or catalyse formation of certain types of chemical linkages. When expressible nucleotide sequences of the donor organism are expressed in the host organism, the donor gene products can modify and/or substitute the functions of host gene products that constitute host metabolic pathways, thereby generating novel hybrid pathways. Novel activities and/or compounds may be produced by hybrid pathways comprising donor and host-derived components. The target metabolic pathway modified by donor gene products may be native to the host organism. Alternatively, the target metabolic pathway may be provided by products of heterologous genes which are endogenous or have been genetically engineered into every host organism prior to or contemporaneous to construction of the gene expression library. Thus, the present invention also embodies constructing and screening gene expression libraries, wherein DNA fragments encoding metabolic pathway of donor organisms are cloned and coexpressed in host organisms containing a target metabolic pathway.

In another embodiment of the invention, the host organism may have an enhanced complement of active drug efflux systems which secretes the compounds of interest into the culture medium, thus reducing the toxicity of the compounds to the host organism. Absorptive material, e.g., neutral resins, may be used during culturing of the host organisms, whereby metabolites produced and secreted by the host organism may be sequestered, thus facilitating recovery of the metabolites.

In many respects, the libraries provides significant convenience and time advantage to the various steps of development of novel small molecules such as the development of drugs up to clinical trials. The libraries of the invention are compatible with e.g. the established multi-well footprint format and robotics for high-throughput screening. The host organisms of the invention are organisms commonly used for genetic manipulation and/or process development. The present invention takes advantage of the fact that such host organisms or production hosts are well-characterised in terms of their biological properties and maintenance requirements. By transferring genetic materials from a donor organism to other more familiar expression systems, the need for difficult culturing conditions for the donor organism is reduced. Thus, the biological activities, the pharmacokinetic and toxic properties of any lead compound discovered in the system of the invention may be studied and optimised more efficiently.

The novel metabolic pathway generated in a positive clone can be delineated by standard techniques in molecular biology. The lead compound may be synthesised by culturing a clone of the drug-producing host organism under standard or empirically determined culture conditions, so that sufficient quantities of the lead compound may be isolated for further analysis and development. There are already high purity manufacturing protocols, such as Good Manufacturing Practice (GMP) established for some of these standard industrial host organisms. Unlike conventional methods of screening natural product sources, less effort is required to adapt the screening and production technologies to the particular requirements of each potentially drug-producing organism.

The present invention also provides libraries made according to the methods of the invention from genetic materials of a particular set of donor organisms and/or cell types. Not all organisms or cell types in a set, especially mixed samples, need to be individually identified or characterised to enable preparation of the libraries.

Any library of the invention may be amplified, replicated, and stored. Amplification is preferably performed by introducing entry vectors containing expressible nucleotide sequences in a initial host organism such as *E. coli* so that so that multiple clones of the expressible nucleotide sequences are produced. Replication refers to picking and growing of individual clones in the library. A library of the invention may be stored and retrieved by any techniques known in the art that is appropriate for the host organism. Thus, the libraries of the invention are an effective means of capturing and preserving the genetic resources of donor organisms, which may be accessed repeatedly in a drug discovery program or other discovery programs.

Concatemer Assemblage

Concatemers may be assembled from cDNA libraries on a routine basis. A typical concatemer generation step will pool e.g. 1,000 genes=cDNA expression constructs (from 1 sample) and use this to generate 1,000 concatemers, with an average of 25 genes per concatemer. This means on average each gene will be in 25 different concatemers within a pool. One such concatemer "Source Pool" may be generated per source cDNA library. The Source Pools are suitable for storage of the concatemers.

However, the invention is not limited to any specific number of genes in a source pool. Concatemers with approximately 500 genes are easily produced and it is contemplated that this number can be increased even further.

The actual numbers depend on the number of different promoters and/or spacers and/or terminators to be incorporated —i.e. if an expression state gives 1000 different cDNAs and these are to be combined with 2 promoters and/or spacers and/or terminators the numbers increase proportionally: 1000 cDNAs=2000 expression constructs, so if each construct should still be present in 25 concatemers of 25 constructs then the source pool size would be 2000.

Certain Source Pools may in fact be generated on a function rather than species basis. Such a source pool may for example be based on sources known for a specific property, such as carotenoid activity, pharmaceutical properties, chemotaxonomic properties, etc.

Host Library Assemblage

Source Pools may be mixed and used to generate host libraries or screening libraries with each host containing multiple concatemers In selecting which Source Pools to mix one may use knowledge of the source of given libraries, host pathways, the desired focus of particular programmes and success rates of given libraries in particular screens.

If each source library is constructed from 1,000 different genes and assembled into EVACs each containing 25 genes, then for any one given gene, of those EVACs that do contain the gene, 98.8% of them will contain just one copy, 1.2% will contain 2 copies and 0.01% will contain 3 or more copies. Thus for all practical purposes each EVAC can in this situaton be regarded as composed of 25 different genes. Should a cell population be created from four such source libraries, then each different gene (assuming no overlap between genes from different sources) will be represented at a frequency of 1 copy per 4,000 genes.

In a cell population where each cell contains four EVACS, generated from a pool of 4 source libraries, then in respect of any one of the source libraries, statistically:

0.4% of cells will have all four of their EVACS from this source 4.3% of cells will have three out of four EVACS from this source 25.5% of cells will have two EVACS from this source 38.3% of cells will have just one EVAC from this source 31.6% of cells will not contain any EVACs from this source From these figures the probability of any two-gene combination can be calculated using standard statistical tools For more focused evolutionary approaches, such as the evolution of novel carotenoids or other known structural classes or metabolite pathways, EVACs can be enriched for enzymes, and homologs or functional analogs of these enzymes, that conduct different stages of the metabolic pathway. Such an approach can lead to significant probabilities that essentially all steps of a given pathway are represented, at least at the transcription level, in a cell. Thus if a 10-step pathway is required, and 50-gene EVACS are constructed randomly from genes encoding for homologous or analogous enzymes to those responsible for each step then any given step will be encoded in >85% of EVACs between 3-9 times (inclusive) and will be entirely missing in just 0.52% of EVACs. Thus it can be seen that a $10^8$ member cell population where each cell contains 4 EVACs of 50 genes each, constructed from 4 enzyme encoding gene pools, will contain a large number of cells in which all steps of the potential pathway are represented, in most cases multiple times.

Sub-libraries

Initial screens are designed to sort host lines into "collections", sub-libraries, based on whether novel activity has been induced by the concatemers, and the type of activity that has been induced. As such initial screens should be reasonably high throughput and should be arbitrary in their selection criteria.

A large number of such screens can be considered. An illustrative example of such screens may include but are not limited to:

Novel spectral properties

Induced cytochrome oxidase activity

Changed size, morphology, stickiness or adhesive properties or lack thereof

Ability to grow on substrates they cannot normally grow on

Ability to grow on sublethal substrates

Ability to grow in the absence of normal essential requirements

Ability to grow on media comprising one or more inhibitors

Ability to grow under changed physical conditions, such as temperature, osmolarity, electromagnetic radiation including light of certain wavelengths.

Ability to grow under magnetic field of certain force.

Secretion or the lack of it from the cell

The inhibition or prevention of inhibition of an enzyme

The activation of a receptor.

The prevention of an activating molecule binding to a receptor.

The inhibition or promotion of binding of small molecules or proteins to nucleic acid or peptide sequences.

The inhibition or promotion of transcription or translation of post translational processing.

Changes in the transport or localisation of molecules within the cell or within organelles.

Changes in the DNA content or morphology of the cell.

The production of small molecules with certain properties that allow their selective isolation (e.g. all the chromoatography principles available to the skilled practitioner).

The production of small molecules with certain spectroscopic properties (defined broadly to include visible light, microwaves, IR, UV, X-ray, etc.).

Changes in the morphology of the cell, including the prevention or promotion of cell differentiation;

The induction of apoptotic pathways.

For each Host Library (of 10,000 host lines) the 1-2% of host lines that are most extreme on each of such criteria may be grouped into a sub-library. These initial sorting screens will in general be conducted under conditions that maximise the number of genes expressed per concatemer.

The output of a sorting screen may be host lines that are characterised on one or more broad criteria. These may be categorised as sub-libraries.

A sub-library may be defined with reference to a common phenotype of the cells in the sub-library. But a sublibrary may also be defined as a collection of individual cells, said cells having—for at least one identical expressible DNA sequence—different promotors, i.e. with reference to the presence of specific expressible nucleotide sequences. Furthermore, a sub-library may be described with reference to a cassette and/or in a concatemer of cassettes comprised in the host cells. A sub-library may thus be defined as a collection of individual cells, each cell having—in at least one cassette of the concatemer—identical expressible DNA sequences. A sublibrary may also be looked upon as a collection of individual cells, said cells having—for at least one identical expressible DNA sequence, more preferably for substantially all identical expressible nucleotide sequences—different promoters.

The common phenotype of a given sub-library may be at least one phenotype selected from the group comprising the ability to grow on unusual substrates, the ability to grow on sublethal concentration of toxins, the ability to grow at a high temperature, the ability to grow at a low temperature, the ability to grow at elevated osmolality, the ability to grow at low osmolality, the ability to grow at high salinity, the ability to grow at low salinity, the ability to grow at elevated metal concentrations, the ability to grow at high $CO_2$ concentrations, the ability to grow at low $CO_2$ concentrations the ability to grow at high $O_2$ concentrations, the ability to grow at low $O_2$ concentrations, the ability to provide special spectral properties, the ability to provide a special colour, the ability to have a deviating GST activity, the ability to have a deviating P450 activity.

Size of Library

A library of cells may in principle comprise just two cells differing with respect to one of the features discussed below. However, normally a library comprises at least 20 individual cells, such as at least 50 individual cells. More preferably, a library comprises at least 100 individual cells, such as at least 1,000 cells, for example at least 10,000 cells such as at least 100,000 cells, for example at least.1,000,000 cells, such as at least 1,000,000,000 cells.

The number of cells in a sub-library depends on the selection criterion or criteria used. At the beginning a sub-library typically comprises less cells than a library, but the cells of the sub-library may be combined or allowed to sexually propagate to produce increased variation and in this way the number of different cells in a sub-library may increase.

Variation Among Cells

The difference between cells in a library may be defined with reference to differences between expression cassettes, between concatemers or differences between promoters controlling the expression of an expressible nucleotide sequence.

Thus in a library according to the invention a concatemer of each cell may comprise at least a first cassette and a second cassette, said first cassette being different from said second cassette. More preferably substantially all cassettes of a concatemer in a given cell are different.

The difference between the expression cassettes, which may be reflected in the difference between concatemers in different cells may be a difference in the spacer sequences and/or the promoter, and/or the expressible nucleotide sequence and/or the intron and/or terminator sequence.

When the differences lie in the expressible nucleotide sequences these different expressible nucleotide sequences may come from the same or from different expression states. The different expression states may represent at least two different tissues, such as at least two organs, such as at least two species, such as at least two genera. The different species are from at least two different phylae, such as from at least two different classes, such as from at least two different divisions, more preferably from at least two different sub-kingdoms, such as from at least two different kingdoms. In this way cells and libraries representing an extremely wide array of gene combinations is obtained.

Preferably substantially all cells in a library are different. This increases the number of available combinations of expressible nucleotide sequences. Further variation may be obtained by having one library in cells of one mating type and another library in cells of another mating type. For yeast this may be obtained by having one library in Mata cells and another library in Matα cells. These may then be sexually crossed to obtain further variation.

According to an especially preferred embodiment of the invention the library comprises a random combination of promoter and expressible nucleotide sequences made from a two dimensional array of promoters and heterologous expressible nucleotide sequences. Thereby, it is possible to get—in principle—all expressible nucleotide sequences from a given pool represented in a library under the control of different promoters.

When each cell furthermore comprises an individual selection of combinations of promoters and heterologous expressible nucleotide sequences drawn individually from the same pool of promoters and heterologous expressible nucleotide sequences completely random combinations of promoter and expressible nucleotide sequences are inserted into all cells. Each expressible nucleotide sequence may then be found in the library under the control of different promoters and in a number of combinations with a number of other expressible nucleotide sequences.

Each library may comprise at least 2 different independently controllable promoters, such as at least 3, for example at least 4, such as at least 5, for example at least 6, such as at least 7, for example at least 8, such as at least 9, for example at least 10, such as at least 15, for example at least 25, such as at least 50, for example at least 75, such as at least 100. The higher the number of promoters in the library, the number of sub-sets of genes may be constructed within any one cell and within any one library. Preferably the regulation of the promoters should not interact on each other. The absence of interaction sets an upper limit to the number of promoters that can be used under practical circumstances. However, new promoters are discovered and synthetic promoters are being developed continuously so it is likely that in the future combinations of different non-interacting promoters can be made.

At least one heterologous expressible nucleotide sequence may be found in at least 2 cells, such as at least 3 cells, for example at least 5 cells, such as at least 10 cells, for example at least 25 cell, such as at least 50 cells, for example at least 100 cells, such as at least 500 cells, for example at least 1000 cells. By having the same expressible nucleotide represented in several preferably in many cells, any one expressible nucleotide sequence may be found in many combinations with different expressible nucleotide sequences.

The combination of promoter and expressible nucleotide sequences in any one cell may be laid out so that at least one cell comprises a group of heterologous expressible nucleotide sequences under the control of a first promoter, the group comprising at least 5 heterologous expressible nucleotide sequences, such as at least 10 heterologous expressible nucleotide sequences, for example at least 15 heterologous expressible nucleotide sequences, such as at least 25 heterologous expressible nucleotide sequences, for example at least 50 heterologous expressible nucleotide sequences, such as at least 75 heterologous expressible nucleotide sequences, for example at least 100 heterologous expressible nucleotide sequences, such as at least 250 heterologous expressible nucleotide sequences, for example at least 500 heterologous expressible nucleotide sequences. Thereby a sub-set of expressible nucleotide sequences of different size can be turned on and off in the cells.

By furthermore having in a cell at least a second group of heterologous expressible nucleotide sequences under the independent control of second promoter, such as at least a third group of heterologous expressible nucleotide sequences under the independent control of a third promoter, for example at least a fourth group of heterologous expressible nucleotide sequences under the independent control of a fourth promoter, such as at least a fifth group of heterologous expressible nucleotide sequences under the independent control of a fifth promoter, for example at least a sixth group of heterologous expressible nucleotide sequences under the independent control of a sixth promoter, such as at least a seventh group of heterologous expressible nucleotide sequences under the independent control of a seventh promoter, such as at least a eighth group of heterologous expressible nucleotide sequences under the independent control of a eighth promoter, for example at least a ninth group of heterologous expressible nucleotide sequences under the independent control of a ninth promoter, such as at least a tenth group of heterologous expressible nucleotide sequences under the independent control of a tenth promoter, groups of expressible nucleotide sequences, sub-sets, may be turned on and off in the cells.

Origin of Expressible Nucleotide Sequences

The expressible nucleotide sequences that can be inserted into the vectors, concatemers, and cells according to this invention encompass any type of nucleotide such as RNA, DNA. Such a nucleotide sequence could be obtained e.g. from cDNA, which by its nature is expressible. But it is also possible to use sequences of genomic DNA, coding for specific genes. Preferably, the expressible nucleotide sequences correspond to full length genes such as substantially full length cDNA, but nucleotide sequences coding for shorter peptides than the original full length mRNAs may also be used. Shorter peptides may still retain the catalytic activity similar to that of the native proteins.

Another way to obtain expressible nucleotide sequences is through chemical synthesis of nucleotide sequences coding for known peptide or protein sequences. Thus the expressible DNA sequences does not have to be a naturally occurring sequence, although it may be preferable for practical purposes to primarily use naturally occurring nucleotide sequences. Whether the DNA is single or double stranded will depend on the vector system used.

In most cases the orientation with respect to the promoter of an expressible nucleotide sequence will be such that the coding strand is transcribed into a proper mRNA. It is however conceivable that the sequence may be reversed generating an antisense transcript in order to block expression of a specific gene.

Cassettes

An important aspect of the invention concerns a cassette of nucleotides in a highly ordered sequence, the cassette having the general formula in 5'→3' direction:

[RS1-RS2-SP-PR-CS-TR-SP-RS2'-RS1']

wherein RS1 and RS1' denote restriction sites, RS2 and RS2' denote restriction sites different from RS1 and RS1', SP individually denotes a spacer sequence of at least two nucleotides, PR denotes a promoter, CS denotes a cloning site, and TR denotes a terminator.

It is an advantage to have two different restriction sites flanking both sides of the expression construct. By treating the primary vectors with restriction enzymes cleaving both restriction sites, the expression construct and the primary vector will be left with two non-compatible ends. This facilitates a concatenation process, since the empty vectors do not participate in the concatenation of expression constructs.

Restriction Sites

In principle, any restriction site, for which a restriction enzyme is known can be used. These include the restriction enzymes generally known and used in the field of molecular biology such as those described in Sambrook, Fritsch, Maniatis, "A laboratory Manual", $2^{nd}$ edition. Cold Spring Harbor Laboratory Press, 1989.

The restriction site recognition sequences preferably are of a substantial length, so that the likelihood of occurrence of an identical restriction site within the cloned oligonucleotide is minimised. Thus the first restriction site may comprise at least 6 bases, but more preferably the recognition sequence comprises at least 7 or 8 bases. Restriction sites having 7 or more non N bases in the recognition sequence are generally known as "rare restriction sites" (see example 6). However, the recognition sequence may also be at least 10 bases, such as at least 15 bases, for example at least 16 bases, such as at least 17 bases, for example at least 18 bases, such as at least 18 bases, for example at least 19 bases, for example at least 20 bases, such as at least 21 bases, for example at least 22 bases, such as at least 23 bases, for example at least 25 bases, such as at least 30 bases, for example at least 35 bases, such as at least 40 bases, for example at least 45 bases, such as at least 50 bases.

Preferably the first restriction site RS1 and RS1' is recognised by a restriction enzyme generating blunt ends of the double stranded nucleotide sequences. By generating blunt ends at this site, the risk that the vector participates in a subsequent concatenation is greatly reduced. The first restriction site may also give rise to sticky ends, but these are then preferably non-compatible with the sticky ends resulting from the second restriction site, RS2 and RS2' and with the sticky ends in the AC.

According to a preferred embodiment of the invention, the second restriction site, RS2 and RS2' comprises a rare restriction site. Thus, the longer the recognition sequence of the rare restriction site the more rare it is and the less likely is it that the restriction enzyme recognising it will cleave the nucleotide sequence at other—undesired—positions. The rare restriction site may furthermore serve as a PCR priming site. Thereby it is possible to copy the cassettes via PCR techniques and thus indirectly "excise" the cassettes from a vector.

Spacer Sequence

The spacer sequence located between the RS2 and the PR sequence is preferably a non-transcribed spacer sequence. The purpose of the spacer sequence(s) is to minimise recombination between different concatemers present in the same cell or between cassettes present in the same concatemer, but it may also serve the purpose of making the nucleotide sequences in the cassettes more "host" like. A further purpose of the spacer sequence is to reduce the occurrence of hairpin formation between adjacent palindromic sequences, which may occur when cassettes are assembled head to head or tail to tail. Spacer sequences may also be convenient for introducing short conserved nucleotide sequences that may serve e.g. as PCR primer sites or as target for hybridization to e.g. nucleic acid or PNA or LNA probes allowing affinity purification of cassettes.

The cassette may also optionally comprise another spacer sequence of at least two nucleotides between TR and RS2. When cassettes are cut out from a vector and concatenated into concatemers of cassettes, the spacer sequences together ensure that there is a certain distance between two successive identical promoter and/or terminator sequences. This distance may comprise at least 50 bases, such as at least 60 bases, for example at least 75 bases, such as at least 100 bases, for example at least 150 bases, such as at least 200 bases, for example at least 250 bases, such as at least 300 bases, for example at least 400 bases, for example at least 500 bases, such as at least 750 bases, for example at least 1000 bases, such as at least 1100 bases, for example at least 1200 bases, such as at least 1300 bases, for example at least 1400 bases, such as at least 1500 bases, for example at least 1600 bases, such as at least 1700 bases, for example at least 1800 bases, such as at least 1900 bases, for example at least 2000 bases, such as at least 2100 bases, for example at least 2200 bases, such as at least 2300 bases, for example at least 2400 bases, such as at least 2500 bases, for example at least 2600 bases, such as at least 2700 bases, for example at least 2800 bases, such as at least 2900 bases, for example at least 3000 bases, such as at least 3200 bases, for example at least 3500 bases, such as at least 3800 bases, for example at least 4000 bases, such as at least 4500 bases, for example at least 5000 bases, such as at least 6000 bases.

The number of the nucleotides between the spacer located 5' to the PR sequence and the one located 3' to the TR sequence may be any. However, it may be advantageous to ensure that at least one of the spacer sequences comprises between 100 and 2500 bases, preferably between 200 and 2300 bases, more preferably between 300 and 2100 bases, such as between 400 and 1900 bases, more preferably between 500 and 1700 bases, such as between 600 and 1500 bases, more preferably between 700 and 1400 bases.

If the intended host cell is yeast, the spacers present in a concatemer should preferably comprise a combination of a few ARSes with varying lambda phage DNA fragments.

Preferred examples of spacer sequences include but are not limited to: Lamda phage DNA, prokaryotic genomic DNA such as *E. coli* genomic DNA, ARSes.

Promoter

A promoter is a DNA sequence to which RNA polymerase binds and initiates transcription. The promoter determines the polarity of the transcript by specifying which strand will be transcribed.

Bacterial promoters normally consist of –35 and –10 (relative to the transcriptional start) consensus sequences which are bound by a specific sigma factor and RNA polymerase.

Eukaryotic promoters are more complex. Most promoters utilized in expression vectors are transcribed by RNA polymerase II. General transcription factors (GTFs) first bind specific sequences near the transcriptional start and then recruit the binding of RNA polymerase II. In addition to these minimal promoter elements, small sequence elements are recognized specifically by modular DNA-binding/trans-activating proteins (e.g. AP-1, SP-1) which regulate the activity of a given promoter.

Viral promoters may serve the same function as bacterial and eukaryotic promoters. Upon viral infection of their host, viral promoters direct transcription either by using host transcriptional machinery or by supplying virally encoded enzymes to substitute part of the host machinery. Viral promoters are recognised by the transcriptional machinery of a large number of host organisms and are therefore often used in cloning and expression vectors.

Promoters may furthermore comprise regulatory elements, which are DNA sequence elements which act in conjunction with promoters and bind either repressors (e.g., lacO/LAC Iq repressor system in *E. coli*) or inducers (e.g., gal1/GAL4 inducer system in yeast). In either case, transcription is virtually "shut off" until the promoter is derepressed or induced, at which point transcription is "turned-on". The choice of promoter in the cassette is primarily dependent on the host organism into which the cassette is intended to be inserted. An important requirement to this end is that the promoter should preferably be capable of functioning in the host cell, in which the expressible nucleotide sequence is to be expressed.

Preferably the promoter is an externally controllable promoter, such as an inducible promoter and/or a repressible promoter. The promoter may be either controllable (repressible/inducible) by chemicals such as the absence/presence of chemical inducers, e.g. metabolites, substrates, metals, hormones, sugars. The promoter may likewise be controllable by certain physical parameters such as temperature, pH, redox status, growth stage, developmental stage, or the promoter may be inducible/repressible by a synthetic inducer/repressor such as the gal inducer.

In order to avoid unintentional interference with the gene regulation systems of the host cell, and in order to improve controllability of the coordinated gene expression the promoter is preferably a synthetic promoter. Suitable promoters are described in U.S. Pat. Nos. 5,798,227, 5,667,986. Principles for-designing suitable synthetic eukaryotic promoters are disclosed in U.S. Pat. Nos. 5,559,027, 5,877,018 or 6,072,050.

Synthetic inducible eukaryotic promoters for the regulation of transcription of a gene may achieve improved levels of protein expression and lower basal levels of gene expression. Such promoters preferably contain at least two different classes of regulatory elements, usually by modification of a native promoter containing one of the inducible elements by inserting the other of the inducible elements. For example, additional metal responsive elements IR:Es) and/or glucocorticoid responsive elements (GREs) may be provided to native promoters. Additionally, one or more constitutive elements may be functionally disabled to provide the lower basal levels of gene expression.

Preferred examples of promoters include but is not limited to those promoters being induced and/or repressed by any factor selected from the group comprising carbohydrates, e.g. galactose; low inorganic phosphase levels; temperature, e.g. low or high temperature shift; metals or metal ions, e.g. copper ions; hormones, e.g. dihydrotestosterone; deoxycorticosterone; heat shock (e.g. 39° C.); methanol; redox-status; growth stage, e.g. developmental stage; synthetic inducers, e.g. gal inducer. Examples of such promoters include ADH 1, PGK 1, GAP 491, TPI, PYK, ENO, PMA 1, PHO5, GAL 1, GAL 2, GAL 10, MET25, ADH2, MEL 1, CUP 1, HSE, AOX, MOX, SV40, CaMV, Opaque-2, GRE, ARE, PGK/ARE hybrid, CYC/GRE hybrid, TPI/α2 operator, AOX 1, MOX A.

More preferably, however the promoter is selected from hybrid promoters such as PGK/ARE hybrid, CYC/GRE hybrid or from synthetic promoters. Such promoters can be controlled without interfering too much with the regulation of native genes in the expression host.

Yeast Promoters

In the following, examples of known yeast promoters that may be used in conjunction with the present invention are shown. The examples are by no way limiting and only serve to indicate to the skilled practitioner how to select or design promoters that are useful according to the present invention.

Although numerous transcriptional promoters which are functional in yeasts have been described in the literature, only some of them have proved effective for the production of polypeptides by the recombinant route. There may be mentioned in particular the promoters of the PGK genes (3-phosphoglycerate kinase, TDH genes encoding GAPDH (Glyceraldehyde phosphate dehydrogenase), TEF1 genes (Elongation factor 1), MFα1 (α sex pheromone precursor) which are considered as strong constitutive promoters or alternatively the regulatable promoter CYCI which is repressed in the presence of glucose or PHO5 which can be regulated by thiamine. However, for reasons which are often unexplained, they do not always allow the effective expression of the genes which they control. In this context, it is always advantageous to be able to have new promoters in order to generate new effective host/vector systems. Furthermore, having a choice of effective promoters in a given cell also makes it possible to envisage the production of multiple proteins in this same cell (for example several enzymes of the same metabolic chain) while avoiding the problems of recombination between homologous sequences.

In general, a promoter region is situated in the 5' region of the genes and comprises all the elements allowing the, transcription of a DNA fragment placed under their control, in particular:

(1) a so-called minimal promoter region comprising the TATA box and the site of initiation of transcription, which determines the position of the site of initiation as well as the basal level of transcription. In Saccharomyces cerevisiae, the length of the minimal promoter region is relatively variable. Indeed, the exact location of the TATA box varies from one gene to another and may be situated from −40 to −120 nucleotides upstream of the site of the initiation (Chen and Struhl, 1985, EMBO J., 4, 3273-3280)

(2) sequences situated upstream of the TATA box (immediately upstream up to several hundreds of nucleotides) which make it possible to ensure an effective level of transcription either constitutively (relatively constant level of transcription all along the cell cycle, regardless of the conditions of culture) or in a regulatable manner (activation of transcription in the presence of an activator and/or repression in the presence of a repressor). These sequences, may be of several types: activator, inhibitor, enhancer, inducer, repressor and may respond to cellular factors or varied culture conditions.

Examples of such promoters are the ZZA1 and ZZA2 promoters disclosed in U.S. Pat. No. 5,641,661, the EF1-α protein promoter and the ribosomal protein S7 gene promoter disclosed in WO 97/44470, the COX 4 promoter and two unknown promoters (SEQ ID No: 1 and 2 in the document) disclosed in U.S. Pat. No. 5,952,195. Other useful promoters include the HSP150 promoter disclosed in WO 98/54339 and the SV40 and RSV promoters disclosed in U.S. Pat. No. 4,870,013 as well as the PyK and GAPDH promoters disclosed in EP 0 329 203 A1.

Synthetic Yeast Promoters

More preferably the invention employs the use of synthetic promoters. Synthetic promoters are often constructed by combining the minimal promoter region of one gene with the upstream regulating sequences of another gene. Enhanced promoter control may be obtained by modifying specific sequences in the upstream regulating sequences, e.g. through substitution or deletion or through inserting multiple copies of specific regulating sequences. One advantage of using synthetic promoters is that they may be controlled without interfering too much with the native promoters of the host cell.

One such synthetic yeast promoter comprises promoters or promoter elements of two different yeast-derived genes, yeast killer toxin leader peptide; and amino terminus of IL-1β (WO 98/54339).

Another example of a yeast synthetic promoter is disclosed in U.S. Pat. No. 5,436,136 (Hinnen et al), which concerns a yeast hybrid promoter including a 5' upstream promoter element comprising upstream activation site(s) of the yeast PHO5 gene and a 3' downstream promoter element of the yeast GAPDH gene starting at nucleotide −300 to −180 and ending at nucleotide −1 of the GAPDH gene.

Another example of a yeast synthetic promoter is disclosed in U.S. Pat. No. 5,089,398 (Rosenberg et al). This disclosure describes a promoter with the general formula- (P.R.(2)-P.R.(1))- wherein:

P.R.(1) is the promoter region proximal to the coding sequence and having the transcription initiation site, the RNA polymerase binding site, and including the TATA box, the CMT sequence, as well as translational regulatory signals, e.g., capping sequence, as appropriate;

P.R.(2) is the promoter region joined to the. 5'-end of P.R. (1) associated with enhancing the efficiency of transcription of the RNA polymerase binding region;

In U.S. Pat. No. 4,945,046 (Horii et al) discloses a further example of how to design a synthetic yeast promoter. This specific promoter comprises promoter elements derived both from yeast and from a mammal. The hybrid promoter consists essentially of Saccharomyces cerevisiae PHO5 or GAP-DH promoter from which the upstream activation site (UAS) has been deleted and replaced by the early enhancer region derived from SV40 virus.

Cloning Site

The cloning site in the cassette in the primary vector should be designed so that any nucleotide sequence can be cloned into it.

The cloning site in the cassette preferably allows directional cloning. Hereby is ensured that transcription in a host cell is performed from the coding strand in the intended direction and that the translated peptide is identical to the peptide for which the original nucleotide sequence codes.

However according to some embodiments it may be advantageous to insert the sequence in opposite direction. According to these embodiments, so-called antisense constructs may be inserted which prevent functional expression of specific genes involved in specific pathways. Thereby it may become possible to divert metabolic intermediates from a prevalent pathway to another less dominant pathway.

The cloning site in the cassette may comprise multiple cloning sites, generally known as MCS or polylinker sites, which is a synthetic DNA sequence encoding a series of restriction endonuclease recognition sites. These sites are engineered for convenient cloning of DNA into a vector at a specific position and for directional cloning of the insert.

Cloning of cDNA does not have to involve the use of restriction enzymes. Other alternative systems include but are not limited to:

Creator™ Cre-loxP system from Clontech, which uses recombination and loxP sites use of Lambda attachment sites (att-λ), such as the Gateway™ system from Life Technologies.

Both of these systems are directional.

Terminator

The role of the terminator sequence is to limit transcription to the length of the coding sequence. An optimal terminator sequence is thus one, which is capable of performing this act in the host cell.

In prokaryotes, sequences known as transcriptional terminators signal the RNA polymerase to release the DNA template and stop transcription of the nascent RNA.

In eukaryotes, RNA molecules are transcribed well beyond the end of the mature mRNA molecule. New transcripts are enzymatically cleaved and modified by the addition of a long sequence of adenylic acid residues known as the poly-A tail. A polyadenylation consensus sequence is located about 10 to 30 bases upstream from the actual cleavage site.

Preferred examples of yeast derived terminator sequences include, but are not limited to: ADN1, CYC1, GPD, ADH1 alcohol dehydrogenase.

Intron

Optionally, the cassette in the vector comprises an intron sequence, which may be located 5' or 3' to the expressible nucleotide sequence. The design and layout of introns is well known in the art. The choice of intron design largely depends on the intended host cell, in which the expressible nucleotide sequence is eventually to be expressed. The effects of having intron sequence in the expression cassettes are those generally associated with intron sequences.

Examples of yeast introns can be found in the literature and in specific databases such as Ares Lab Yeast lntron Database (Version 2.1) as updated on 15 Apr. 2000. Earlier versions of the database as well as extracts of the database have been published in: "Genome-wide bioinformatic and molecular analysis of introns in Saccharomyces cerevisiae." by Spingola M, Grate L, Haussier D, Ares M Jr. .(RNA February 1999;5(2):221-34) and "Test of intron predictions reveals novel splice sites, alternatively spliced mRNAs and new introns in meiotically regulated genes of yeast." by Davis C A, Grate L, Spingola M, Ares M Jr, (Nucleic Acids Res Apr. 15, 2000;28(8):1700-6).

Primary Vectors (Entry Vectors)

By the term entry vector is meant a vector for storing and amplifying cDNA or other expressible nucleotide sequences using the cassettes according to the present invention. The primary vectors are preferably able to propagate in E. coli or any other suitable standard host cell. It should preferably be amplifiable and amenable to standard normalisation and enrichment procedures.

The primary vector may be of any type of DNA that has the basic requirements of a) being able to replicate itself in at least one suitable host organism and b) allows insertion of foreign DNA which is then replicated together with the vector and c) preferably allows selection of vector molecules that contain insertions of said foreign DNA. In a preferred embodiment the vector is able to replicate in standard hosts like yeasts, and bacteria and it should preferably have a high copy number per host cell. It is also preferred that the vector in addition to a host specific origin of replication, contains an origin of replication for a single stranded virus, such as e.g. the f1 origin for filamentous phages. This will allow the production of single stranded nucleic acid which may be useful for normalisation and enrichment procedures of cloned sequences. A vast number of cloning vectors have been described which are commonly used and references may be given to e.g. Sambrook, J; Fritsch, E. F; and Maniatis T. (1989) Molecular Cloning: A laboratory manual. Cold Spring Harbour Laboratory Press, USA, Netherlands Culture Collection of Bacteria (www DOT cbs DOT knaw DOT nl/NCCB/collection DOT htm) or Department of Microbial Genetics, National Institute of Genetics, Yata 1111 Mishima Shizuoka 411-8540, Japan www DOT shigen DOT nig DOT ac DOT jp/cvector/cvector DOT html). A few type-examples that are the parents of many popular derivatives are M13mp10, pUC18, Lambda gt 10, and pYAC4. Examples of primary vectors include but are not limited to M13K07, pBR322, pUC18, pUC19, pUC118, pUC119, pSP64, pSP65, pGEM-3, pGEM-3Z, pGEM-3Zf (-), pGEM-4, pGEM-4Z, nAN13, pBluescript II, CHARON 4A, λ*, CHARON 21A, CHARON 32, CHARON 33, CHARON 34, CHARON 35, CHARON 40, EMBL3A, λ2001, λDASH, λFIX, λgt10, λgt11, λgt18, λgt20, λgt22, λORF8, λZAP/R, pJB8, c2RB, and pcos1EMBL.

Methods for cloning of cDNA or genomic DNA into a vector are well known in the art. Reference may be given to J. Sambrook, E. F. Fritsch, T. Maniatis: Molecular Cloning, A Laboratory Manual ($2^{nd}$ edition, Cold Spring Harbor Laboratory Press, 1989).

Figure 3:
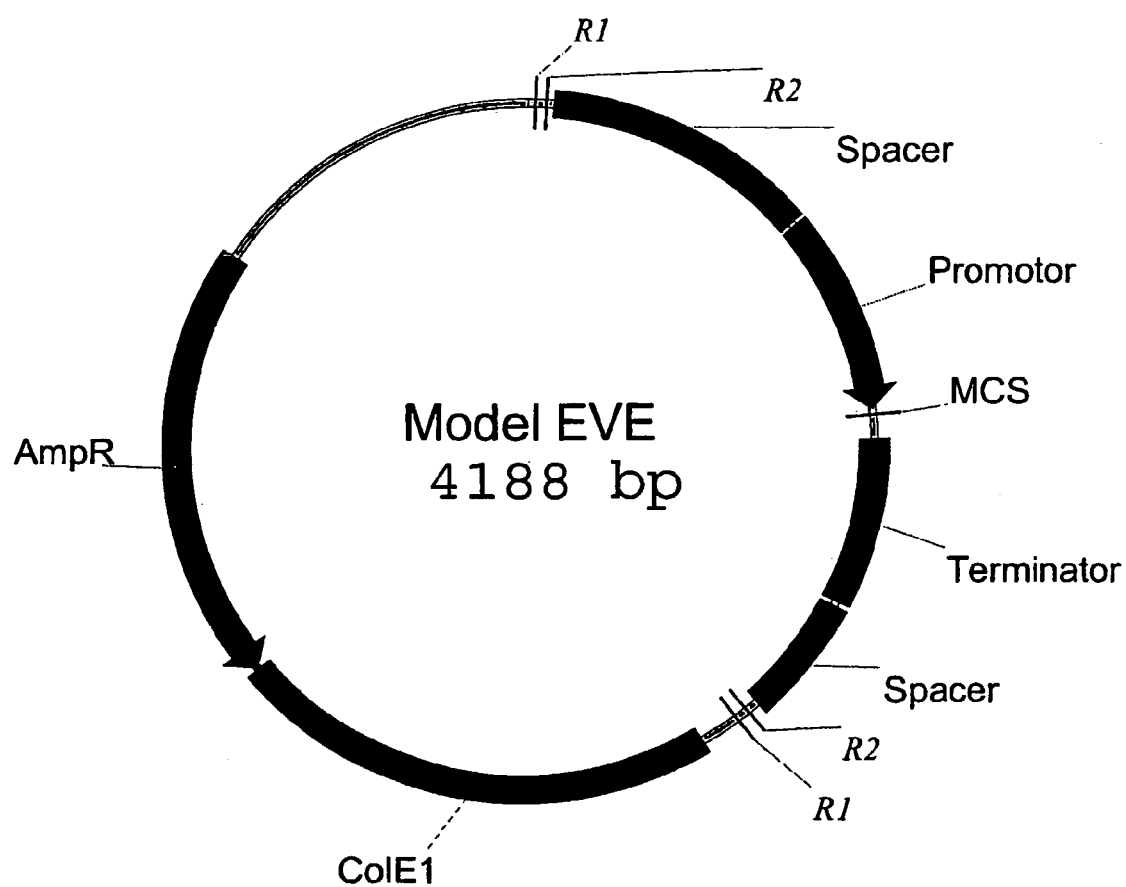
FIG. 3 shows a model entry vector. MCS is a multi cloning site for inserting expressible nucleotide sequences. Amp R is the gene for ampicillin resistance. Col E is the origin of replication in *E. coli*. R1 and R2 are restriction enzyme recognition sites.

One example of a circular model entry vector is described in FIG. 3. The vector, EVE contains the expression cassette, R1-R2-Spacer-Promoter-Multi Cloning Site-Terminator-Spacer-R2-R1. The vector furthermore contains a gene for ampicillin resistance, AmpR, and an origin of replication for *E.coli*, ColE1.

Figure 4:
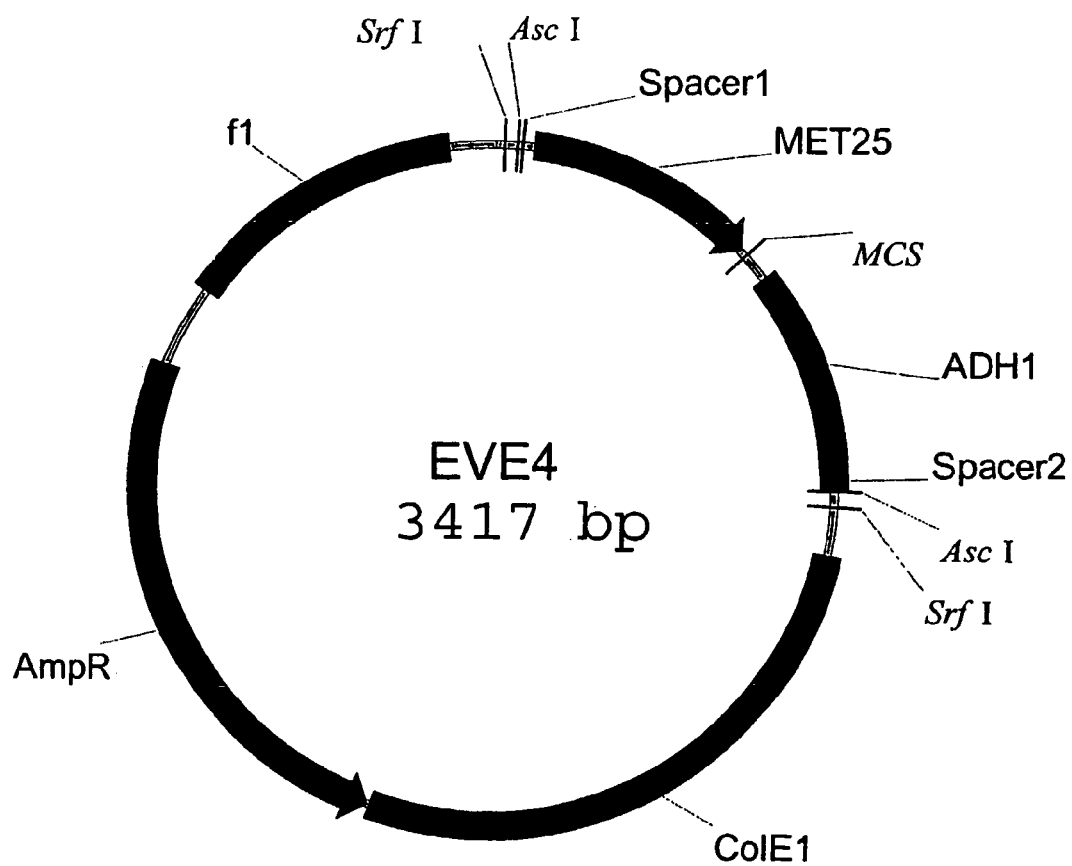
FIG. 4 shows an example of an entry vector according to the invention, EVE4. MET25 is a promoter, ADH1 is a terminator, f1 is an origin of replication for filamentous phages, e.g. M13. Spacer 1 and spacer 2 are constituted by a few nucleotides deriving from the multiple cloning site, MCS, SrfI and AscI are restriction enzyme recognition sites. Other abbreviations, see FIG. 3. The sequence of the vector is set forth in SEQ ID NO 1.
Figure 5:
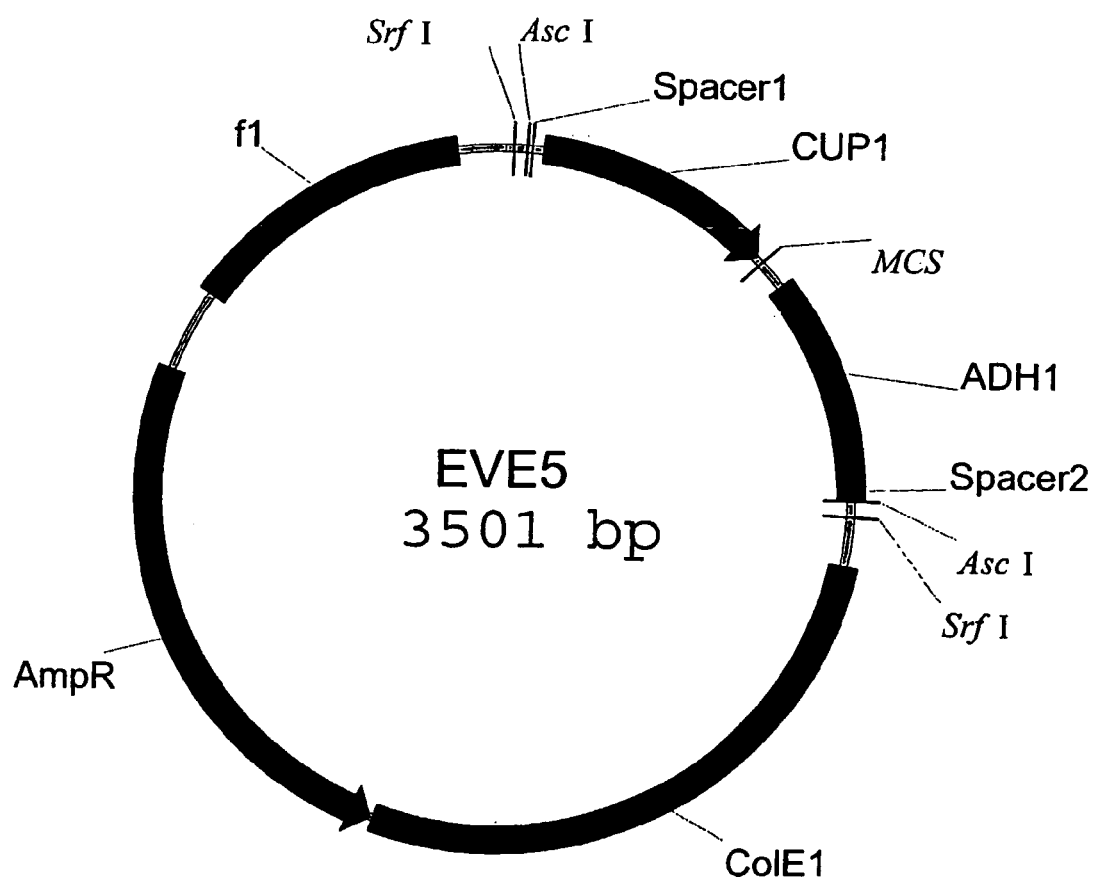
FIG. 5 shows an example of an entry vector according to the invention, EVE5. CUP1 is a promoter, ADH1 is a terminator, f1 is an origin of replication for filamentous phages, e.g. M13. Spacer 1 and spacer 2 are constituted by a few nucleotides deriving from the multiple cloning site, MCS, SrfI and AscI are restriction enzyme recognition sites. Other abbreviations, see FIG. 3. The sequence of the vector is set forth in SEQ ID NO 2.
Figure 6:
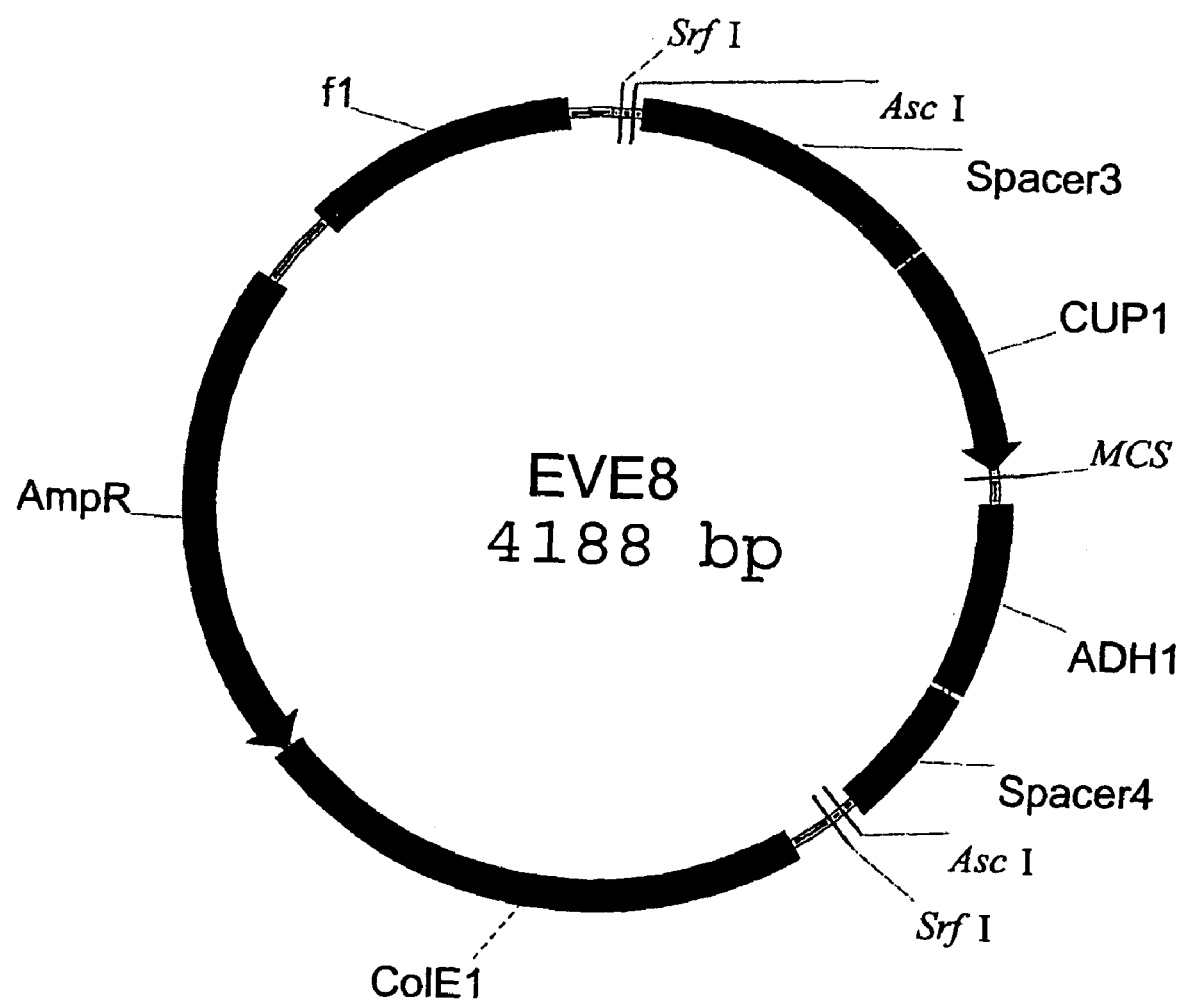
FIG. 6 shows an example of an entry vector according to the invention, EVE8. CUP1 is a promoter, ADH1 is a terminator, f1 is an origin of replication for filamentous phages, e.g. M13. Spacer3 is a 550 bp fragment of lambda phage DNA. Spacer4 is a ARS1 sequence from yeast. SrfI and AscI are restriction enzyme recognition sites. Other abbreviations, see FIG. 3. The sequence of the vector is set forth in SEQ ID NO 3.

The entry vectors EVE4, EVE5, and EVE8 shown in FIGS. 4, 5, and 6. These all contain SrfI as R1 and AscI as R2. Both of these sites are palindromic and are regarded as rare restriction sites having 8 bases in the recognition sequence. The vectors furthermore contain the AmpR ampicillin resistance gene, and the ColE1 origin or replication for *E.coli* as well as f1, which is an origin of replication for filamentous phages, such as M13. EVE4 (FIG. 4) contains the MET25 promoter and the ADH1 terminator. Spacer 1 and spacer 2 are short sequences deriving from the multiple cloning site, MCS. EVE5 (FIG. 5) contains the CUP1 promoter and the ADH1 terminator. EVE8 (FIG. 6) contains the CUP1 promoter and the ADH1 terminator. The spacers of EVE8 are a 550 bp lambda phage DNA (spacer 3) and an ARS sequence from yeast (spacer 4).

Nucleotide Library (Entry Library)

Methods as well as suitable vectors and host cells for constructing and maintaining a library of nucleotide sequences in a cell are well known in the art. The primary requirement for the library is that is should be possible to store and amplify in it a number of primary vectors (constructs) according to this invention, the vectors (constructs) comprising expressible nucleotide sequences from at least one expression state and wherein at least two vectors (constructs) are different.

One specific example of such a library is the well known and widely employed cDNA libraries. The advantage of the cDNA library is mainly that it contains only DNA sequences corresponding to transcribed messenger RNA in a cell. Suitable methods are also present to purify the isolated mRNA or the synthesised cDNA so that only substantially full-length cDNA is cloned into the library.

Methods for optimisation of the process to yield substantially full length cDNA may comprise size selection, e.g. electrophoresis, chromatography, precipitation or may comprise ways of increasing the likelihood of getting full length cDNAs, e.g. the SMART™ method (Clonetech) or the Cap-Trap™ method (Stratagene).

Preferably the method for making the nucleotide library comprises obtaining a substantially full length cDNA population comprising a normalised representation of cDNA species. More preferably a substantially full length cDNA population comprises a normalised representation of cDNA species characteristic of a given expression state.

Normalisation reduces the redundancy of clones representing abundant mRNA species and increases the relative representation of clones from rare mRNA species.

Methods for normalisation of cDNA libraries are well known in the art. Reference may be given to suitable protocols for normalisation such as those described in U.S. Pat. No. 5,763,239 (DIVERSA) and WO 95/08647 and WO 95/11986. and Bonaldo, Lennon, Soares, Genome Research 1996, 6:791-806; Ali, Holloway, Taylor, Plant Mol Biol Reporter, 2000,18:123-132.

Enrichment methods are used to isolate clones representing mRNA which are characteristic of a particular expression state. A number of variations of the method broadly termed as subtractive hybrisation are known in the art. Reference may be given to Sive, John, Nucleic Acid Res, 1988, 16:10937; Diatchenko, Lau, Campbell et al, PNAS, 1996, 93:6025-6030; Caminci, Shibata, Hayatsu, Genome Res, 2000, 10:1617-30, Bonaldo, Lennon, Soares, Genome Research 1996, 6:791-806; Ali, Holloway, Taylor, Plant Mol Biol Reporter, 2000, 18:123-132. For example, enrichment may be achieved by doing additional rounds of hybridization similar to normalization procedures, using e.g. cDNA from a library of abundant clones or simply a library representing the uninduced state as a driver against a tester library from the induced state. Alternatively mRNA or PCR amplified cDNA derived from the expression state of choice can be used to subtract common sequences from a tester library. The choice of driver and tester population will depend on the nature of target expressible nucleotide sequences in each particular experiment.

In the library an expressible nucleotide sequence coding for one peptide is preferably found in different but similar vectors under the control of different promoters. Preferably the library comprises at least three primary vectors with an expressible nucleotide sequence coding for the same peptide under the control of three different promoters. More preferably the library comprises at least four primary vectors with an expressible nucleotide sequence coding for the same peptide under the control of four different promoters. More preferably the library comprises at least five primary vectors with an expressible nucleotide sequence coding for the same peptide under the control of five different promoters, such as comprises at lest six primary vectors with an expressible nucleotide sequence coding for the same peptide under the control of six different promoters, for example comprises at least seven primary vectors with an expressible nucleotide sequence coding for the same peptide under the control of seven different promoters, for example comprises at least eight primary vectors with an expressible nucleotide sequence coding for the same peptide under the control of eight different promoters, such as comprises at least nine primary vectors with an expressible nucleotide sequence coding for the same peptide under the control of nine different promoters, for example comprises at least ten primary vectors with an expressible nucleotide sequence coding for the same peptide under the control of ten different promoters.

The expressible nucleotide sequence coding for the same peptide preferably comprises essentially the same nucleotide sequence, more preferably the same nucleotide sequence.

By having a library with what may be termed one gene under the control of a number of different promoters in different vectors, it is possible to construct from the nucleotide library an array of combinations of genes and promoters. Preferably, one library comprises a complete or substantially complete combination such as a two dimensional array of genes and promoters, wherein substantially all genes are found under the control of substantially all of a selected number of promoters.

According to another embodiment of the invention the nucleotide library comprises combinations of expressible nucleotide sequences combined in different vectors with different spacer sequences and/or different intron sequences. Thus any one expressible nucleotide sequence may be combined in a two, three, four or five dimensional array with different promoters and/or different spacers and/or different introns and/or different terminators. The two, three, four or five dimensional array may be complete or incomplete, since not all combinations will have to be present.

The library may suitably be maintained in a host cell comprising prokaryotic cells or eukaryotic cells. Preferred prokaryotic host organisms may include but are not limited to *Escherichia coli, Bacillus subtilis, Streptomyces lividans, Streptomyces coelicolor Pseudomonas aeruginosa, Myxococcus xanthus.*

Yeast species such as *Saccharomyces cerevisiae* (budding yeast), *Schizosaccharomyces pombe* (fission yeast), *Pichia pastoris*, and *Hansenula polymorpha* (methylotropic yeasts) may also be used. *Filamentous ascomycetes*, such as *Neurospora crassa* and *Aspergillus nidulans* may also be used. Plant cells such as those derived from *Nicotiana* and *Arabidopsis* are preferred. Preferred mammalian host cells include but are not limited to those derived from humans, monkeys and rodents, such as chinese hamster ovary (CHO) cells, NIH/3T3, COS, 293, VERO, HeLa etc (see Kriegler M. in "Gene Transfer and Expression: A Laboratory Manual", New York, Freeman & Co. 1990).

Concatemers

A concatemer is a series of linked units. In the present context a concatemer is used to denote a number of serially linked nucleotide cassettes, wherein at least two of the serially linked nucleotide units comprises a cassette having the basic structure

[rs$_2$SP-PR-X-TR-SP-rs$_1$]

wherein
rs$_1$ and rs$_2$ together denote a restriction site,
SP individually denotes a spacer of at least two nucleotide bases,
PR denotes a promoter, capable of functioning in a cell,
X denotes an expressible nucleotide sequence,
TR denotes a terminator, and
SP individually denotes a spacer of at least two nucleotide bases.

Optionally the cassettes comprise an intron sequence between the promoter and the expressible nucleotide sequence and/or between the terminator and the expressible sequence.

The expressible nucleotide sequence in the cassettes of the concatemer may comprise a DNA sequence selected from the group comprising cDNA and genomic DNA.

According to one aspect of the invention, a concatemer comprises cassettes with expressible nucleotide from different expression states, so that non-naturally occurring combinations or non-native combinations of expressible nucleotide sequences are obtained. These different expression states may represent at least two different tissues, such as at least two organs, such as at least two species, such as at least two genera. The different species may be from at least two different phylae, such as from at least two different classes, such as from at least two different divisions, more preferably from at least two different sub-kingdoms, such as from at least two different kingdoms.

For example, the expressible nucleotide sequences may originate from eukaryots such as mammals such as humans, mice or whale, from reptiles such as snakes crocodiles or turtles, from tunicates such as sea squirts, from lepidoptera such as butterflies and moths, from coelenterates such as jellyfish, anenomes, or corals, from fish such as bony and cartilaginous fish, from plants such as dicots, e.g. coffee, oak or monocots such as grasses, lilies, and orchids; from lower plants such as algae and gingko, from higher fungi such as terrestrial fruiting fungi, from marine actinomyceites. The expressible nucleotide sequences may also originate from protozoans such as malaria or trypanosomes, or from prokaryotes such as *E. coli* or archaebacteria. Furthermore, the expressible nucleotide sequences may originate from one or more preferably from more expression states from the species and genera listed in the table below.

| | |
|---|---|
| Bacteria | *Streptomyces, Micromonospora, Norcadia, Actinomadura, Actinoplanes, Streptosporangium, Microbispora, Kitasatosporiam, Azobacterium, Rhizobium, Achromobacterium, Enterobacterium, Brucella, Micrococcus, Lactobacillus, Bacillus* (B.t. toxins), *Clostridium* (toxins), *Brevibacterium, Pseudomonas, Aerobacter, Vibrio, Halobacterium, Mycoplasma, Cytophaga, Myxococcus* |
| Fungi | *Amanita muscaria* (fly agaric, ibotenic acid, muscimol), *Psilocybe* (psilocybin) *Physarium, Fuligo, Mucor, Phytophtora, Rhizopus, Aspergillus, Penicillium* (penicillin), *Coprinus, Phanerochaete, Acremonium* (Cephalosporin), *Trochoderma, Helminthosporium, Fusarium, Alternaria, Myrothecium, Saccharomyces* |
| Algae | Digenea simplex (kainic acid, antihelminthic), *Laminaria anqustata* (laminine, hypotensive) |
| Lichens | *Usnea fasciata* (vulpinicacid, antimicrobial; usnic acid, antitumor) |
| Higher Plants | *Artemisia* (artemisinin), *Coleus* (forskolin), *Desmodium* (K channel agonist), *Catharanthus* (Vinca alkaloids), *Digitalis* (cardiac glycosides), *Podophyllum* (podophyllotoxin), *Taxus* (taxol), *Cephalotaxus* (homoharringtonine), *Camptotheca* (Camptothecin), *Camellia sinensis* (Tea), *Cannabis indica, Cannabis sativa* (Hemp), *Erythroxylum coca* (Coca), *Lophophora williamsii* (Peyote*Myristica fragrans* (Nutmeg), *Nicotiana, Papaver somniferum* (Opium Poppy), *Phalaris arundinacea* (Reed canary grass) |
| Protozoa | *Ptychodiscus brevis*; Dinoflagellates (brevitoxin, cardiovascular) |
| Sponges | *Microciona prolifera* (ectyonin, antimicrobial) *Cryptotethya cryta* (D-arabino furanosides) |
| Coelenterata | Portuguese Man o War & other jellyfish and medusoid toxins. |
| Corals | *Pseudoterogonia* species (Pseudoteracins, anti-inflammatory), Erythropodium (erythrolides, anti-inflammatory) |

-continued

| | |
|---|---|
| Aschelminths | Nematode secretory compounds |
| Molluscs | Conus toxins, sea slug toxins, cephalapod neurotransmitters, squid inks |
| Annelida | *Lumbriconereis heteropa* (nereistoxin, insecticidal) |
| Arachnids | *Dolomedes* ("fishing spider" venoms) |
| Crustacea | *Xenobalanus* (skin adhesives) |
| Insects | *Epilachna* (mexican bean beetle alkaloids) |
| Spinunculida | *Bonellia viridis* (bonellin, neuroactive) |
| Bryozoans | *Bugula neritina* (bryostatins, anti cancer) |
| Echinoderms | Crinoid chemistry |
| Tunicates | *Trididemnum solidum* (didemnin, anti-tumor and anti-viral; *Ecteinascidia turbinata* ecteinascidins, anti-tumor) |
| Vertebrates | *Eptatretus stoutii* (eptatretin, cardioactive), *Trachinus draco* (proteinaceous toxins, reduce blood pressure, respiration and reduce heart rate). Dendrobatid frogs (batrachotoxins, pumiliotoxins, histrionicotoxins, and other polyamines); Snake venom toxins; *Orinthorhynohus anatinus* (duck-billed platypus venom), modified carotenoids, retinoids and steroids; Avians: histrionicotoxins, modified carotenoids, retinoids and steroids |

According to a preferred embodiment of the invention the concatemer comprises at least a first cassette and a second cassette; said first-cassette being different from said second cassette. More preferably, the concatemer comprises cassettes, wherein substantially all cassettes are different. The difference between the cassettes may arise from differences between promoters, and/or expressible nucleotide sequences, and/or spacers, and/or terminators, and/or introns.

The number of cassettes in a single concatemer is largely determined by the host species into which the concatemer is eventually to be inserted and the vector through which the insertion is carried out. The concatemer thus may comprise at least 10 cassettes, such as at least 15, for example at least 20, such as at least 25, for example at least 30, such as from 30 to 60 or more than 60, such as at least 75, for example at least 100, such as at least 200, for example at least 500, such as at least 750, for example at least 1000, such as at least 1500, for example at least 2000 cassettes.

Each of the cassettes may be laid out as described above.

Once the concatemer has been assembled or concatenated it may be ligated into a suitable vector. Such a vector may advantageously comprise an artificial chromosome. The basic requirements for a functional artificial chromosome have been described in U.S. Pat. No. 4,464,472, the contents of which is hereby incorporated by reference. An artificial chromosome or a functional minichromosome, as it may also be termed must comprise a DNA sequence capable of replication and stable mitotic maintenance in a host cell comprising a DNA segment coding for centromere-like activity during mitosis of said host and a DNA sequence coding for a replication site recognized by said host.

Suitable artificial chromosomes include a Yeast Artificial Chromosome (YAC) (see e.g. Murray et al, Nature 305:189-193; or U.S. Pat. No. 4,464,472), a mega Yeast Artificial Chromosome (mega YAC), a Bacterial Artificial Chromosome (BAC), a mouse artificial chromosome, a Mammalian Artificial Chromosome (MAC) (see e.g. U.S. Pat. Nos. 6,133,503 or 6,077,697), an Insect Artificial Chromosome (BUGAC), an Avian Artificial Chromosome (AVAC), a Bacteriophage Artificial Chromosome, a Baculovirus Artificial Chromosome, a plant artificial chromosome (U.S. Pat. No. 5,270,201), a BIBAC vector (U.S. Pat. No. 5,977,439) or a Human Artificial Chromosome (HAC).

The artificial chromosome is preferably so large that the host cell perceives it as a "real" chromosome and maintains it and transmits it as a chromosome. For yeast and other suitable host species, this will often correspond approximately to the size of the smallest native chromosome in the species. For *Saccharomyces*, the smallest chromosome has a size of 225 Kb.

MACs may be used to construct artificial chromosomes from other species, such as insect and fish species. The artificial chromosomes preferably are fully functional stable chromosomes. Two types of artificial chromosomes may be used. One type, referred to as SATACs [satellite artificial chromosomes] are stable heterochromatic chromosomes, and the other type are minichromosomes based on amplification of euchromatin.

Mammalian artificial chromosomes provide extra-genomic specific integration sites for introduction of genes encoding proteins of interest and permit megabase size DNA integration, such as integration of concatemers according to the invention.

According to another embodiment of the invention, the concatemer may be integrated into the host chromosomes or cloned into other types of vectors, such as a plasmid vector, a phage vector, a viral vector or a cosmid vector.

A preferable artificial chromosome vector is one that is capable of being conditionally amplified in the host cell, e.g. in yeast. The amplification preferably is at least a 10 fold amplification. Furthermore, it is advantageous that the cloning site of the artificial chromosome vector can be modified to comprise the same restriction site as the one bordering the cassettes described above, i.e. RS2 and/or RS2'.

Concatenation

Cassettes to be concatenated are normally excised from a vector either by digestion with restriction enzymes or by PCR. After excision the cassettes may be separated from the vector through size fractionation such as gel filtration or through tagging of known sequences in the cassettes. The isolated cassettes may then be joined together either through interaction between sticky ends or through ligation of blunt ends.

Single-stranded compatible ends may be created by digestion with restriction enzymes. For concatenation a preferred enzyme for excising the cassettes would be a rare cutter, i.e. an enzyme that recognises a sequence of 7 or more nucleotides. Examples of enzymes that cut very rarely are the meganucleases, many of which are intron encoded, like e.g. I-Ceu I, I-Sce I, I-Ppo I, and PI-Psp I (see eample 6d for more). Other preferred enzymes recognize a sequence of 8 nucleotides like e.g. Asc I, AsiS I, CciN I, CspB I, Fse I, MchA I, Not I, Pac I, Sbf I, Sda I, Sgf I, SgrA I, Sse232 I, and Sse8387 I, all of which create single stranded, palindromic compatible ends.

Other preferred rare cutters, which may also be used to control orientation of individual cassettes in the concatemer are enzymes that recognize non-palindromic sequences like e.g. Aar I, Sap I, Sfi I, Sdi I, and Vpa (see example 6c for more).

Alternatively, cassettes can be prepared by the addition of restriction sites to the ends, e.g. by PCR or ligation to linkers (short synthetic dsDNA molecules). Restriction enzymes are continuously being isolated and characterised and it is anticipated that many of such novel enzymes can be used to generate single-stranded compatible ends according to the present invention.

It is conceivable that single stranded compatible ends can be made by cleaving the vector with synthetic cutters. Thus, a reactive chemical group that will normally be able to cleave DNA unspecifically can cut at specific positions when coupled to another molecule that recognises and binds to specific sequences. Examples of molecules that recognise specific dsDNA sequences are DNA, PNA, LNA, phosphothioates, peptides, and amides. See e.g. Armitage, B.(1998) Chem. Rev. 98: 1171-1200, who describes photocleavage using e.g. anthraquinone and UV light; Dervan P. B. & Burli R. W. (1999) Curr. Opin. Chem. Biol. 3: 688-93 describes the specific binding of polyamides to DNA; Nielsen, P. E. (2001) Curr. Opin. Biotechnol. 12: 16-20 describes the specific binding of PNA to DNA, and Chemical Reviews special thematic issue: RNA/DNA Cleavage (1998) vol. 98 (3) Bashkin J. K. (ed.) ACS publications, describes several examples of chemical DNA cleavers.

Single-stranded compatible ends may also be created by using e.g. PCR primers including dUTP and then treating the PCR product with Uracil-DNA glycosylase (Ref: U.S. Pat. No. 5,035,996) to degrade part of the primer. Alternatively, compatible ends can be created by tailing both the vector and insert with complimentary nucleotides using Terminal Transferase (Chang, LMS, Bollum TJ (1971) J Biol Chem 246: 909).

It is also conceivable that recombination can be used to generate concatemers, e.g. through the modification of techniques like the Creator™ system (Clontech) which uses the Cre-loxP mechanism (Sauer B 1993 Methods Enzymol 225: 890-900) to directionally join DNA molecules by recombination or like the Gateway™ system (Life Technologies, U.S. Pat. No. 5,888,732) using lambda aft attachment sites for directional recombination (Landy A 1989, Ann Rev Biochem 58:913). It is envisaged that also lambda cos site dependent systems can be developed to allow concatenation.

More preferably the cassettes may be concatenated without an intervening purification step through excision from a vector with two restriction enzymes, one leaving sticky ends on the cassettes and the other one leaving blunt ends in the vectors. This is the preferred method for concatenation of cassettes from vectors having the basic structure of [RS1-RS2-SP-PR-X-TR-SP-RS2'-RS1'].

An alternative way of producing concatemers free of vector sequences would be to PCR amplify the cassettes from a single stranded primary vector. The PCR product must include the restriction sites RS2 and RS2' which are subsequently cleaved by its cognate enzyme(s). Concatenation can then be performed using the digested PCR product, essentially without interference from the single stranded primary vector template or the small double stranded fragments, which have been cut from the ends.

Figure 1:
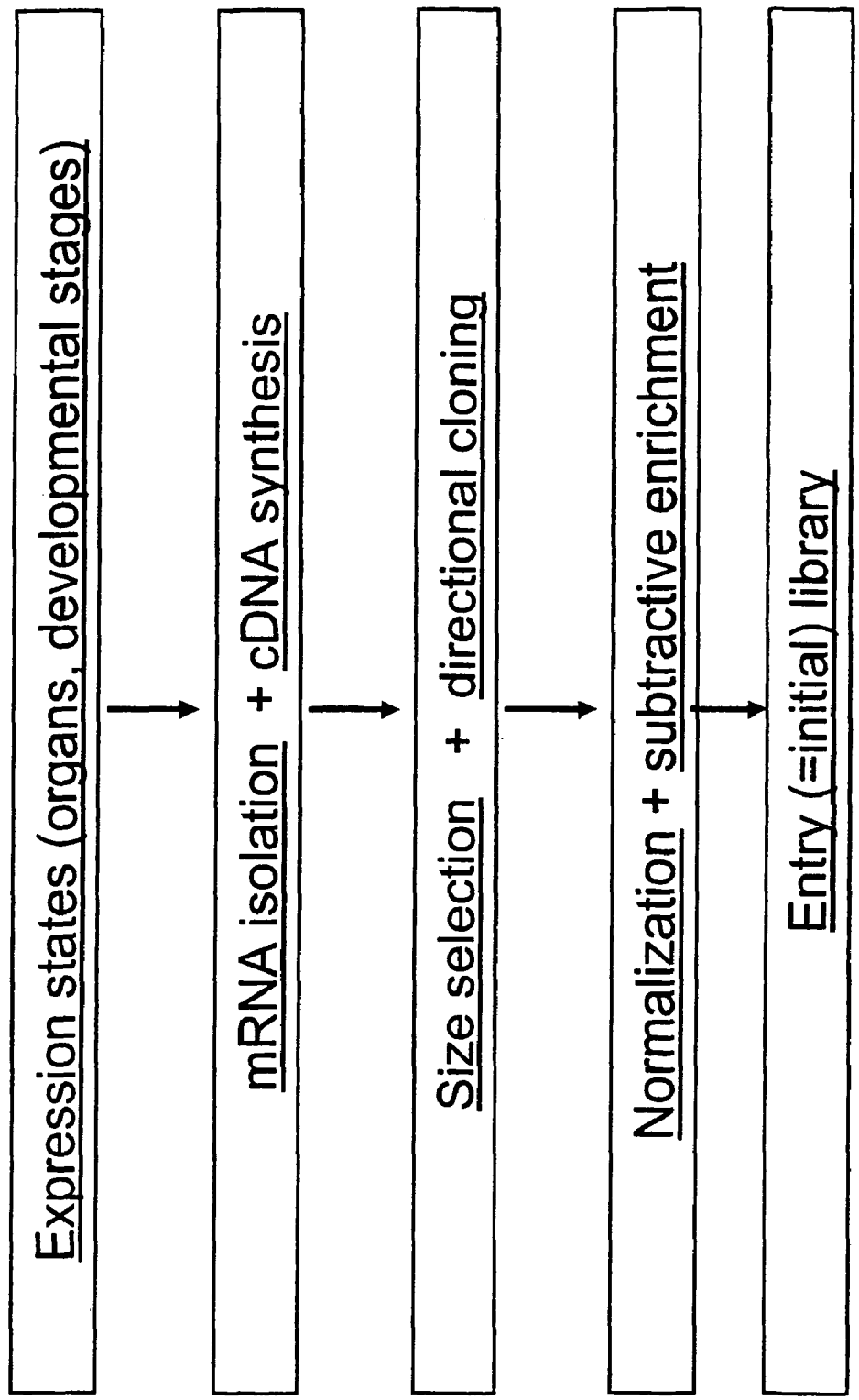
FIG. 1 shows a flow chart of the steps leading from an expression state to incorporation of the expressible nucleotide sequences in an entry library (a nucleotide library according to the invention).
Figure 2A:
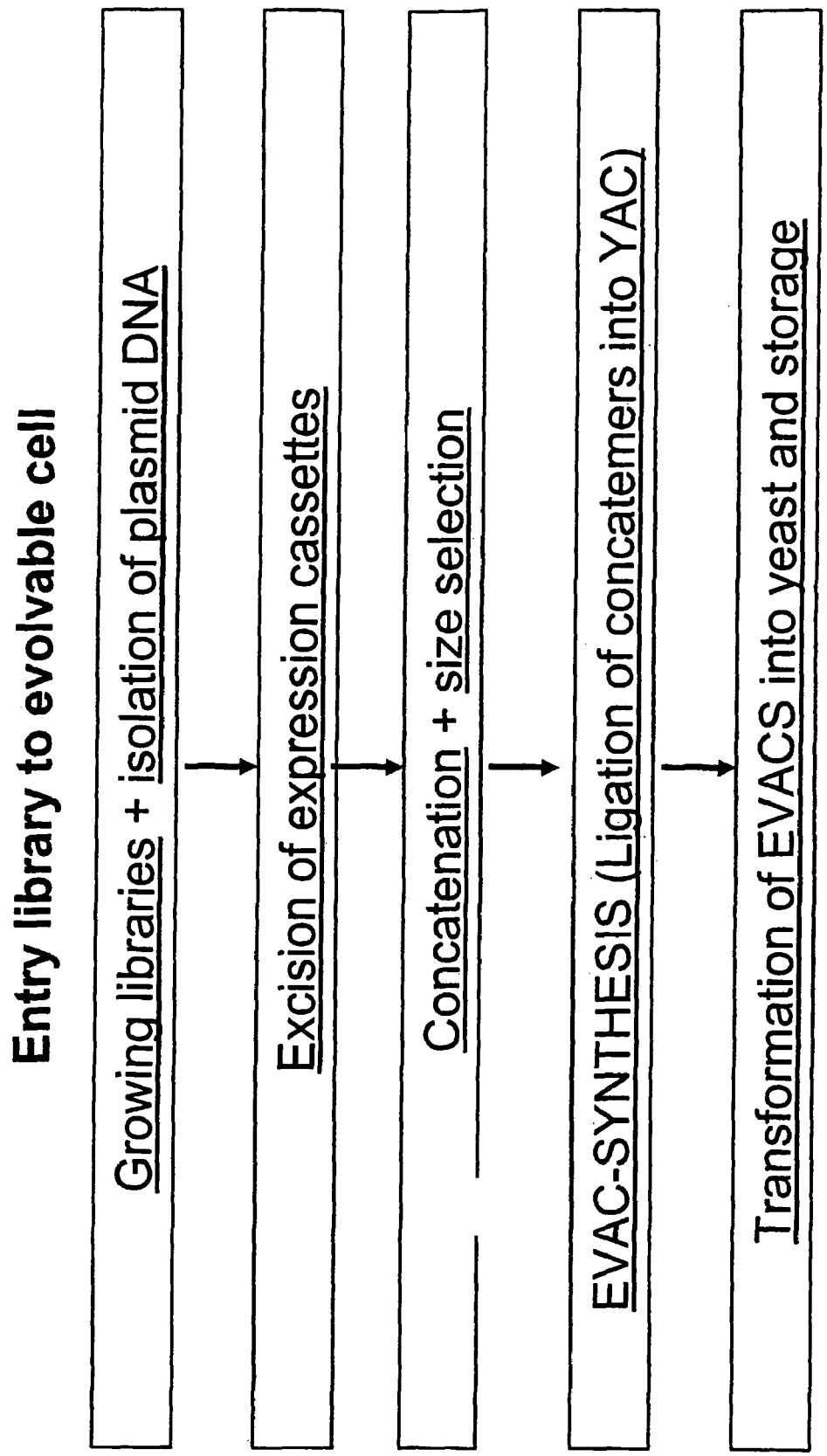
FIG. 2*a* shows one way of producing the EVACs which includes concatenation, size selection and insertion into an artificial chromosome vector.

The concatemer may be assembled or concatenated by concatenation of at least two cassettes of nucleotide sequences each cassette comprising a first sticky end, a spacer sequence, a promoter, an expressible nucleotide sequence, a terminator, a spacer sequence, and a second sticky end. A flow chart of the procedure is shown in FIG. 2a.

Preferably concatenation further comprises
starting from a primary vector [RS1-RS2-SP-PR-X-TR-SP-RS2'-RS1'],
wherein X denotes an expressible nucleotide sequence,
RS1 and RS1' denote restriction sites,
RS2 and RS2' denote restriction sites different from RS1 and RS1',
SP individually denotes a spacer sequence of at least two nucleotides,
PR denotes a promoter,
TR denotes a terminator,
i) cutting the primary vector with the aid of at least one restriction enzyme specific for RS2 and RS2' obtaining cassettes having the general formula [$rs_2$-SP-PR-X-TR-SP-$rs_1$] wherein $rs_1$ and $rs_2$ together denote a functional restriction site RS2 or RS2',
ii) assembling the cut out cassettes through interaction between $rs_1$ and $rs_2$.

In this way at least 10 cassettes can be concatenated, such as at least 15, for example at least 20, such as at least 25, for example at least 30, such as from 30 to 60 or more than 60, such as at least 75, for example at least 100, such as at least 200, for example at least 500, such as at least 750, for example at least 1000, such as at least 1500, for example at least 2000.

Figure 2B:
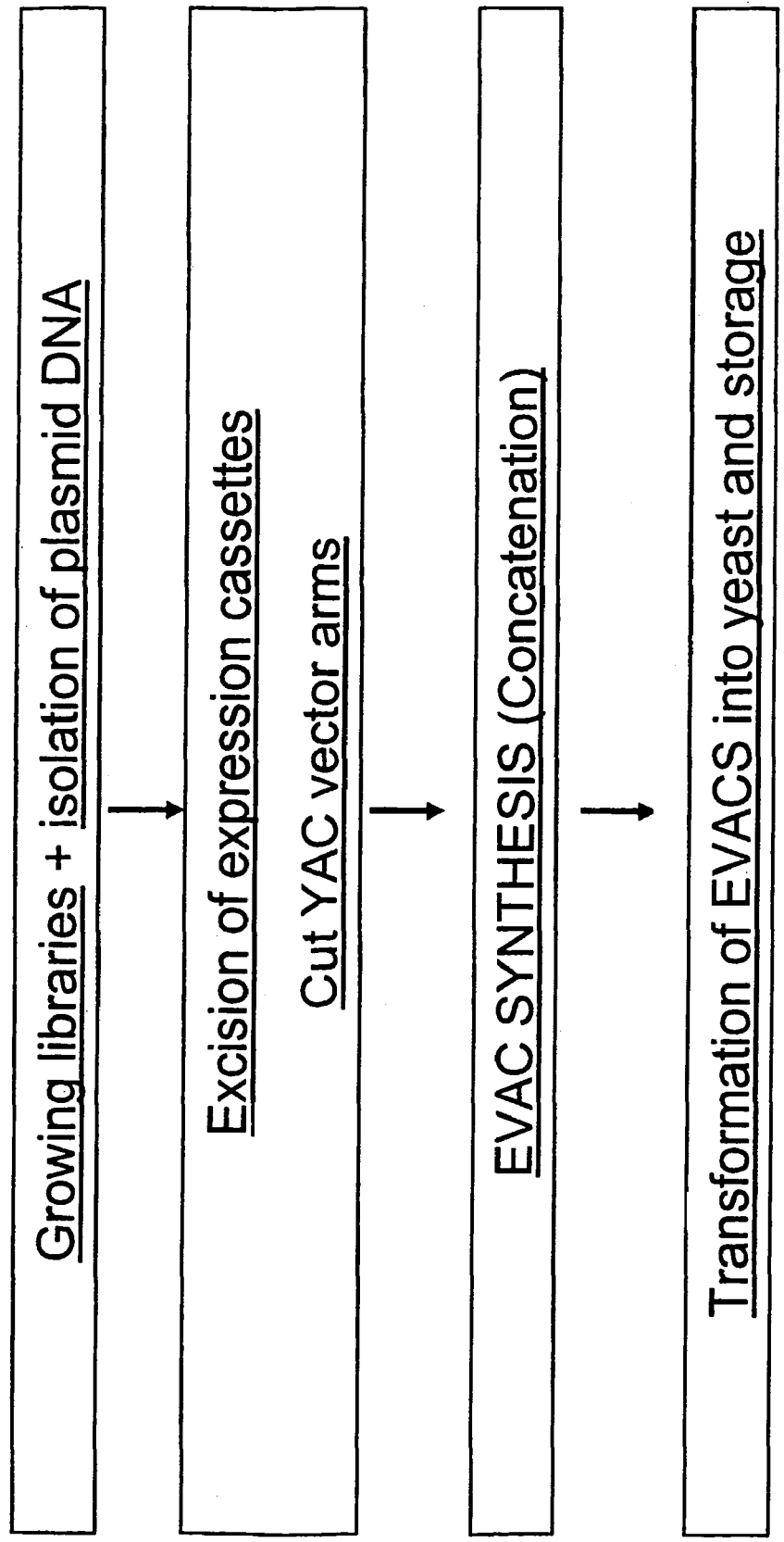
FIG. 2*b* shows a one step procedure for concatenation and ligation of vector arms to obtain EVACs.
Figure 7:
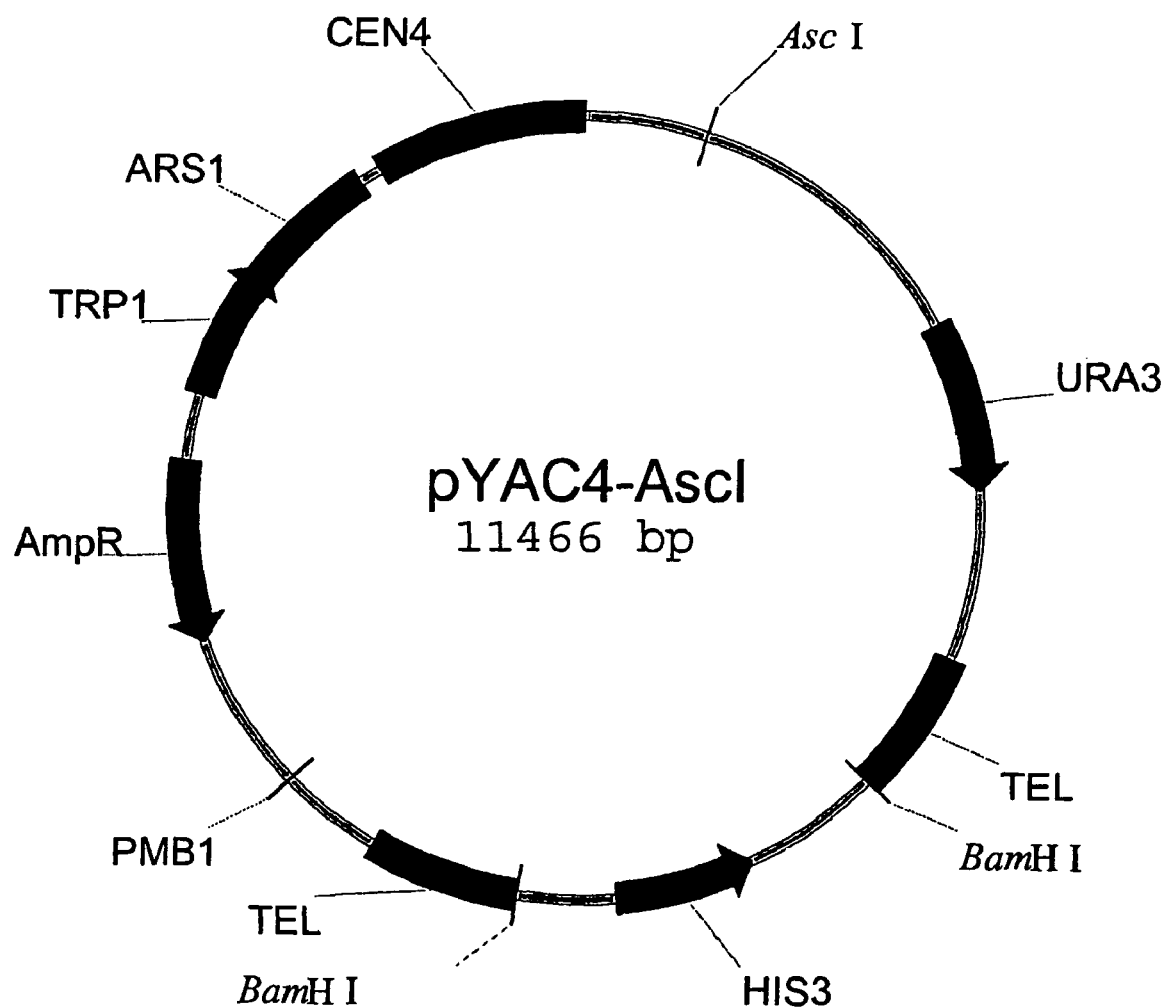
FIG. 7 shows a vector (pYAC4-AscI) for providing arms for an evolvable artificial chromosome (EVAC) into which a concatemer according to the invention can be cloned. TRP1, URA3, and HIS3 are yeast auxotrophic marker genes, and AmpR is an *E. coli* antibiotic marker gene. CEN4 is a centromere and TEL are telomeres. ARS1 and PMB1 allow replication in yeast and *E. coli* respectively. BamHI and Asc I are restriction enzyme recognition sites. The nucleotide sequence of the vector is set forth in SEQ ID NO 4.

According to an especially preferred embodiment, vector arms each having a RS2 or RS2' in one end and a non-complementary overhang or a blunt end in the other end are added to the concatenation mixture together with the cassettes described above to further simplify the procedure (see FIG. 2b). One example of a suitable vector for providing vector arms is disclosed in FIG. 7 TRP1, URA3, and HIS3 are auxotrophic marker genes, and AmpR is an E. coli antibiotic marker gene. CEN4 is a centromer and TEL are telomeres. ARS1 and PMB1 allow replication in yeast and E. coli respectively. BamHI and AscI are restriction enzyme recognition sites. The nucleotide sequence of the vector is set forth in SEQ ID NO 4. The vector is digested with BamHI and AscI to liberate the vector arms, which are used for ligation to the concatemer.

Figure 8:
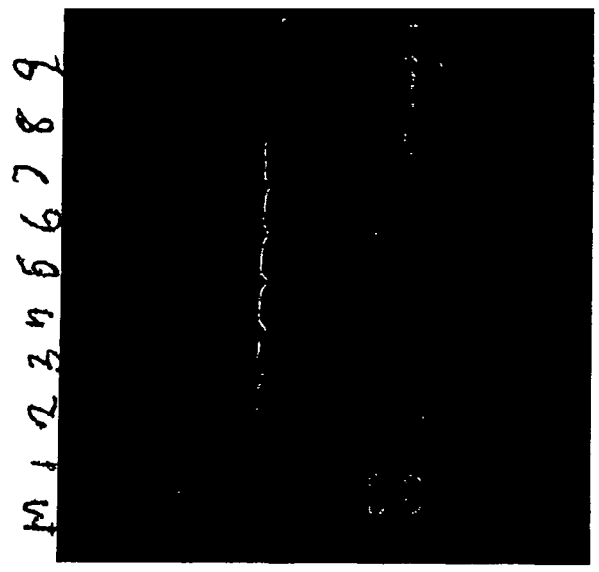
FIG. 8 shows the general concatenation strategy. On the left is shown a circular entry vector with restriction sites, spacers, promoter, expressible nucleotide sequence and terminator. These are excised and ligated randomly.
Figure 8:
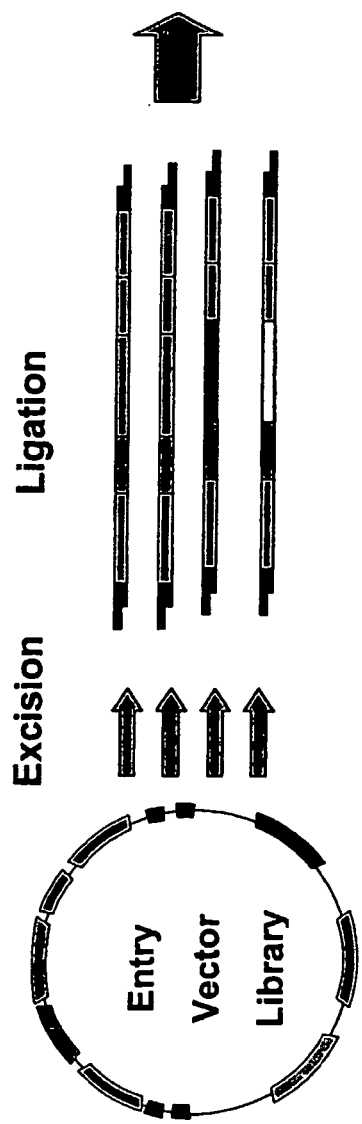

The ratio of vector arms to cassettes determines the maximum number of cassettes in the concatemer as illustrated in FIG. 8. The vector arms preferably are artificial chromosome vector arms such as those described in FIG. 7.

It is of course also possible to add stopper fragments to the concatenation solution, the stopper fragments each having a RS2 or RS2' in one end and a non-complementary overhang or a blunt end in the other end. The ratio of stopper fragments to cassettes can likewise control the maximum size of the concatemer.

The complete sequence of steps to be taken when starting with the isolation of mRNA until inserting into an entry vector may include the following steps
i) isolating mRNA from an expression state,
ii) obtaining substantially full length cDNA corresponding to the mRNA sequences,
iii) inserting the substantially full length cDNA into a cloning site in a cassette in a primary vector, said cassette being of the general formula in 5'→3' direction:

[RS1-RS2-SP-PR-CS-TR-SP-RS2'-RS1]

wherein CS denotes a cloning site.

In preparation of the concatemer, genes may be isolated from different entry libraries to provide the desired selection of genes. Accordingly, concatenation may further comprise selection of vectors having expressible nucleotide sequences from at least two different expression states, such as from two different species. The two different species may be from two different classes, such as from two different divisions, more preferably from two different sub-kingdoms, such as from two different kingdoms.

As an alternative to including vector arms in the concatenation reaction it is possible to ligate the concatemer into an artificial chromosome selected from the group comprising yeast artificial chromosome, mega yeast artificial chromosome, bacterial artificial chromosome, mouse artificial chromosome, human artificial chromosome.

Preferably at least one inserted concatemer further comprises a selectable marker. The marker(s) are conveniently not included in the concatemer as such but rather in an artificial chromosome vector, into which the concatemer is inserted. Selectable markers generally provide a means to select, for growth, only those cells which contain a vector. Such markers are of two types: drug resistance and auxotrophy. A drug resistance marker enables cells to grow in the presence of an otherwise toxic compound. Auxotrophic markers allow cells to grow in media lacking an essential component by enabling cells to synthesise the essential component (usually an amino acid).

Illustrative and non-limiting examples of common compounds for which selectable markers are available with a brief description of their mode of action follow:

Prokaryotic
  Ampicillin: interferes with a terminal reaction in bacterial cell wall synthesis. The resistance gene (bla) encodes beta-lactamase which cleaves the beta-lactam ring of the antibiotic thus detoxifying it.
  Tetracycline: prevents bacterial protein synthesis by binding to the 30S ribosomal subunit. The resistance gene (tet) specifies a protein that modifies the bacterial membrane and prevents accumulation of the antibiotic in the cell.
  Kanamycin: binds to the 70S ribosomes and causes misreading of messenger RNA. The resistant gene (nptH) modifies the antibiotic and prevents interaction with the ribosome.
  Streptomycin: binds to the 30S ribosomal subunit, causing misreading of messenger RNA. The resistance gene (Sm) modifies the antibiotic and prevents interaction with the ribosome.
  Zeocin: this new bleomycin-family antibiotic intercalates into the DNA and cleaves it. The Zeocin resistance gene encodes a 13,665 dalton protein. This protein confers resistance to Zeocin by binding to the antibiotic and preventing it from binding DNA. Zeocin is effective on most aerobic cells and can be used for selection in mammalian cell lines, yeast, and bacteria.

Eukaryotic
  Hygromycin: a aminocyclitol that inhibits protein synthesis by disrupting ribosome translocation and promoting mistranslation. The resistance gene (hph) detoxifies hygromycin —B— phosphorylation.
  Histidinol: cytotoxic to mammalian cells by inhibiting histidyl-tRNA synthesis in histidine free media. The resistance gene (hisD) product inactivates histidinol toxicity by converting it to the essential amino acid, histidine.
  Neomycin (G418): blocks protein synthesis by interfering with ribosomal functions. The resistance gene ADH encodes amino glycoside phosphotransferase which detoxifies G418.
  Uracil: Laboratory yeast strains carrying a mutated gene which encodes orotidine-5'-phosphate decarboxylase, an enzyme essential for uracil biosynthesis, are unable to grow in the absence of exogenous uracil. A copy of the wild-type gene (ura4+, S. pombe or URA3 S. cerevisiae) carried on the vector will complement this defect in transformed cells.
  Adenosine: Laboratory strains carrying a deficiency in adenosine synthesis may be complemented by a vector carrying the wild type gene, ADE 2.
  Amino acids: Vectors carrying the wild-type genes for LEU2, TRP 1, HIS 3 or LYS 2 may be used to complement strains of yeast deficient in these genes.
  Zeocin: this new bleomycin-family antibiotic intercalates into the DNA and cleaves it. The Zeocin resistance gene encodes a 13,665 dalton protein. This protein confers resistance to Zeocin by binding to the antibiotic and preventing it from binding DNA. Zeocin is effective on most aerobic cells and can be used for selection in mammalian cell lines, yeast, and bacteria.

Transgenic Cells

In one aspect of the invention, the concatemers comprising the multitude of cassettes are introduced into a host cell, in which the concatemers can be maintained and the expressible nucleotide sequences can be expressed in a coordinated way. The cassettes comprised in the concatemers may be isolated from the host cell and re-assembled due to their uniform structure with—preferably—concatemer restriction sites between the cassettes.

The host cells selected for this purpose are preferably cultivable under standard laboratory conditions using standard culture conditions, such as standard media and protocols. Preferably the host cells comprise a substantially stable cell line, in which the concatemers can be maintained for generations of cell division. Standard techniques for transformation of the host cells and in particular methods for insertion of artificial chromosomes into the host cells are known.

It is also of advantage if the host cells are capable of undergoing meiosis to perform sexual recombination. It is also advantageous that meiosis is controllable through external manipulations of the cell culture. One especially advantageous host cell type is one where the cells can be manipulated through external manipulations into different mating types.

The genome of a number of species have already been sequenced more or less completely and the sequences can be found in databases. The list of species for which the whole genome has been sequenced increases constantly. Preferably the host cell is selected from the group of species, for which the whole genome or essentially the whole genome has been sequenced. The host cell should preferably be selected from a species that is well described in the literature with respect to genetics, metabolism, physiology such as model organism used for genomics research.

The host organism should preferably be conditionally deficient in the abilities to undergo homologous recombination. The host organism should preferably have a codon usage similar to that of the donor organisms. Furthermore, in the case of genomic DNA, if eukaryotic donor organisms are used, it is preferable that the host organism has the ability to process the donor messenger RNA properly, e.g., splice out introns.

The host cells can be bacterial, archaebacteria, or eukaryotic and can constitute a homogeneous cell line or mixed culture. Suitable cells include the bacterial and eukaryptic cell lines commonly used in genetic engineering and protein expression.

Preferred prokaryotic host organisms may include but are not limited to *Escherichia coli, Bacillus subtilis, B licehniformis, B. cereus, Streptomyces lividans, Streptomyces coelicolor, Pseudomonas aeruginosa, Myxococcus xanthus. Rhodococcus, Streptomycetes, Actinomycetes, Corynebacteria, Bacillus, Pseudomonas, Salmonella*, and *Erwinia*. The complete genome sequences of *E. coli* and *Bacillus subtilis* are described by Blattner et al., Science 277, 1454-1462 (1997); Kunst et al., Nature 390, 249-256 (1997)).

Preferred eukaryotic host organisms are mammals, fish, insects, plants, algae and fungi.

Examples of mammalian cells include those from, e.g., monkey, mouse, rat, hamster, primate, and human, both cell lines and primary cultures. Preferred mammalian host cells include but are not limited to those derived from humans, monkeys and rodents, such as chinese hamster ovary (CHO) cells, NIH/3T3, COS, 293, VERO, HeLa etc (see Kriegler M. in "Gene Transfer and Expression: A Laboratory Manual", New York, Freeman & Co. 1990), and stem cells, including embryonic stem cells and hemopoietic stem cells, zygotes, fibroblasts, lymphocytes, kidney, liver, muscle, and skin cells.

Examples of insect cells include *baculo lepidoptera.*

Examples of plant cells include maize, rice, wheat, cotton, soybean, and sugarcane. Plant cells such as those derived from Nicotiana and Arabidopsis are preferred.

Examples of fungi include *penicillium, aspergillus*, such as *Aspergillus nidulans, podospora, neurospora*, such as *Neurospora crassa, saccharomyces*, such as *Saccharomyces cerevisiae* (budding yeast), *Schizosaccharomyces*, such as *Schizosaccharomyces pombe* (fission yeast), *Pichia* spp, such as *Pichia pastoris*, and *Hansenula polymorpha* (methylotropic yeasts).

In a preferred embodiment the host cell is a yeast cell, and an illustrative and not limiting list of suitable yeast host cells comprise: baker's yeast, *Kluyveromyces marxianus, K. lactis, Candida utilis, Phaffia rhodozyma, Saccharomyces boulardii, Pichia pastoris, Hansenula polymorpha, Yarrowia lipolytica, Candida paraffinica, Schwanniomyces castellii, Pichia stipitis, Candida shehatae, Rhodotorula glutinis, Lipomyces lipofer, Cryptococcos curvatus, Candida* spp. (e.g. *C. palmioleophila*), *Yarrowia lipolytica, Candida guilliermondii, Candida, Rhodotorula* spp., *Saccharomycopsis* spp., *Aureobasidium pullulans, Candida brumptii, Candida hydrocarbofumarica, Torulopsis, Candida tropicalis, Saccharomyces cerevisiae, Rhodotorula rubra, Candida flaveri, Eremothecium ashbyii, Pichia* spp., *Pichia pastoris, Kluyveromyces, Hansenula, Kloeckera, Pichia, Pachysolen* spp., or *Torulopsis bombicola.*

The choice of host will depend on a number of factors, depending on the intended use of the engineered host, including pathogenicity, substrate range, environmental hardiness, presence of key intermediates, ease of genetic manipulation, and likelihood of promiscuous transfer of genetic information to other organisms. Particularly advantageous hosts are *E. coli, lactobacilli, Streptomycetes, Actinomycetes, Saccharomyces* and filamentous fungi.

In any one host cell it is possible to make all sorts of combinations of expressible nucleotide sequences from all possible sources. Furthermore, it is possible to make combinations of promoters and/or spacers and/or introns and/or terminators in combination with one and the same expressible nucleotide sequence.

Thus in any one cell there may be expressible nucleotide sequences from two different expression states. Furthermore, these two different expression states may be from one species or advantageously from two different species. Any one host cell may also comprise expressible nucleotide sequences from at least three species, such as from at least four, five, six, seven, eight, nine or ten species, or from more than 15 species such as from more than 20 species, for example from more than 30, 40 or 50 species, such as from more than 100 different species, for example from more than 300 different species, such as form more than 500 different species, for example from more than 1000 different species, thereby obtaining combinations of large numbers of expressible nucleotide sequences from a large number of species. In this way potentially unlimited numbers of combinations of expressible nucleotide sequences can be combined across different expression states. These different expression states may represent at least two different tissues, such as at least two organs, such as at least two species, such as at least two genera. The different species may be from at least two different phylae, such as from at least two different classes, such as from at least two different divisions, more preferably from at least two different sub-kingdoms, such as from at least two different kingdoms.

Any two of these species may be from two different classes, such as from two different divisions, more preferably from two different sub-kingdoms, such as from two different kingdoms. Thus expressible nucleotide sequences may be combined from a eukaryot and a prokaryot into one and the same cell.

According to another embodiment of the invention, the expressible nucleotide sequences may be from one and the same expression state. The products of these sequences may interact with the products of the genes in the host cell and form new enzyme combinations leading to novel biochemical pathways. Furthermore, by putting the expressible nucleotide sequences under the control of a number of promoters it becomes possible to switch on and off groups of genes in a coordinated manner. By doing this with expressible nucleotide sequences from only one expression states, novel combinations of genes are also expressed.

The number of concatemers in one single cell may be at least one concatemer per cell, preferably at least 2 concatemers per cell, more preferably 3 per cell, such as 4 per cell, more preferably 5 per cell, such as at least 5 per cell, for example at least 6 per cell, such as 7, 8, 9 or 10 per cell, for example more than 10 per cell. As described above, each concatemer may preferably comprise up to 1000 cassettes, and it is envisages that one concatemer may comprise up to 2000 cassettes. By inserting up to 10 concatemers into one single cell, this cell may thus be enriched with up to 20,000 heterologous expressible genes, which under suitable conditions may be turned on and off by regulation of the regulatable promoters.

Often it is more preferable to provide cells having anywhere between 10 and 1000 heterologous genes, such as 20-900 heterologous genes, for example 30 to 800 heterologous genes, such as 40 to 700 heterologous genes, for example 50 to 600 heterologous genes, such as from 60 to 300 heterologous genes or from 100 to 400 heterologous genes which are inserted as 2 to 4 artificial chromosomes each containing one concatemer of genes. The genes may advantageously be located on 1 to 10 such as from 2 to 5 different concatemers in the cells. Each concatemer may advantageously comprise from 10 to 1000 genes, such as from 10 to 750 genes, such as from 10 to 500 genes, such as from 10 to 200 genes, such as from 20 to 100 genes, for example from 30 to 60 genes, or from 50 to 100 genes.

The concatemers may be inserted into the host cells according to any known transformation technique, preferably according to such transformation techniques that ensure stable and not transient transformation of the host cell. The concatemers may thus be inserted as an artificial chromosome which is replicated by the cells as they divide or they may be inserted into the chromosomes of the host cell. The concatemer may also be inserted in the form of a plasmid such as a plasmid vector, a phage vector, a viral vector, a cosmid vector, that is replicated by the cells as they divide. Any combination of the three insertion methods is also possible. One or more concatemers may thus be integrated into the chromosome(s) of the host cell and one or more concatemers may be inserted as plasmids or artificial chromosomes. One or more concatemers may be inserted as artificial chromosomes and one or more may be inserted into the same cell via a plasmid.

EXAMPLES

Example 1

In the examples 1-3 an AscI site was introduced into the EcoR1 site in pYAC4 (Sigma, Burke DT et al. 1987, Science vol 236, p 806), so that sticky ends match the AscI site(=RS2 in general formula of this patent) of the cassettes in pEVE vectors Preparation of EVACs (EVolvable Artificial Chromosomes) Including Size Fractioning Preparation of PYAC4-Asc Arms
1. inoculate 150 ml of LB (sigma) with a single colony of *E. coli* DH5α containing pYAC4-Asc
2. grow to OD600~1, harvest cells and make plasmid preparation
3. digest 100 µg pYAC4-Asc w. BamHI and AscI
4. dephosphorylate fragments and heat inactivate phosphatase(20 min, 80 C)
5. purify fragments(e.g. Qiaquick Gel Extraction Kit)
6. run 1% agarose gel to estimate amount of fragment Preparation of Expression Cassettes
1. take 100 µg of plasmid preparation from each of the following libraries
a) pMA-CAR
b) pCA-CAR
c) Phaffia cDNA library
d) Carrot-cDNA library
2. digest w. SrfI (10 units/prep, 37 C overnight)
3. dephosphorylate (10 units/prep, 37 C, 2h)
4. heat inactivate 80 C, 20 min
5. concentrate and change buffer (precipitation or ultra filtration),
6. digest w. AscI. (10 units/prep, 37 C, overnight)
7. adjust volume of preps to 100 µL Preparation of EVACs
Different types of EVACs have been made by varying the ratio of the different libraries that goes into the ligation reaction.

| EVAC | pMA-CAR | pCA-CAR | Phaffia cDNA | Carrot cDNA |
|------|---------|---------|--------------|-------------|
| A    | 40%     | 40%     | 10%          | 10%         |
| B    | 25%     | 25%     | 25%          | 25%         |

1. add ~100 ng arms of pYAC4-Asc/100 µg of cassette mixture
2. concentrate to<33.5 µL
3. add 2.5 units of T4 DNA-ligase+4 µL 10× ligase buffer. Adjust to 40 µL
4. ligate 3 h, 16 C
5. stop reaction by adding 2 µL of 500 mM EDTA
6. bring reaction volume to 125 µL, add 25 µL loading mix, heat at 60 C for 5 min
7. distribute evenly in 10 wells of a 1% LMP agarose gel
8. run pulsed field gel (CHEF III, 1% LMP agarose, ½ strength TBE (BioRad), angle 120, temperature 12 C, voltage 5.6V/cm, switch time ramping 5-25 s, run time 30 h)
9. stain part of the gel that contains molecular weight markers+1 sample lane for quality check
10. cut remaining 9 sample lanes corresponding to mw. 97-194 kb(fraction 1); 194-291 kb(fraction 2); 291-365 kb(fraction 3) from the gel
11. agarase gel in high NaCl agarase buffer. 1 U agarase/ 100 µg gel. 40 C 3 h
12. concentrate preparation to<20 µL
13. transform suitable yeast strain w. preparation using alkali/cation transformation
14. plate on selective minimal media plates
15. incubate 30 C for 4-5 days
16. pick colonies
17. analyse colonies Example 2

Preparation of EVACs (EVolvable Artificial Chromosomes) with Direct Transformation Preparation of pYAC4-Asc Arms
1. inoculate 150 ml of LB with a single colony of DH5α containing pYAC4-Asc
2. grow to OD600~1, harvest cells and make plasmid preparation
3. digest 100 µg pYAC4Asc w. BamHI and AscI
4. dephosphorylate fragments and heat inactivate phosphatase(20 min, 80 C)
5. purify fragments(e.g. Qiaquick Gel Extraction Kit)
1. run 1% agarose gel to estimate amount of fragment Preparation of Expression Cassettes
1. take 100 µg of plasmid preparation from each of the following libraries
e) pMA-CAR
f) pCA-CAR
g) Phaffia cDNA library
h) Carrot cDNA library
2. digest w. SrfI (10 units/prep, 37 C overnight)
3. dephosphorylate (10 units/prep, 37 C, 2 h)
4. heat inactivate 80 C, 20 min
5. concentrate and change buffer (precipitation or ultra filtration),
6. digest w. AscI. (10 units/prep, 37 C, overnight)
7. adjust volume of preps to 100 µL Preparation of EVACs
Different types of EVACs have been made by varying the ratio of the different libraries that goes into the ligation reaction.

| EVAC | pMA-CAR | pCA-CAR | Phaffia cDNA | Carrot cDNA |
|------|---------|---------|--------------|-------------|
| A    | 40%     | 40%     | 10%          | 10%         |
| B    | 25%     | 25%     | 25%          | 25%         |

1. concentrate to<32 µL
2. add 1 unit of T4 DNA-ligase+4 µL 10× ligase buffer. Adjust to 40 µL
3. ligate2 h, 16 C 4. stop reaction by adding 2 μL of 500 mM EDTA, heat inactivate 60 C, 20 min
5. bring reaction volume to 500 μL with dH₂O, concentrate to 30 μL
6. add 10 U AscI, 4 μL 10×AscI buffer, bring to 40 μL
7. incubate at 37 C for 1 h (alternatively 15 min 30 min)
8. heat inactivate 60 C, 20 min
9. add 2 μg YAC4-Asc arms, 1 U T4 DNA ligase, 10 μL 10× ligase buffer, bring to 100 μL
10. incubate ON, 16 C
11. add water to 500 μL
12. concentrate to 25 μL
13. transform suitable yeast strain w. preparation using alkali/cation transformation or other suitable transformation method
14. plate on selective minimal media plates
5. incubate 30 C for 4-5 days
6. pick colonies
17. analyse colonies Example 3

Preparation of EVACs (EVolvable Artificial Chromosomes) (Small Scale Preparation)

Preparation of Expression Cassettes
1. inoculate 5 ml of LB-medium (Sigma) with library inoculum corresponding to a 10+ fold representation of library. Grow overnight
2. make plasmid miniprep from 1.5 ml of culture (E.g. Qiaprep spin miniprep kit)
3. digest plasmid w. SrfI
4. dephosphorylate fragments and heat inactivate phosphatase(20 min, 80 C)
5. digest w. AscI
6. run ⅟₁₀ of reaction in 1% agarose to estimate amount of fragment Preparation of pYAC4-Asc Arms
1. inoculate 150 ml of LB with a single colony of *E. coli* DH5α containing pYAC4-Asc
2. grow to OD600~1, harvest cells and make plasmid preparation
3. digest 100 μg pYAC4-Asc w. BamHI and AscI
4. dephosphorylate fragments and heat inactivate phosphatase(20 min, 80 C)
5. purify fragments(E.g. Qiaquick Gel Extraction Kit)
6. run 1% agarose gel to estimate amount of fragment Preparation of EVACs
1. mix expression cassette fragments with YAC-arms so that cassette/arm ration is ~1000/1
2. if needed concentrate mixture(use e.g. Microcon YM30) so fragment concentration>75 ng/μL reaction
3. add 1 U T4 DNA ligase, incubate 16 C, 1-3 h. Stop reaction by adding 1 μL of 500 mM EDTA
4. run pulsed field gel (CHEF III, 1% LMP agarose, ½ strength TBE, angle 120, temperature 12 C, voltage 5.6V/cm, switch time ramping 5-25 s, run time 30 h) Load sample in 2 lanes.
5. stain part of the gel that contains molecular weight markers
6. cut sample lanes corresponding to mw. 100-200 kb
7. agarase gel in high NaCl agarase buffer. 1 U agarase/100 mg gel
8. concentrate preparation to<20 μL
9. transform suitable yeast strain w. preparation using electroporation;
10. plate on selective minimal media plates
11. incubate 30 C for 4-5 days
12. pick colonies Example 4 cDNA Libraries Used in the Production of EVACs

1. *Daucus carota*, carrot root library:
   Full length
   Oligo dT primed, directional cDNA library
   cDNA library made using a pool of 3 Evolva EVE 4, 5 & 8 vectors (FIG. 4, 5, 6)
   Number of independent clones: 41.6×10⁶
   Average size: 0.9-2.9 kb
   Number of different genes present: 5000-10000
2. *Xanthophyllomyces dendrorhous*, (yeast), hole organism library
   Full length
   Oligo dT primed, directional cDNA library
   cDNA library made using a pool of 3 Evolva EVE 4, 5 & 8 vectors (FIG. 4, 5, 6)
   Number of independent clones: 48.0×10⁶
   Average size: 1.0-3.8 kb
   Number of different genes present: 5000-10000
3. Target carotenoid gene cDNA library
   Full length and normalised
   Directional cDNA cloning
   Library made by cloning each gene individually in 2 Evolva EVE 4, 5 & 8 vectors (FIG. 4, 5, 6)
   Number of different genes: 48
   Species and genes used:
   *Gentiana* sp., ggps, psy, pds, zds, lcy-b, lcy-e, bhy, zep
   *Rhodobacter capsulatus*, idi, crtC, crtF
   *Erwinia uredovora*, crtE, crtB, crtI, crtY, crtz
   *Nostoc anabaena*, zds
   *Synechococcus* PCC7942, pds
   *Erwinia herbicola*, crtE, crtB, crtI, crtY, crtZ
   *Staphylococcus aureus*, crtM, crtN
   *Xanthophyllomyces dendrorhous*, crtI, crtYb
   *Capsicum annuum*, ccs, crtL
   *Nicotiana tabacum*, crtL, bchy
   *Prochlorococcus* sp., lcy-b, lcy-e
   *Saccharomyces cerevisiae*, idi
   *Corynebacterium* sp., crtI, crtYe, crtYf, crtEb
   *Lycopersicon esculentum*, psy-1
   *Neurospora crassa*, al1

Example 5

Transformation of EVACs

Example 5a

Transformation

1. Inoculate a single colony into 100 ml YPD broth and grow with aeration at 30° C. to mid log, 2×10⁶ to 2×10⁷ cells/ml.
2. Spin to pellet cells at 400× g for 5 minutes; discard supernatant.
3. Resuspend cells in a total of 9 ml TE, pH 7.5. Spin to pellet cells and discard supernatant.
4. Gently resuspend cells in 5 ml 0.1 M Lithium/Cesium Acetate solution, pH 7.5.
5. Incubate at 30° C. for 1 hour with gentle shaking.
6. Spin at 400× g for 5 minutes to pellet cells and discard supernatant.

7. Gently resuspend in 1 ml TE, pH 7.5. Cells are now ready for transformation.
   8. In a 1.5 ml tube combine:
   100 µl yeast cells
   5 µl Carrier DNA (10 mg/ml)
   5 µl Histamine Solution
   ⅕ of an EVAC preparation in a 10 µl volume (max). (One EVAC preparation is made of 100 µg of concatenation reaction mixture)
   9. Gently mix and incubate at room temperature for 30 minutes.
   10. In a separate tube, combine 0.8 ml 50% (w/v) PEG 4000 and 0.1 ml TE and 0.1 ml of 1 M LiAc for each transformation reaction. Add 1 ml of this PEG/TE/LiAc mix to each transformation reaction. Mix cells into solution with gentle pipetting.
   11. Incubate at 30° C. for 1 hour.
   12. Heat shock at 42° C. for 15 minutes; cool to 30° C.
   13. Pellet cells in a microcentrifuge at high speed for 5 seconds and remove supernatant.
   14. Resuspend in 200 µl of rich media and plate in appropriate selective media
   15. Incubate at 30° C. for 48-72 hours until transformant colonies appear.

Example 5b

Transformation of EVACs Using Electroporation 100 ml of YPD is inoculated with one yeast colony and grown to $OD_{600}$=1.3 to 1.5. The culture is harvested by centrifuging at 4000× g and 4° C. The cells are resuspended in 16 ml sterile $H_2O$. Add 2 ml 10×TE buffer, pH 7.5 and swirl to mix. Add 2 ml 10× lithium acetate solution (1 M, pH 7.5) and swirl to mix. Shake gently 45 min at 30° C. Add 1.0 ml 0.5 M DTE while swirling. Shake gently 15 min at 30° C. The yeast suspension is diluted to 100 ml with sterile water. The cells are washed and concentrated by centrifuging at 4000× g, resuspending the pellet in 50 ml ice-cold sterile water, centrifuging at 4000× g, resuspending the pellet in 5 ml ice-cold sterile water, centrifuging at 4000× g and resuspending the pellet in 0.1 ml ice-cold sterile 1 M sorbitol. The electroporation was done using a Bio-Rad Gene Pulser. In a sterile 1.5-ml microcentrifuge tube 40 µl concentrated yeast cells were mixed with 5 µl 1:10 diluted EVAC preparation. The yeast-DNA mix is transferred to an ice-cold 0.2-cm-gap disposable electroporation cuvette and pulsed at 1.5 kV, 25 µF, 200 Ω. 1 ml ice-cold 1 M sorbitol is added to the cuvette to recover the yeast. Aliquots are spread on selective plates containing 1 M sorbitol. Incubate at 30° C. until colonies appear.

Example 6

Rare Restriction Enzymes with Recognition Sequence and Cleavage Points

In this example, rare restriction enzymes are listed together with their recognition sequence and cleavage points. (^) indicates cleavage points 5'-3' sequence and (_) indicates cleavage points in the complementary sequence.
W=A or T; N=A, C, G or T

| | |
|---|---|
| 6a) | Unique, palindromic overhang |
| AscI | GG^CGCG_CC |
| AsiSI | GCG_AT^CGC |
| CciNI | GC^GGCC_GC |
| CspBI | GC^GGCC_GC |
| FseI | GG_CCGG^CC |
| MchAI | GC^GGCC_GC |
| NotI | GC^GGCC_GC |
| PacI | TTA_AT^TAA |
| SbfI | CC_TGCA^GG |
| SdaI | CC_TGCA^GG |
| SgfI | GCG_AT^CGC |
| SgrAI | CR^CCGG_YG |
| Sse232I | CG^CCGG_CG |
| Sse8387I | CC_TGCA^GG |
| 6b) | No overhang |
| BstRZ246I | ATTT^AAAT |
| BstSWI | ATTT^AAAT |
| MspSWI | ATTT^AAAT |
| MssI | GTTT^AAAC |
| PmeI | GTTT^AAAC |
| SmiI | ATTT^AAAT |
| SrfI | GCCC^GGGC |
| SwaI | ATTT^AAAT |
| 6c) | Non-palindromic and/or variable overhang |
| AarI | CACCTGCNNNN^NNNN_ (SEQ ID NO: 5) |
| AbeI | CC^TCA_GC |
| AloI | ^NNNNN_NNNNNNNGAACNNNNNNNTCCNNNNNNNN_NNNNN^ (SEQ ID NO: 6) |
| BaeI | ^NNNNN_NNNNNNNNNNACNNNNGTAYCNNNNNNNN_NNNNN^ (SEQ ID NO: 7) |
| BbvCI | CC^TCA_GC |
| CpoI | CG^GWC_CG |
| CspI | CG^GWC_CG |
| Pfl27I | RG^GWC_CY |
| PpiI | ^NNNNN_NNNNNNNGAACNNNNNCTCNNNNNNNN_NNNNN^ (SEQ ID NO: 8) |
| PpuMI | RG^GWC_CY |
| PpuXI | RG^GWC_CY |
| Psp5II | RG^GWC_CY |
| PspPPI | RG^GWC_CY |
| RsrII | CG^GWC_CG |
| Rsr2I | CG^GWC_CG |

-continued

| | |
|---|---|
| SanDI | GG^GWC_CC |
| SapI | GCTCTTCN^NNN_<br>(SEQ ID NO: 9) |
| SdiI | GGCCN_NNN^NGGCC<br>(SEQ ID NO: 10) |
| SexAI | A^CCWGG_T |
| SfiI | GGCCN_NNN^NGGCC<br>(SEQ ID NO: 11) |
| Sse1825I | GG^GWC_CC |
| Sse8647I | AG^GWC_CT |
| VpaK32I | GCTCTTCN^NNN_<br>(SEQ ID NO: 12) |
| 6d) | Meganucleases |
| I-Sce I | TAGGGATAA_CAGG^GTAAT<br>(SEQ ID NO: 13) |
| I-Ceu I | ACGGTC_CTAA^GGTAG<br>(SEQ ID NO: 14) |
| I-Cre I | AAACGTC_GTGA^GACAGTTT<br>(SEQ ID NO: 15) |
| I-Sce II | GGTC_ACCC^TGAAGTA<br>(SEQ ID NO: 16) |
| I-Sce III | GTTTTGG_TAAC^TATTTAT<br>(SEQ ID NO: 17) |
| Endo.<br>Sce I | GATGCTGC_AGGC^ATAGGCTTGTTTA<br>(SEQ ID NO: 18) |
| PI-Sce I | GG_GTGC^GGAGAA<br>(SEQ ID NO: 19) |
| PI-Psp I | TGGCAAACAGCTA_TTAT^GGGTATTATGGGT<br>(SEQ ID NO: 20) |
| I-Ppo I | CTCTC_TTAA^GGTAG<br>(SEQ ID NO: 21) |
| HO | TTTCCGC_AACA^GT<br>(SEQ ID NO: 22) |
| I-Tev I | NN_NN^NNTCAGTAGATGTTTTTCTTGGTCTACCGTTT<br>(SEQ ID NO: 23) |

More meganucleases have been identified, but their precise sequence of recognition has not been determined, see e.g. www DOT meganuclease DOT com (URL inactivated in accordance with 37 CFR 1.57(d) by replacement of "." with "DOT".)

Example 7

Concatemer Size Limitation Experiments (use of Stoppers)

Materials Used:

pYAC4 (Sigma. Burke et al. 1987, science, vol 236, p 806) was digested w. EcoR1 and BamHI and dephosphorylated pSE420 (invitrogen) was linearised using EcoR1 and used as the model fragment for concatenation.

T4 DNA ligase (Amersham-pharmacia biotech) was used for ligation according to manufacturers instructions.

Method: Fragments and arms were mixed in the ratios (concentrations are arbitrary units) indicated on FIGS. 9a and 9b. Ligation was allowed to proceed for 1 h at 16 C. Reaction was stopped by the addition of 1 µL 500 mM EDTA. Products were analysed by standard agarose GE (1% agarose, ½ strength TBE) or by PFGE(CHEF III, 1% LMP agarose, ½ strength TBE, angle 120, temperature 12 C, voltage 5.6V/cm, switch time ramping 5-25 s, run time 30 h)

The results are shown in FIG. 9, wherein it is shown that the size of concatemers is proportional to the ratio of cassettes per YAC arms.

Example 8

Integration of Expression Cassettes into Artificial Chromosomes

Integration of expression cassettes into YAC12 was done essentially as done by Sears D. D., Hieter P., Simchen G., Genetics, 1994, 138, 1055-1065.

An AscI site was introduced into the Bgl II site of the integration vectors pGS534 and pGS525.

A β-galactosidase gene, as well as crtE, crtB, crtI and crtY from *Erwinia Uredovora* were cloned into pEVE4. These expression cassettes were ligated into AscI of the modified integration vectors pGS534 and pGS525.

Linearised pGS534 and pGS525 containing the expression cassettes were transformed into haploid yeast strains containing the appropriate target YAC which carries the Ade" gene. Red Ade-transformants were selected (the parent host strain is red due to the ade2-101 mutation).

Additional confirmation of correct integration of the β-galactosidase expression cassette was done using a β-galactosidase assay.

Example 9

Re-transformation of Cells that already Contain Artificial Chromosomes to Obtain at least 2 Artificial Chromosomes per Cell Yeast strains containing YAC12, Sears D. D., Hieter P., Simchen G., Genetics, 1994, 138, 1055-1065 were transformed with EVACs following the protocol described in example 4a. The transformed cells were plated on plates that select for cells that contained both YAC12 and EVACs.

Example 10

Example of Different Expression Patterns "Phenotypes" Obtained using the Same Yeast Clones Under Different Expression Conditions Colonies were picked with a sterile toothpick and streaked sequentially onto plates corresponding to the four repressed and/or induced conditions (-Ura/-Trp, -Ura/-Trp/-Met, -Ura/-Trp/+200 µM $Cu_2SO_4$, -Ura/-Trp/-Met/+200 µM $CU_2SO_4$). 20 mg adenin was added to the media to suppress the ochre phenotype.

The invention claimed is:

1. A library comprising a collection of individual cells, the cells being denoted $cell_1, cell_2, \ldots,$ wherein $i \geq 2$, each cell comprising
a concatemer of individual oligonucleotide cassettes, said concatemer comprising
a nucleotide sequence of the following formula:

$[rs_2\text{-SP--PR-X-TR-SP-}rs_1]_n$ wherein $rs_1$ and $rs_2$ together comprise a rare cutting restriction site, denoted $rs_1$-$rs_2$, comprising a recognition sequence of 7 to 38 bases where substantially all restriction sites are complete restriction sites recognized by the same enzyme,
SP denotes a spacer of 2 to 2500 bases,
X denotes an expressible nucleotide sequence,
PR denotes a promoter capable of regulating the expression of X in the cell,
TR denotes a terminator, and
$n \geq 2$
and wherein at least one concatemer of $cell_1$ is different from a concatemer of $cell_2$.

2. The library according to claim 1, wherein said cells are yeast cells, said yeast being selected from the group consisting of budding yeast, *Phaffia rhodozyma*, *Saccharomyces boulardii*, *Yarrowia lipolytica*, *Schwanniomyces castellii*, *Rhodotorula glutinis*, *Lipomyces lipofer*, *Cryptococcos curvatus*, *Candida* spp., *Rhodotorula* spp., *Saccharomyces* spp., *Aureobasidium pullulans*, *Torulopsis* spp., *Saccharomyces cerevisiae*, *Eremothecium ashbyii*, *Pichia* spp., *Kluyveromyces* spp., *Hansenula* spp., *Kloeckera* spp., and *Pachysolen* spp., and mutants thereof.

3. The library according to claim 1, wherein at least one cassette in one cell comprises an intron between the promoter and the expressible nucleotide sequence.

4. The library according to claim 1, wherein at least two expressible nucleotide sequences come from different expression states or tissues.

5. The library according to claim 1, wherein at least one concatemer is integrated into an artificial or host chromosome in the host cell.

6. The library according to claim 1, wherein the PR is an externally controllable promoter.

7. A method of producing a library comprising a collection of individual cells, comprising the steps:
i) providing a population of nucleotide cassettes having the general formula $[rs_2\text{--SP-PR-X-TR-SP-}rs_1]$, wherein $rs_1$ and $rs_2$ together comprise a rare cutting restriction site, denoted $rs_1$-$rs_2$, comprising a recognition sequence of 7 to 38 bases where substantially all restriction sites are complete restriction sites recognized by the same enzyme,
SP denotes a spacer of 2 to 2500 bases,
X denotes an expressible nucleotide sequence,
PR denotes a promoter capable of regulating the expression of X in the cell, and
TR denotes a terminator,
ii) assembling random subsets of the cassettes into concatemers comprising at least two cassettes,
iii) ligating the concatemers into vectors,
iv) introducing the vectors into host cells, and
v) mixing at least two cells so that at least one concatemer of a first cell comprises a random sub-set of cassettes being different from a random sub-set of cassettes of a concatemer of a second cell.

8. The method according to claim 7, whereby the vectors comprise an artificial chromosome.

9. An expression library obtainable by the method of claim 7.

10. An expression library obtainable by the method of claim 8.

11. The expression library of claim 1, wherein the $rs_1$ and $rs_2$ together comprise a rare cutting restriction site, denoted $rs_1$-$rs_2$, comprising a recognition sequence of 8 to 38 bases.

12. The expression library of claim 1, wherein the $rs_1$ and $rs_2$ together comprise a rare cutting restriction site, denoted $rs_1$-$rs_2$, comprising a recognition sequence of 10 to 38 bases.

13. The expression library of claim 1, wherein the $rs_1$ and $rs_2$ together comprise a rare cutting restriction site, denoted $rs_1$-$rs_2$, which is cleavable by a restriction enzyme to leave a unique palindromic overhang.

* * * * *

SEQUENCE LISTING

<160> NUMBER OF SEQ ID NOS: 23

<210> SEQ ID NO 1
<211> LENGTH: 3417
<212> TYPE: DNA
<213> ORGANISM: Artificial
<220> FEATURE:
<223> OTHER INFORMATION: Synthetic
<220> FEATURE:
<221> NAME/KEY: promoter
<222> LOCATION: (49)..(437)
<223> OTHER INFORMATION: Met25 promoter
<220> FEATURE:
<221> NAME/KEY: terminator
<222> LOCATION: (495)..(823)
<223> OTHER INFORMATION: ADH1
<220> FEATURE:
<221> NAME/KEY: rep_origin
<222> LOCATION: (959)..(1899)
<223> OTHER INFORMATION: ColE1
<220> FEATURE:
<221> NAME/KEY: misc_feature
<222> LOCATION: (1902)..(2759)
<223> OTHER INFORMATION: Ampicillin resistance gene
<220> FEATURE:
<221> NAME/KEY: misc_feature
<222> LOCATION: (2891)..(3347)
<223> OTHER INFORMATION: f1-phage origin of replication

<400> SEQUENCE: 1

| | | | | | | |
|---|---|---|---|---|---|---|
| ctgatttgcc | cgggcagttc | aggctcatca | ggcgcgccat | gcagggattc | ttcggatgca | 60 |
| agggttcgaa | tcccttagct | ctcattattt | tttgctttt | ctcttgaggt | cacatgatcg | 120 |
| caaaatggca | aatggcacgt | gaagctgtcg | atattgggga | actgtggtgg | ttggcaaatg | 180 |
| actaattaag | ttagtcaagg | cgccatcctc | atgaaaactg | tgtaacataa | taaccgaagt | 240 |
| gtcgaaaagg | tggcaccttg | tccaattgaa | cacgctcgat | gaaaaaaata | agatatatat | 300 |
| aaggttaagt | aaagcgtctg | ttagaaagga | agttttttcct | ttttcttgct | ctcttgtctt | 360 |
| ttcatctact | atttccttcg | tgtaatacag | ggtcgtcaga | tacatagata | caattctatt | 420 |
| accccccatcc | atacaagctt | ggcgcgaat | tcgtcgaccc | ggggatccgc | ggccgcaggc | 480 |
| ctaaattgat | ctagagcttt | ggacttcttc | gccagaggtt | tggtcaagtc | tccaatcaag | 540 |
| gttgtcggct | tgtctaccctt | gccagaaatt | tacgaaaaga | tggaaaaggg | tcaaatcgtt | 600 |
| ggtagatacg | ttgttgacac | ttctaaataa | gcgaatttct | tatgatttat | gatttttatt | 660 |
| attaaataag | ttataaaaaa | aataagtgta | tacaaatttt | aaagtgactc | ttaggtttta | 720 |
| aaacgaaaat | tcttgttctt | gagtaactct | ttcctgtagg | tcaggttgct | ttctcaggta | 780 |
| tagcatgagg | tcgctcttat | tgaccacacc | tctaccggca | tgcccatggg | ttaactgatc | 840 |
| aatgcatcct | gcatggcgcg | cctgatgagc | ctgaactgcc | cgggcaaatc | agctggacgt | 900 |
| ctgcctgcat | taatgaatcg | gccaacgcgc | ggggagaggc | ggtttgcgta | ttgggcgctc | 960 |
| ttccgcttcc | tcgctcactg | actcgctgcg | ctcggtcgtt | cggctgcggc | gagcggtatc | 1020 |
| agctcactca | aaggcggtaa | tacggttatc | cacagaatca | ggggataacg | caggaaagaa | 1080 |
| catgtgagca | aaaggccagc | aaaaggccag | gaaccgtaaa | aaggccgcgt | tgctggcgtt | 1140 |
| tttccatagg | ctccgccccc | ctgacgagca | tcacaaaaat | cgacgctcaa | gtcagaggtg | 1200 |
| gcgaaacccg | acaggactat | aaagatacca | ggcgtttccc | cctggaagct | ccctcgtgcg | 1260 |
| ctctcctgtt | ccgaccctgc | cgcttaccgg | atacctgtcc | gcctttctcc | cttcgggaag | 1320 |
| cgtggcgctt | tctcatagct | cacgctgtag | gtatctcagt | tcggtgtagg | tcgttcgctc | 1380 |

```
caagctgggc tgtgtgcacg aaccccccgt tcagcccgac cgctgcgcct tatccggtaa    1440
ctatcgtctt gagtccaacc cggtaagaca cgacttatcg ccactggcag cagccactgg    1500
taacaggatt agcagagcga ggtatgtagg cggtgctaca gagttcttga agtggtggcc    1560
taactacggc tacactagaa ggacagtatt tggtatctgc gctctgctga agccagttac    1620
cttcggaaaa agagttggta gctcttgatc cggcaaacaa accaccgctg gtagcggtgg    1680
tttttttgtt tgcaagcagc agattacgcg cagaaaaaaa ggatctcaag aagatccttt    1740
gatcttttct acggggtctg acgctcagtg gaacgaaaac tcacgttaag ggattttggt    1800
catgagatta tcaaaaagga tcttcaccta gatccttta aattaaaaat gaagttttaa    1860
atcaatctaa agtatatatg agtaaacttg gtctgacagt taccaatgct taatcagtga    1920
ggcacctatc tcagcgatct gtctatttcg ttcatccata gttgcctgac tccccgtcgt    1980
gtagataact acgatacggg agggcttacc atctggcccc agtgctgcaa tgataccgcg    2040
agacccacgc tcaccggctc cagatttatc agcaataaac cagccagccg aagggccga    2100 gcgcagaagt ggtcctgcaa ctttatccgc ctccatccag tctattaatt gttgccggga    2160
agctagagta agtagttcgc cagttaatag tttgcgcaac gttgttgcca ttgctacagg    2220
catcgtggtg tcacgctcgt cgtttggtat ggcttcattc agctccggtt cccaacgatc    2280
aaggcgagtt acatgatccc ccatgttgtg caaaaaagcg gttagctcct tcggtcctcc    2340
gatcgttgtc agaagtaagt tggccgcagt gttatcactc atggttatgg cagcactgca    2400
taattctctt actgtcatgc catccgtaag atgcttttct gtgactggtg agtactcaac    2460
caagtcattc tgagaatagt gtatgcggcg accgagttgc tcttgcccgg cgtcaatacg    2520
ggataatacc gcgccacata gcagaacttt aaaagtgctc atcattggaa aacgttcttc    2580
ggggcgaaaa ctctcaagga tcttaccgct gttgagatcc agttcgatgt aacccactcg    2640
tgcacccaac tgatcttcag catctttac tttcaccagc gtttctgggt gagcaaaaac    2700
aggaaggcaa aatgccgcaa aaaagggaat aagggcgaca cggaaatgtt gaatactcat    2760
actcttcctt tttcaatatt attgaagcat ttatcagggt tattgtctca tgagcggata    2820
catatttgaa tgtatttaga aaaataaaca atagggggtt ccgcgcacat ttccccgaaa    2880
agtgccacct gacgcgccct gtagcggcgc attaagcgcg gcgggtgtgg tggttacgcg    2940
cagcgtgacc gctacacttg ccagcgccct agcgcccgct cctttcgctt tcttcccttc    3000
ctttctcgcc acgttcgccg gctttccccg tcaagctcta aatcggggc tcccttagg    3060 gttccgattt agtgctttac ggcacctcga ccccaaaaaa cttgattagg gtgatggttc    3120
acgtagtggg ccatcgccct gatagacggt ttttcgccct tgacgttgg agtccacgtt    3180 ctttaatagt ggactcttgt tccaaactgg aacaacactc aaccctatct cggtctattc    3240
ttttgattta aagggatttt gccgatttc ggcctattgg ttaaaaaatg agctgattta    3300
acaaaaattt aacgcgaatt ttaacaaaat attaacgctt acaatttcca ttcgccattc    3360
aggctgcgca actgttggga agggcgatcg gtgcgggcct cttcgctatt acgccag     3417

<210> SEQ ID NO 2
<211> LENGTH: 3501
<212> TYPE: DNA
<213> ORGANISM: Artificial
<220> FEATURE:
<223> OTHER INFORMATION: Synthetic
<220> FEATURE:
<221> NAME/KEY: promoter
<222> LOCATION: (49)..(519)
```

```
<223> OTHER INFORMATION: Cup1 promoter
<220> FEATURE:
<221> NAME/KEY: terminator
<222> LOCATION: (579)..(907)
<223> OTHER INFORMATION: ADH1
<220> FEATURE:
<221> NAME/KEY: rep_origin
<222> LOCATION: (1043)..(1983)
<223> OTHER INFORMATION: ColE1
<220> FEATURE:
<221> NAME/KEY: misc_feature
<222> LOCATION: (1986)..(2843)
<223> OTHER INFORMATION: Ampicillin resistance gene
<220> FEATURE:
<221> NAME/KEY: misc_feature
<222> LOCATION: (2975)..(3431)
<223> OTHER INFORMATION: f1-phage origin of replication

<400> SEQUENCE: 2
ctgatttgcc cgggcagttc aggctcatca ggcgcgccat gcagggataa gccgatccca      60
ttaccgacat ttgggcgcta tacgtgcata tgttcatgta tgtatctgta tttaaaacac     120
ttttgtatta ttttttcctca tatatgtgta taggtttata cggatgattt aattattact    180
tcaccaccct ttatttcagg ctgatatctt agccttgtta ctagttagaa aaagacattt     240
ttgctgtcag tcactgtcaa gagattcttt tgctggcatt tcttctagaa gcaaaaagag     300
cgatgcgtct tttccgctga accgttccag caaaaaagac taccaacgca atatggattg     360
tcagaatcat ataaaagaga agcaaataac tccttgtctt gtatcaattg cattataata     420
tcttcttgtt agtgcaatat catatagaag tcatcgaaat agatattaag aaaaacaaac     480
tgtacaatca atcaatcaat catcacataa aatgttcaaa gcttggcgcc gaattcgtcg     540
acccggggat ccgcggccgc aggcctaaat tgatctagag cttggacttt cttcgccaga     600
ggtttggtca agtctccaat caaggttgtc ggcttgtcta ccttgccaga aatttacgaa     660
aagatggaaa agggtcaaat cgttggtaga tacgttgttg cacttctaa ataagcgaat     720 ttcttatgat ttatgatttt tattattaaa taagttataa aaaaaataag tgtatacaaa    780
ttttaaagtg actcttaggt tttaaaacga aaattcttgt tcttgagtaa ctctttcctg     840
taggtcaggt tgctttctca ggtatagcat gaggtcgctc ttattgacca cacctctacc    900
ggcatgccca tgggttaact gatcaatgca tcctgcatgg cgcgcctgat gagcctgaac     960
tgcccgggca atcagctgg acgtctgcct gcattaatga atcggccaac gcgcggggag    1020
aggcggtttg cgtattgggc gctcttccgc ttcctcgctc actgactcgc tgcgctcggt    1080
cgttcggctg cggcgagcgg tatcagctca ctcaaaggcg gtaatacggt tatccacaga    1140
atcaggggat aacgcaggaa agaacatgtg agcaaaaggc cagcaaaagg ccaggaaccg    1200
taaaaaggcc gcgttgctgg cgttttttcca taggctccgc cccctgacg agcatcacaa    1260 aaatcgacgc tcaagtcaga ggtggcgaaa cccgacagga ctataaagat accaggcgtt    1320
tccccctgga agctccctcg tgcgctctcc tgttccgacc ctgccgctta ccggatacct    1380
gtccgccttt ctcccttcgg gaagcgtggc gctttctcat agctcacgct gtaggtatct    1440
cagttcggtg taggtcgttc gctccaagct gggctgtgtg cacgaacccc ccgttcagcc    1500
cgaccgctgc gccttatccg gtaactatcg tcttgagtcc aacccggtaa gacacgactt    1560
atcgccactg gcagcagcca ctggtaacag gattagcaga gcgaggtatg taggcggtgc    1620
tacagagttc ttgaagtggt ggcctaacta cggctacact agaaggacag tatttggtat    1680
ctgcgctctg ctgaagccag ttaccttcgg aaaaagagtt ggtagctctt gatccggcaa    1740
acaaaccacc gctggtagcg gtggtttttt tgtttgcaag cagcagatta cgcgcagaaa    1800
```

```
aaaaggatct caagaagatc ctttgatctt ttctacgggg tctgacgctc agtggaacga    1860
aaactcacgt taagggattt tggtcatgag attatcaaaa aggatcttca cctagatcct    1920
tttaaattaa aaatgaagtt ttaaatcaat ctaaagtata tatgagtaaa cttggtctga    1980
cagttaccaa tgcttaatca gtgaggcacc tatctcagcg atctgtctat ttcgttcatc    2040
catagttgcc tgactcccg tcgtgtagat aactacgata cgggagggct taccatctgg     2100
ccccagtgct gcaatgatac cgcgagaccc acgctcaccg gctccagatt tatcagcaat    2160
aaaccagcca gccggaaggg ccgagcgcag aagtggtcct gcaactttat ccgcctccat    2220
ccagtctatt aattgttgcc gggaagctag agtaagtagt tcgccagtta atagtttgcg    2280
caacgttgtt gccattgcta caggcatcgt ggtgtcacgc tcgtcgtttg gtatggcttc    2340
attcagctcc ggttcccaac gatcaaggcg agttacatga tcccccatgt tgtgcaaaaa    2400
agcggttagc tccttcggtc ctccgatcgt tgtcagaagt aagttggccg cagtgttatc    2460
actcatggtt atggcagcac tgcataattc tcttactgtc atgccatccg taagatgctt    2520
ttctgtgact ggtgagtact caaccaagtc attctgagaa tagtgtatgc ggcgaccgag    2580
ttgctcttgc ccggcgtcaa tacgggataa taccgcgcca catagcagaa ctttaaaagt    2640
gctcatcatt ggaaaacgtt cttcggggcg aaaactctca aggatcttac cgctgttgag    2700
atccagttcg atgtaaccca ctcgtgcacc caactgatct tcagcatctt ttactttcac    2760
cagcgtttct gggtgagcaa aaacaggaag gcaaaatgcc gcaaaaaagg gaataagggc    2820
gacacggaaa tgttgaatac tcatactctt ccttttttcaa tattattgaa gcatttatca    2880
gggttattgt ctcatgagcg gatacatatt tgaatgtatt tagaaaaata aacaaatagg    2940
ggttccgcgc acatttcccc gaaaagtgcc acctgacgcg ccctgtagcg gcgcattaag    3000
cgcggcgggt gtggtggtta cgcgcagcgt gaccgctaca cttgccagcg ccctagcgcc    3060
cgctcctttc gctttcttcc cttcctttct cgccacgttc gccggctttc cccgtcaagc    3120
tctaaatcgg gggctccctt tagggttccg atttagtgct ttacggcacc tcgaccccaa    3180
aaaacttgat tagggtgatg gttcacgtag tgggccatcg ccctgataga cggtttttcg    3240
ccctttgacg ttggagtcca cgttctttaa tagtggactc ttgttccaaa ctggaacaac    3300
actcaaccct atctcggtct attcttttga tttataaggg attttgccga tttcggccta    3360
ttggttaaaa aatgagctga tttaacaaaa atttaacgcg aattttaaca aaatattaac    3420
gcttacaatt tccattcgcc attcaggctg cgcaactgtt gggaagggcg atcggtgcgg    3480
gcctcttcgc tattacgcca g                                              3501
```

```
<210> SEQ ID NO 3
<211> LENGTH: 4188
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (49)..(574)
<223> OTHER INFORMATION: lambda spacer DNA (22428-22923)
<220> FEATURE:
<221> NAME/KEY: promoter
<222> LOCATION: (582)..(969)
<223> OTHER INFORMATION: Met25 promoter
<220> FEATURE:
<221> NAME/KEY: terminator
<222> LOCATION: (1027)..(1355)
<223> OTHER INFORMATION: ADH1
<220> FEATURE:
```

```
<221> NAME/KEY: misc_feature
<222> LOCATION: (1365)..(1603)
<223> OTHER INFORMATION: ARS1 (autonomous replicating sequence) for
      Yeast replication
<220> FEATURE:
<221> NAME/KEY: rep_origin
<222> LOCATION: (1730)..(2670)
<223> OTHER INFORMATION: ColE1
<220> FEATURE:
<221> NAME/KEY: misc_feature
<222> LOCATION: (2673)..(3530)
<223> OTHER INFORMATION: Ampicillin resistance gene
<220> FEATURE:
<221> NAME/KEY: misc_feature
<222> LOCATION: (3662)..(4118)
<223> OTHER INFORMATION: f1-phage origin of replication

<400> SEQUENCE: 3
ctgatttgcc cgggcagttc aggctcatca ggcgcgccat gcagggattc tggaaattgc      60
aacgaaggaa gaaacctcgt tgctggaagc ctggaagaag tatcgggtgt tgctgaaccg     120
tgttgataca tcaactgcac ctgatattga gtggcctgct gtccctgtta tggagtaatc     180
gttttgtgat atgccgcaga acgttgtat gaaataacgt tctgcggtta gttagtatat     240
tgtaaagctg agtattggtt tatttggcga ttattatctt caggagaata atggaagttc     300
tatgactcaa ttgttcatag tgtttacatc accgccaatt gcttttaaga ctgaacgcat     360
gaaatatggt ttttcgtcat gttttgagtc tgctgttgat atttctaaag tcggtttttt     420
ttcttcgttt tctctaacta ttttccatga aatacatttt tgattattat ttgaatcaat     480
tccaattacc tgaagtcttt catctataat tggcattgta tgtattggtt tattggagta     540
gatgcttgct tttctgagcc atagctctga tatcagatct tcttcggatg caagggttcg     600
aatcccttag ctctcattat ttttttgcttt ttctcttgag gtcacatgat cgcaaaatgg     660
caaatggcac gtgaagctgt cgatattggg gaactgtggt ggttggcaaa tgactaatta     720
agttagtcaa ggcgccatcc tcatgaaaac tgtgtaacat aataaccgaa gtgtcgaaaa     780
ggtggcacct tgtccaattg aacacgctcg atgaaaaaaa taagatatat ataaggttaa     840
gtaaagcgtc tgttagaaag gaagtttttc ctttttcttg ctctcttgtc ttttcatcta     900
ctatttcctt cgtgtaatac agggtcgtca gatacataga tacaattcta ttaccccat    960 ccatacaagc ttggcgccga attcgtcgac ccggggatcc gcggccgcag gcctaaattg    1020
atctagagct ttggacttct tcgccagagg tttggtcaag tctccaatca aggttgtcgg    1080
cttgtctacc ttgccagaaa tttacgaaaa gatggaaaag ggtcaaatcg ttggtagata    1140
cgttgttgac acttctaaat aagcgaattt cttatgattt atgatttta ttattaaata    1200 agttataaaa aaataagtg tatacaaatt ttaaagtgac tcttaggttt taaaacgaaa    1260
attcttgttc ttgagtaact cttttcctgta ggtcaggttg ctttctcagg tatagcatga    1320
ggtcgctctt attgaccaca cctctaccgg catgcccatg ggttcttttg aaaagcaagc    1380
ataaaagatc taaacataaa atctgtaaaa taacaagatg taaagataat gctaaatcat    1440
ttggcttttt gattgattgt acaggaaaat atacatcgca gggggttgac ttttaccatt    1500
tcaccgcaat ggaatcaaac ttgttgaaga gaatgttcac aggcgcatac gctacaatga    1560
cccgattctt gctagccttt tctcggtctt gcaaacaacc gccaactgat caatgcatcc    1620
tgcatggcgc gcctgatgag cctgaactgc ccgggcaaat cagctggacg tctgcctgca    1680
ttaatgaatc ggccaacgcg cggggagagg cggtttgcgt attgggcgct cttccgcttc    1740
ctcgctcact gactcgctgc gctcggtcgt tcggctgcgg cgagcggtat cagctcactc    1800
```

```
aaaggcggta atacggttat ccacagaatc aggggataac gcaggaaaga acatgtgagc   1860
aaaaggccag caaaaggcca ggaaccgtaa aaaggccgcg ttgctggcgt ttttccatag   1920
gctccgcccc cctgacgagc atcacaaaaa tcgacgctca agtcagaggt ggcgaaaccc   1980
gacaggacta taaagatacc aggcgtttcc ccctggaagc tccctcgtgc gctctcctgt   2040
tccgaccctg ccgcttaccg gatacctgtc cgcctttctc ccttcgggaa gcgtggcgct   2100
ttctcatagc tcacgctgta ggtatctcag ttcggtgtag gtcgttcgct ccaagctggg   2160
ctgtgtgcac gaaccccccg ttcagcccga ccgctgcgcc ttatccggta actatcgtct   2220
tgagtccaac ccgtaagac acgacttatc gccactggca gcagccactg gtaacaggat   2280
tagcagagcg aggtatgtag gcggtgctac agagttcttg aagtggtggc ctaactacgg   2340
ctacactaga aggacagtat ttggtatctg cgctctgctg aagccagtta ccttcggaaa   2400
aagagttggt agctcttgat ccggcaaaca aaccaccgct ggtagcggtg ttttttttgt   2460
ttgcaagcag cagattacgc gcagaaaaaa aggatctcaa gaagatcctt tgatcttttc   2520
tacggggtct gacgctcagt ggaacgaaaa ctcacgttaa gggattttgg tcatgagatt   2580
atcaaaaagg atcttcacct agatcctttt aaattaaaaa tgaagtttta atcaatcta   2640
aagtatatat gagtaaactt ggtctgacag ttaccaatgc ttaatcagtg aggcacctat   2700
ctcagcgatc tgtctatttc gttcatccat agttgcctga ctccccgtcg tgtagataac   2760
tacgatacgg gagggcttac catctggccc cagtgctgca atgataccgc gagacccacg   2820
ctcaccggct ccagatttat cagcaataaa ccagccagcc ggaagggccg agcgcagaag   2880
tggtcctgca actttatccg cctccatcca gtctattaat tgttgccggg aagctagagt   2940
aagtagttcg ccagttaata gtttgcgcaa cgttgttgcc attgctacag gcatcgtggt   3000
gtcacgctcg tcgtttggta tggcttcatt cagctccggt tcccaacgat caaggcgagt   3060
tacatgatcc cccatgttgt gcaaaaaagc ggttagctcc ttcggtcctc cgatcgttgt   3120
cagaagtaag ttggccgcag tgttatcact catggttatg gcagcactgc ataattctct   3180
tactgtcatg ccatccgtaa gatgcttttc tgtgactggt gagtactcaa ccaagtcatt   3240
ctgagaatag tgtatgcggc gaccgagttg ctcttgcccg gcgtcaatac gggataatac   3300
cgcgccacat agcagaactt taaaagtgct catcattgga aaacgttctt cggggcgaaa   3360
actctcaagg atcttaccgc tgttgagatc cagttcgatg taacccactc gtgcacccaa   3420
ctgatcttca gcatctttta ctttcaccag cgtttctggg tgagcaaaaa caggaaggca   3480
aaatgccgca aaaaagggaa taagggcgac acggaaatgt tgaatactca tactcttcct   3540
ttttcaatat tattgaagca tttatcaggg ttattgtctc atgagcggat acatatttga   3600
atgtatttag aaaaataaac aaatagggt tccgcgcaca tttccccgaa aagtgccacc   3660
tgacgcgccc tgtagcggcg cattaagcgc ggcgggtgtg gtggttacgc gcagcgtgac   3720
cgctacactt gccagcgccc tagcgcccgc tcctttcgct ttcttccctt cctttctcgc   3780
cacgttcgcc ggctttcccc gtcaagctct aaatcggggg ctccctttag ggttccgatt   3840
tagtgcttta cggcacctcg accccaaaaa acttgattag ggtgatggtt cacgtagtgg   3900
gccatcgccc tgatagacgg ttttttcgccc tttgacgttg gagtccacgt tctttaatag   3960
tggactcttg ttccaaactg gaacaacact caaccctatc tcggtctatt cttttgattt   4020
ataagggatt tgccgatttc ggcctattgg ttaaaaaat gagctgattt aacaaaaatt   4080
taacgcgaat tttaacaaaa tattaacgct tacaatttcc attcgccatt caggctgcgc   4140
aactgttggg aagggcgatc ggtgcgggcc tcttcgctat tacgccag                4188
```

<210> SEQ ID NO 4
<211> LENGTH: 11466
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1962)..(2765)
<223> OTHER INFORMATION: URA3, orotidine-5'-phosphate decarboxylase coding sequence
<220> FEATURE:
<221> NAME/KEY: misc_feature
<222> LOCATION: (3560)..(4247)
<223> OTHER INFORMATION: Tetrahymena thermophila macronuclear telomere
<220> FEATURE:
<221> NAME/KEY: misc_feature
<222> LOCATION: (4893)..(5552)
<223> OTHER INFORMATION: HIS3, imidazoleglycerolphosphate dehydratase, coding sequence
<220> FEATURE:
<221> NAME/KEY: misc_feature
<222> LOCATION: (6024)..(6711)
<223> OTHER INFORMATION: Tetrahymena thermophila macronuclear telomere
<220> FEATURE:
<221> NAME/KEY: rep_origin
<222> LOCATION: (7198)..(7198)
<223> OTHER INFORMATION: Origin of replication, PMB1
<220> FEATURE:
<221> NAME/KEY: misc_feature
<222> LOCATION: (7956)..(8816)
<223> OTHER INFORMATION: AP(R), beta-lactamase, ampR ampicillin resistance, coding sequence
<220> FEATURE:
<221> NAME/KEY: misc_feature
<222> LOCATION: (9129)..(9803)
<223> OTHER INFORMATION: TRP1, phosphoribosylanthranilate isomerase, coding sequence
<220> FEATURE:
<221> NAME/KEY: misc_feature
<222> LOCATION: (9644)..(10388)
<223> OTHER INFORMATION: Autonomous replicating sequence
<220> FEATURE:
<221> NAME/KEY: misc_feature
<222> LOCATION: (10488)..(11465)
<223> OTHER INFORMATION: Centromere IV

<400> SEQUENCE: 4

| | | | | | |
|---|---|---|---|---|---|
| ttctcatgtt | tgacagctta | tcatcgataa | gctttaatgc | ggtagtttat | cacagttaaa | 60 |
| ttgctaacgc | agtcaggcac | cgtgtatgaa | atctaacaat | gcgctcatcg | tcatcctcgg | 120 |
| caccgtcacc | ctggatgctg | taggcatagg | cttggttatg | ccggtactgc | cgggcctctt | 180 |
| gcgggatatc | gtccattccg | acagcatcgc | cagtcactat | ggcgtgctgc | tagcgctata | 240 |
| tgcgttgatg | caatttctat | gcgcacccgt | tctcggagca | ctgtccgacc | gctttggccg | 300 |
| ccgcccagtc | ctgctcgctt | cgctacttgg | agccactatc | gactacgcga | tcatggcgac | 360 |
| cacacccgtc | ctgtggatca | attccctttta | gtataaattt | cactctgaac | catcttggaa | 420 |
| ggaccggtaa | ttatttcaaa | tctctttttc | aattgtatat | gtgttatgtt | atgtagtata | 480 |
| ctctttcttc | aacaattaaa | tactctcggt | agccaagttg | gtttaaggcg | caagacttta | 540 |
| atttatcact | acggaattgg | cgcgccaatt | ccgtaatctt | gagatcgggc | gttcgatcgc | 600 |
| cccgggagat | ttttttgttt | tttatgtctt | ccattcactt | cccagacttg | caagttgaaa | 660 |
| tatttctttc | aagggaattg | atcctctacg | ccggacgcat | cgtggccggc | atcaccggcg | 720 |
| ccacaggtgc | ggttgctggc | gcctatatcg | ccgacatcac | cgatgggaa | gatcgggctc | 780 |
| gccacttcgg | gctcatgagc | gcttgtttcg | gcgtgggtat | ggtggcaggc | cccgtggccg | 840 |

```
ggggactgtt gggcgccatc tccttgcatg caccattcct tgcggcgcg gtgctcaacg      900
gcctcaacct actactgggc tgcttcctaa tgcaggagtc gcataaggga gagcgtcgac      960
cgatgccctt gagagccttc aacccagtca gctccttccg gtgggcgcgg ggcatgacta     1020
tcgtcgccgc acttatgact gtcttcttta tcatgcaact cgtaggacag gtgccggcag     1080
cgctctgggt cattttcggc gaggaccgct ttcgctggag cgcgacgatg atcggcctgt     1140
cgcttgcggt attcggaatc ttgcacgccc tcgctcaagc cttcgtcact ggtcccgcca     1200
ccaaacgttt cggcgagaag caggccatta tcgccggcat ggcggccgac gcgctgggct     1260
acgtcttgct ggcgttcgcg acgcgaggct ggatggcctt ccccattatg attcttctcg     1320
cttccggcgg catcgggatg cccgcgttgc aggccatgct gtccaggcag gtagatgacg     1380
accatcaggg acagcttcaa ggatcgctcg cggctcttac cagcctaact tcgatcactg     1440
gaccgctgat cgtcacggcg atttatgccg cctcggcgag cacatggaac gggttggcat     1500
ggattgtagg cgccgcccta taccttgtct gcctccccgc gttgcgtcgc ggtgcatgga     1560
gccgggccac ctcgacctga atggaagccg gcggcacctc gctaacggat tcaccactcc     1620
aagaattgga gccaatcaat tcttgcggag aactgtgaat gcgcaaacca acccttggca     1680
gaacatatcc atcgcgtccg ccatctccag cagccgcacg cggcgcatcc cccccccct      1740
ttcaattcaa ttcatcattt ttttttattt ctttttttg atttcggttt ctttgaaatt      1800
tttttgattc ggtaatctcc gaacagaagg aagaacgaag gaaggagcac agacttagat     1860
tggtatatat acgcatatgt agtgttgaag aaacatgaaa ttgcccagta ttcttaaccc     1920
aactgcacag aacaaaaacc tgcaggaaac gaagataaat catgtcgaaa gctacatata     1980
aggaacgtgc tgctactcat cctagtcctg ttgctgccaa gctatttaat atcatgcacg     2040
aaaagcaaac aaacttgtgt gcttcattgg atgttcgtac caccaaggaa ttactggagt     2100
tagttgaagc attaggtccc aaaatttgtt tactaaaaac acatgtggat atcttgactg     2160
attttttccat ggagggcaca gttaagccgc taaaggcatt atccgccaag tacaattttt     2220
tactcttcga agacagaaaa tttgctgaca ttggtaatac agtcaaattg cagtactctg     2280
cgggtgtata cagaatagca gaatgggcag acattacgaa tgcacacggt gtggtgggcc     2340
caggtattgt tagcggttg aagcaggcgg cagaagaagt aacaaaggaa cctagaggcc     2400
ttttgatgtt agcagaattg tcatgcaagg gctccctatc tactggagaa tatactaagg     2460
gtactgttga cattgcgaag agcgacaaag attttgttat cggctttatt gctcaaagag     2520
acatgggtgg aagagatgaa ggttacgatt ggttgattat gacacccggt gtgggtttag     2580
atgacaaggg agacgcattg ggtcaacagt atagaaccgt ggatgatgtg gtctctacag     2640
gatctgacat tattattgtt ggaagaggac tatttgcaaa gggaagggat gctaaggtag     2700
agggtgaacg ttacagaaaa gcaggctggg aagcatattt gagaagatgc ggccagcaaa     2760
actaaaaac tgtattataa gtaaatgcat gtatactaaa ctcacaaatt agagcttcaa     2820
tttaattata tcagttatta ctcgggcgta atgattttta taatgacgaa aaaaaaaaa      2880
ttggaaagaa aaggggggg gggcagcgtt gggtcctggc cacgggtgcg catgatcgtg     2940
ctcctgtcgt tgaggacccg gctaggctgg cggggttgcc ttactggtta gcagaatgaa     3000
tcaccgatac gcgagcgaac gtgaagcgac tgctgctgca aaacgtctgc gacctgagca     3060
acaacatgaa tggtcttcgg tttccgtgtt tcgtaaagtc tggaaacgcg gaagtcagcg     3120
ccctgcacca ttatgttccg gatctgcatc gcaggatgct gctggctacc ctgtggaaca     3180
cctacatctg tattaacgaa gcgctggcat tgaccctgag tgatttttct ctggtcccgc     3240
```

```
cgcatccata ccgccagttg tttaccctca caacgttcca gtaaccgggc atgttcatca    3300
tcagtaaccc gtatcgtgag catcctctct cgtttcatcg gtatcattac ccccatgaac    3360
agaaattccc ccttacacgg aggcatcaag tgaccaaaca ggaaaaaacc gcccttaaca    3420
tggcccgctt tatcagaagc cagacattaa cgcttctgga gaaactcaac gagctggacg    3480
cggatgaaca ggcagacatc tgtgaatcgc ttcacgacca cgctgatgag ctttaccgca    3540
gccctcgagg gataagcttc attttagat aaaatttatt aatcatcatt aatttcttga    3600
aaaacatttt atttattgat cttttataac aaaaaccct tctaaaagtt tattttgaa     3660 tgaaaaactt ataaaatttt atgaaaacta caaaaaataa aattttaat taaaataatt    3720 ttgataagaa cttcaatctt tgactagcta gcttagtcat ttttgagatt taattaatat    3780
tttatgttta ttcatatata aactattcaa aatattatag aatttaaaca ttttaacatc    3840
ttaatcattc ataaataact aaaaatcaaa gtattcatc aataaataac ttttactcaa     3900
tgtcaaagaa ttattggggt tggggttggg gttggggttg gggttggggt tggggttggg    3960
gttggggttg gggttggggt tggggttggg gttggggttg gggttggggt tggggttggg    4020
gttggggttg gggttggggt tggggttggg gttggggttg gggttggggt tggggttggg    4080
gttggggttg gggttggggt tggggttggg gttggggttg gggttggggt tggggttggg    4140
gttggggttg gggttggggt tggggttggg gttggggttg gggtgggaaa acagcattca    4200
ggtattagaa gaatatcctg attcaggtga aaatattgtt gatgcgcggg atcctcgggg    4260
acaccaaata tggcgatctc ggccttttcg tttcttggag ctgggacatg tttgccatcg    4320
atccatctac caccagaacg gccgttagat ctgctgccac cgttgtttcc accgaagaaa    4380
ccaccgttgc cgtaaccacc acgacggttg ttgctaaaga agctgccacc gccacggcca    4440
ccgttgtagc cgccgttgtt gttattgtag ttgctcatgt tatttctggc acttcttggt    4500
tttcctctta agtgaggagg aacataacca ttctcgttgt tgtcgttgat gcttaaattt    4560
tgcacttgtt cgctcagttc agccataata tgaaatgctt ttcttgttgt tcttacggaa    4620
taccacttgc cacctatcac cacaactaac ttttcccgt tcctccatct cttttatatt     4680 tttttctcg atcgagttca agagaaaaaa aagaaaaag caaaaagaaa aaggaaagc       4740 gcgcctcgtt cagaatgaca cgtatagaat gatgcattac cttgtcatct tcagtatcat    4800
actgttcgta tacatactta ctgacattca taggtataca tatatacaca tgtatatata    4860
tcgtatgctg cagcttttaaa taatcggtgt cactacataa gaacaccttt ggtggaggga    4920
acatcgttgg taccattggg cgaggtggct tctcttatgg caaccgcaag agccttgaac    4980
gcactctcac tacggtgatg atcattcttg cctcgcagac aatcaacgtg gagggtaatt    5040
ctgctagcct ctgcaaagct ttcaagaaaa tgcgggatca tctcgcaaga gagatctcct    5100
actttctccc tttgcaaacc aagttcgaca actgcgtacg gcctgttcga agatctacc    5160 accgctctgg aaagtgcctc atccaaaggc gcaaatcctg atccaaacct ttttactcca    5220
cgcgccagta gggcctcttt aaaagcttga ccgagagcaa tcccgcagtc ttcagtggtg    5280
tgatggtcgt ctatgtgtaa gtcaccaatg cactcaacga ttagcgacca gccggaatgc    5340
ttggccagag catgtatcat atggtccaga aaccctatac ctgtgtggac gttaatcact    5400
tgcgattgtg tggcctgttc tgctactgct tctgcctctt tttctgggaa gatcgagtgc    5460
tctatcgcta ggggaccacc ctttaaagag atcgcaatct gaatcttggt ttcatttgta    5520
atacgcttta ctagggcttt ctgctctgtc atctttgcct tcgtttatct tgcctgctca    5580
```

```
tttttttagta tattcttcga agaaatcaca ttactttata taatgtataa ttcattatgt   5640
gataatgcca atcgctaaga aaaaaaaga gtcatccgct aggtggaaaa aaaaaaatga   5700
aaatcattac cgaggcataa aaaaatatag agtgtactag aggaggccaa gagtaataga   5760 aaagaaaat tgcgggaaag gactgtgtta tgacttccct gactaatgcc gtgttcaaac   5820
gatacctggc agtgactcct agcgctcacc aagctcttaa aacgagaatt aagaaaaagt   5880
cgtcatcttt cgataagttt tcccacagc aaagcaatag tagaaaaaaa caatgggaaa   5940
cgttgaatga agacaaagcg tcgtggttta aaggaaata cgctcacgta catgctaggg   6000
aacaggaccg tgcagcggat cccgcgcatc aacaatattt tcacctgaat caggatattc   6060
ttctaatacc tgaatgctgt tttcccaccc caaccccaac cccaacccca accccaaccc   6120
caaccccaac cccaacccca accccaaccc caaccccaac cccaacccca accccaaccc   6180
caaccccaac cccaacccca accccaaccc caaccccaac cccaacccca accccaaccc   6240
caaccccaac cccaacccca accccaaccc caaccccaac cccaacccca accccaaccc   6300
caaccccaac cccaacccca accccaaccc caaccccaac cccaacccca accccaataa   6360
ttctttgaca ttgagtaaaa gttatttatt gatgtaatac tttgattttt agttatttat   6420
gaatgattaa gatgttaaaa tgtttaaatt ctataatatt ttgaatagtt tatatatgaa   6480
taaacataaa atattaatta aatctcaaaa atgactaagc tagctagtca aagattgaag   6540
ttcttatcaa aattatttta attaaaaatt ttatttttg tagttttcat aaatttttat   6600 aagttttca ttcaaaaata aactttaga agggttttt gttataaaag atcaataaat   6660
aaaatgtttt tcaagaaatt aatgatgatt aataaatttt atctaaaaat gaagcttatc   6720
cctcgagggc tgcctcgcgc gtttcggtga tgacggtgaa aacctctgac acatgcagct   6780
cccggagacg gtcacagctt gtctgtaagc ggatgccggg agcagacaag cccgtcaggg   6840
cgcgtcagcg ggtgttggcg ggtgtcgggg cgcagccatg acccagtcac gtagcgatag   6900
cggagtgtat actggcttaa ctatgcggca tcagagcaga ttgtactgag agtgcaccat   6960
atgcggtgtg aaataccgca cagatgcgta aggagaaaat accgcatcag gcgctcttcc   7020
gcttcctcgc tcactgactc gctgcgctcg gtcgttcggc tgcggcgagc ggtatcagct   7080
cactcaaagg cggtaatacg gttatccaca gaatcagggg ataacgcagg aaagaacatg   7140
tgagcaaaag gccagcaaaa ggccaggaac cgtaaaaagg ccgcgttgct ggcgtttttc   7200
cataggctcc gccccctga cgagcatcac aaaaatcgac gctcaagtca gaggtggcga   7260
aacccgacag gactataaag ataccaggcg tttccccctg gaagctccct cgtgcgctct   7320
cctgttccga cctgccgct taccggatac ctgtccgcct ttctcccttc gggaagcgtg   7380
gcgctttctc atagctcacg ctgtaggtat ctcagttcgg tgtaggtcgt tcgctccaag   7440
ctgggctgtg tgcacgaacc ccccgttcag cccgaccgct gcgccttatc cggtaactat   7500
cgtcttgagt ccaacccggt aagacacgac ttatcgccac tggcagcagc cactggtaac   7560
aggattagca gagcgaggta tgtaggcggt gctacagagt tcttgaagtg gtggcctaac   7620
tacggctaca ctagaaggac agtatttggt atctgcgctc tgctgaagcc agttaccttc   7680
ggaaaaagag ttggtagctc ttgatccggc aaacaaacca ccgctggtag cggtggtttt   7740
tttgtttgca agcagcagat tacgcgcaga aaaaaggat ctcaagaaga tcctttgatc   7800
ttttctacgg ggtctgacgc tcagtggaac gaaaactcac gttaagggat tttggtcatg   7860
agattatcaa aaaggatctt cacctagatc cttttaaatt aaaaatgaag ttttaaatca   7920
atctaaagta tatatgagta aacttggtct gacagttacc aatgcttaat cagtgaggca   7980
```

```
cctatctcag cgatctgtct atttcgttca tccatagttg cctgactccc cgtcgtgtag    8040
ataactacga tacgggaggg cttaccatct ggccccagtg ctgcaatgat accgcgagac    8100
ccacgctcac cggctccaga tttatcagca ataaaccagc cagccggaag ggccgagcgc    8160
agaagtggtc ctgcaacttt atccgcctcc atccagtcta ttaattgttg ccgggaagct    8220
agagtaagta gttcgccagt taatagtttg cgcaacgttg ttgccattgc tgcaggcatc    8280
gtggtgtcac gctcgtcgtt tggtatggct tcattcagct ccggttccca acgatcaagg    8340
cgagttacat gatcccccat gttgtgcaaa aaagcggtta gctccttcgg tcctccgatc    8400
gttgtcagaa gtaagttggc cgcagtgtta tcactcatgg ttatggcagc actgcataat    8460
tctcttactg tcatgccatc cgtaagatgc ttttctgtga ctggtgagta ctcaaccaag    8520
tcattctgag aatagtgtat gcggcgaccg agttgctctt gcccggcgtc aacacgggat    8580
aataccgcgc cacatagcag aactttaaaa gtgctcatca ttggaaaacg ttcttcgggg    8640
cgaaaactct caaggatctt accgctgttg agatccagtt cgatgtaacc cactcgtgca    8700
cccaactgat cttcagcatc ttttactttc accagcgttt ctgggtgagc aaaaacagga    8760
aggcaaaatg ccgcaaaaaa gggaataagg gcgacacgga aatgttgaat actcatactc    8820
ttcctttttc aatattattg aagcatttat cagggttatt gtctcatgag cggatacata    8880
tttgaatgta tttagaaaaa taaacaaata ggggttccgc gcacatttcc ccgaaaagtg    8940
ccacctgacg tctaagaaac cattattatc atgacattaa cctataaaaa taggcgtatc    9000
acgaggccct ttcgtcttca agaattaatt cggtcgaaaa agaaaaagga gagggccaag    9060
agggagggca ttggtgacta ttgagcacgt gagtatacgt gattaagcac acaaaggcag    9120
cttggagtat gtctgttatt aatttcacag gtagttctgg tccattggtg aaagtttgcg    9180
gcttgcagag cacagaggcc gcagaatgtg ctctagattc cgatgctgac ttgctgggta    9240
ttatatgtgt gcccaataga aagagaacaa ttgacccggt tattgcaagg aaaatttcaa    9300
gtcttgtaaa agcatataaa aatagttcag gcactccgaa atacttggtt ggcgtgtttc    9360
gtaatcaacc taaggaggat gttttggctc tggtcaatga ttacggcatt gatatcgtcc    9420
aactgcatgg agatgagtcg tggcaagaat accaagagtt cctcggtttg ccagttatta    9480
aaagactcgt atttccaaaa gactgcaaca tactactcag tgcagcttca cagaaacctc    9540
attcgtttat tcccttgttt gattcagaag caggtgggac aggtgaactt ttggattgga    9600
actcgatttc tgactgggtt ggaaggcaag agagccccga aagcttacat tttatgttag    9660
ctggtggact gacgccagaa aatgttggtg atgcgcttag attaaatggc gttattggtg    9720
ttgatgtaag cggaggtgtg gagacaaatg gtgtaaaaga ctctaacaaa atagcaaatt    9780
tcgtcaaaaa tgctaagaaa taggttatta ctgagtagta tttatttaag tattgtttgt    9840
gcacttgcct gcaggccttt tgaaaagcaa gcataaaaga tctaaacata aaatctgtaa    9900
aataacaaga tgtaaagata atgctaaatc atttggcttt ttgattgatt gtacaggaaa    9960
atatacatcg caggggttg acttttacca tttcaccgca atggaatcaa acttgttgaa   10020
gagaatgttc acaggcgcat acgctacaat gacccgattc ttgctagcct tttctcggtc   10080
ttgcaaacaa ccgccggcag cttagtatat aaatacacat gtacatacct ctctccgtat   10140
cctcgtaatc attttcttgt atttatcgtc ttttcgctgt aaaaacttta tcacacttat   10200
ctcaaataca cttattaacc gcttttacta ttatcttcta cgctgacagt aatatcaaac   10260
agtgacacat attaaacaca gtggtttctt tgcataaaca ccatcagcct caagtcgtca   10320
```

-continued

```
agtaaagatt tcgtgttcat gcagatagat aacaatctat atgttgataa ttagcgttgc    10380
ctcatcaatg cgagatccgt ttaaccggac cctagtgcac ttaccccacg ttcggtccac    10440
tgtgtgccga acatgctcct tcactatttt aacatgtgga attaattcta aatcctcttt    10500
atatgatctg ccgatagata gttctaagtc attgaggttc atcaacaatt ggattttctg    10560
tttactcgac ttcaggtaaa tgaaatgaga tgatacttgc ttatctcata gttaactcta    10620
agaggtgata cttatttact gtaaaactgt gacgataaaa ccggaaggaa gaataagaaa    10680
actcgaactg atctataatg cctatttttct gtaaagagtt taagctatga aagcctcggc    10740
attttggccg ctcctaggta gtgcttttt tccaaggaca aaacagtttc tttttcttga    10800
gcaggtttta tgtttcggta atcataaaca ataaataaat tatttcattt atgtttaaaa    10860
ataaaaaata aaaagtatt ttaaattttt aaaaagttg attataagca tgtgacctt    10920 tgcaagcaat taaattttgc aatttgtgat tttaggcaaa agttacaatt tctggctcgt    10980
gtaatatatg tatgctaaag tgaacttta caaagtcgat atggacttag tcaaaagaaa    11040
ttttcttaaa aatatatagc actagccaat ttagcacttc tttatgagat atattataga    11100
ctttattaag ccagatttgt gtattatatg tatttacccg gcgaatcatg gacatacatt    11160
ctgaaatagg taatattctc tatggtgaga cagcatagat aacctaggat acaagttaaa    11220
agctagtact gttttgcagt aattttttttc tttttataa gaatgttacc acctaaataa    11280
gttataaagt caatagttaa gtttgatatt tgattgtaaa ataccgtaat atatttgcat    11340
gatcaaaagg ctcaatgttg actagccagc atgtcaacca ctatattgat caccgatata    11400
tggacttcca caccaactag taatatgaca ataaattcaa gatattcttc atgagaatgg    11460
cccaga                                                              11466
```

<210> SEQ ID NO 5
<211> LENGTH: 15
<212> TYPE: DNA
<213> ORGANISM: Artificial
<220> FEATURE:
<223> OTHER INFORMATION: AarI recognition site
<220> FEATURE:
<221> NAME/KEY: misc_feature
<222> LOCATION: (8)..(15)
<223> OTHER INFORMATION: n is a, c, g, or t

<400> SEQUENCE: 5
cacctgcnnn nnnnn                                                        15

<210> SEQ ID NO 6
<211> LENGTH: 37
<212> TYPE: DNA
<213> ORGANISM: Artificial
<220> FEATURE:
<223> OTHER INFORMATION: AloI recognition site
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (17)..(22)
<223> OTHER INFORMATION: n is a, c, g, or t
<220> FEATURE:
<221> NAME/KEY: misc_feature
<222> LOCATION: (26)..(37)
<223> OTHER INFORMATION: n is a, c, g, or t

<400> SEQUENCE: 6
nnnnnnnnnn nngaacnnnn nntccnnnnn nnnnnnn                                 37

```
<210> SEQ ID NO 7
<211> LENGTH: 38
<212> TYPE: DNA
<213> ORGANISM: Artificial
<220> FEATURE:
<223> OTHER INFORMATION: BaeI recognition site
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (18)..(21)
<223> OTHER INFORMATION: n is a, c, g, or t
<220> FEATURE:
<221> NAME/KEY: misc_feature
<222> LOCATION: (27)..(38)
<223> OTHER INFORMATION: n is a, c, g, or t

<400> SEQUENCE: 7
nnnnnnnnnn nnnnacnnn ngtaycnnnn nnnnnnnn                    38

<210> SEQ ID NO 8
<211> LENGTH: 37
<212> TYPE: DNA
<213> ORGANISM: Artificial
<220> FEATURE:
<223> OTHER INFORMATION: PpiI recognition site
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (17)..(21)
<223> OTHER INFORMATION: n is a, c, g, or t
<220> FEATURE:
<221> NAME/KEY: misc_feature
<222> LOCATION: (25)..(37)
<223> OTHER INFORMATION: n is a, c, g, or t

<400> SEQUENCE: 8
nnnnnnnnnn nngaacnnnn nctcnnnnnn nnnnnnn                    37

<210> SEQ ID NO 9
<211> LENGTH: 11
<212> TYPE: DNA
<213> ORGANISM: Artificial
<220> FEATURE:
<223> OTHER INFORMATION: SapI recognition site
<220> FEATURE:
<221> NAME/KEY: misc_feature
<222> LOCATION: (8)..(11)
<223> OTHER INFORMATION: n is a, c, g, or t

<400> SEQUENCE: 9
gctcttcnnn n                                                11

<210> SEQ ID NO 10
<211> LENGTH: 13
<212> TYPE: DNA
<213> ORGANISM: Artificial
<220> FEATURE:
<223> OTHER INFORMATION: SdiI recognition site
<220> FEATURE:
<221> NAME/KEY: misc_feature
<222> LOCATION: (5)..(9)
<223> OTHER INFORMATION: n is a, c, g, or t

<400> SEQUENCE: 10
```

```
ggccnnnnng gcc                                                     13
```

```
<210> SEQ ID NO 11
<211> LENGTH: 13
<212> TYPE: DNA
<213> ORGANISM: Artificial
<220> FEATURE:
<223> OTHER INFORMATION: SfiI recognition site
<220> FEATURE:
<221> NAME/KEY: misc_feature
<222> LOCATION: (5)..(9)
<223> OTHER INFORMATION: n is a, c, g, or t

<400> SEQUENCE: 11
ggccnnnnng gcc                                                     13

<210> SEQ ID NO 12
<211> LENGTH: 11
<212> TYPE: DNA
<213> ORGANISM: Artificial
<220> FEATURE:
<223> OTHER INFORMATION: VpaK32I recognition site
<220> FEATURE:
<221> NAME/KEY: misc_feature
<222> LOCATION: (8)..(11)
<223> OTHER INFORMATION: n is a, c, g, or t

<400> SEQUENCE: 12
gctcttcnnn n                                                       11

<210> SEQ ID NO 13
<211> LENGTH: 18
<212> TYPE: DNA
<213> ORGANISM: Artificial
<220> FEATURE:
<223> OTHER INFORMATION: I-Sce I recognition site

<400> SEQUENCE: 13
tagggataac agggtaat                                                18

<210> SEQ ID NO 14
<211> LENGTH: 15
<212> TYPE: DNA
<213> ORGANISM: Artificial
<220> FEATURE:
<223> OTHER INFORMATION: I-Ceu I recognition site

<400> SEQUENCE: 14
acggtcctaa ggtag                                                   15

<210> SEQ ID NO 15
<211> LENGTH: 19
<212> TYPE: DNA
<213> ORGANISM: Artificial
<220> FEATURE:
<223> OTHER INFORMATION: I-Cre I recognition site

<400> SEQUENCE: 15
aaacgtcgtg agacagttt                                               19

<210> SEQ ID NO 16
<211> LENGTH: 15
<212> TYPE: DNA
<213> ORGANISM: Artificial
<220> FEATURE:
<223> OTHER INFORMATION: I-Sce II recognition site

<400> SEQUENCE: 16
```

```
ggtcaccctg aagta                                             15

<210> SEQ ID NO 17
<211> LENGTH: 18
<212> TYPE: DNA
<213> ORGANISM: Artificial
<220> FEATURE:
<223> OTHER INFORMATION: I-Sce III recognition site

<400> SEQUENCE: 17
gttttggtaa ctatttat                                          18

<210> SEQ ID NO 18
<211> LENGTH: 25
<212> TYPE: DNA
<213> ORGANISM: Artificial
<220> FEATURE:
<223> OTHER INFORMATION: Endo. Sce I recognition site

<400> SEQUENCE: 18
gatgctgcag gcataggctt gttta                                  25

<210> SEQ ID NO 19
<211> LENGTH: 12
<212> TYPE: DNA
<213> ORGANISM: Artificial
<220> FEATURE:
<223> OTHER INFORMATION: PI-Sce I recognition site

<400> SEQUENCE: 19
gggtgcggag aa                                                12

<210> SEQ ID NO 20
<211> LENGTH: 30
<212> TYPE: DNA
<213> ORGANISM: Artificial
<220> FEATURE:
<223> OTHER INFORMATION: PI-Psp I recognition site

<400> SEQUENCE: 20
tggcaaacag ctattatggg tattatgggt                             30

<210> SEQ ID NO 21
<211> LENGTH: 14
<212> TYPE: DNA
<213> ORGANISM: Artificial
<220> FEATURE:
<223> OTHER INFORMATION: I-Ppo I recognition site

<400> SEQUENCE: 21
ctctcttaag gtag                                              14

<210> SEQ ID NO 22
<211> LENGTH: 13
<212> TYPE: DNA
<213> ORGANISM: Artificial
<220> FEATURE:
<223> OTHER INFORMATION: HO recognition site

<400> SEQUENCE: 22
tttccgcaac agt                                               13

<210> SEQ ID NO 23
<211> LENGTH: 36
<212> TYPE: DNA
```

-continued

```
<213> ORGANISM: Artificial
<220> FEATURE:
<223> OTHER INFORMATION: I-Tev I recognition site
<220> FEATURE:
<221> NAME/KEY: misc_feature
<222> LOCATION: (1)..(6)
<223> OTHER INFORMATION: n is a, c, g, or t

<400> SEQUENCE: 23
nnnnnntcag tagatgtttt tcttggtcta ccgttt                                         36
```